United States Patent
Ophardt et al.

(10) Patent No.: US 9,149,161 B2
(45) Date of Patent: *Oct. 6, 2015

(54) METHOD FOR GENERATING OZONE CONTAINING FLUID

(71) Applicant: OP-HYGIENE IP GmbH, Niederbipp (CH)

(72) Inventors: Heiner Ophardt, Arisdorf (CH); Andrew Jones, Smithville (CA)

(73) Assignee: OP-Hygiene IP GMBH, Neiderbipp (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/166,588

(22) Filed: Jan. 28, 2014

(65) Prior Publication Data
US 2014/0138401 A1 May 22, 2014

Related U.S. Application Data

(63) Continuation of application No. 13/470,025, filed on May 11, 2012, now Pat. No. 8,733,596, which is a
(Continued)

(30) Foreign Application Priority Data

Jan. 20, 2010 (CA) ........................ 2690890
Feb. 23, 2010 (CA) ........................ 2694569

(51) Int. Cl.
*B67D 7/78* (2010.01)
*A47K 5/12* (2006.01)
(Continued)

(52) U.S. Cl.
CPC ............ *A47K 5/1211* (2013.01); *A47K 5/1204* (2013.01); *A47K 5/1207* (2013.01); *A47K 5/1217* (2013.01); *A61L 2/202* (2013.01); *G01F 11/021* (2013.01); *G01F 11/025* (2013.01)

(58) Field of Classification Search
CPC . A47K 5/1204; A47K 5/1207; A47K 5/1211; A61L 2/202
USPC ............ 222/145.1, 145.5, 181.1, 181.3, 190; 422/24, 28, 186.07, 186.12, 292; 210/760
See application file for complete search history.

(56) References Cited

U.S. PATENT DOCUMENTS 3,500,451 A 3/1970 Yando
4,227,092 A 10/1980 Campagnuolo et al.
(Continued)

FOREIGN PATENT DOCUMENTS

DE 102007032297 A1 1/2009

OTHER PUBLICATIONS

U.S. Appl. No. 14/250,080; filed Apr. 10, 2014; Heiner Ophardt; office action dated Aug. 21, 2014.

*Primary Examiner* — Daniel R Shearer
(74) *Attorney, Agent, or Firm* — Thorpe North & Western, LLP

(57) ABSTRACT

A method of generating ozone containing fluid comprising: drawing atmospheric air into an air compartment, generating ozone within the air compartment from air in the air compartment by conversion within the compartment of oxygen in the air within the compartment into ozone to form ozonated air, discharging the ozonated air from the air compartment, mixing the ozonated discharged air with a flowable fluid to form an ozonated fluid-air mixture, and passing the ozonated fluid-air mixture out a discharge outlet. Preferably the method is carried out in a dispenser utilizing a piston pump to draw air through a corona discharge ozone generator and to draw liquid from a liquid reservoir and simultaneously pass both the ozonated air and liquid through a foam generator to generate foam.

16 Claims, 37 Drawing Sheets

Related U.S. Application Data continuation-in-part of application No. 12/929,315, filed on Jan. 14, 2011, now Pat. No. 8,672,187, and a continuation-in-part of application No. 12/659,127, filed on Feb. 25, 2010, now Pat. No. 8,201,707, and a continuation-in-part of application No. 12/379,786, filed on Feb. 27, 2009, now Pat. No. 8,215,523.

(51) Int. Cl.
*A61L 2/20* (2006.01)
*G01F 11/02* (2006.01)

(56) References Cited

U.S. PATENT DOCUMENTS

| | | |
|---|---|---|
| 4,331,262 A | 5/1982 | Snyder et al. |
| 4,701,835 A | 10/1987 | Campagnuolo et al. |
| 4,952,836 A | 8/1990 | Robertson |
| 5,124,132 A | 6/1992 | Francis, Jr. et al. |
| 5,132,193 A | 7/1992 | Reddy |
| 5,489,044 A | 2/1996 | Ophardt |
| 5,814,921 A | 9/1998 | Carroll |
| 5,945,068 A | 8/1999 | Ferone |
| 5,945,910 A | 8/1999 | Gorra |
| 5,975,714 A | 11/1999 | Vetorino et al. |
| 6,071,088 A | 6/2000 | Bishop et al. |
| 6,217,833 B1 | 4/2001 | Kolu |
| 6,287,515 B1 | 9/2001 | Koosman et al. |
| 6,407,484 B1 | 6/2002 | Oliver et al. |
| 6,409,050 B1 | 6/2002 | Ophardt et al. |
| 6,455,017 B1 | 9/2002 | Kasting et al. |
| 6,458,398 B1 | 10/2002 | Smith et al. |
| 6,521,194 B2 | 2/2003 | Yeh |
| 6,669,902 B1 | 12/2003 | Steiner et al. |
| 6,875,539 B2 | 4/2005 | Ophardt |
| 6,914,340 B2 | 7/2005 | Becker et al. |
| 6,964,739 B2 | 11/2005 | Boyd et al. |
| 7,008,523 B2 | 3/2006 | Herrington |
| 7,222,984 B2 | 5/2007 | Lee |
| 7,303,099 B2 | 12/2007 | Ophardt |
| 7,367,477 B2 | 5/2008 | Ophardt et al. |
| 7,527,178 B2 | 5/2009 | Lewis |
| 7,568,598 B2 | 8/2009 | Ophardt et al. |
| 7,621,426 B2 | 11/2009 | Reynolds et al. |
| 7,708,166 B2 | 5/2010 | Ophardt |
| 7,798,373 B1 | 9/2010 | Wroblewski et al. |
| 8,006,324 B2 | 8/2011 | Ophardt et al. |
| 8,047,404 B2 | 11/2011 | Quinlan et al. |
| 8,678,240 B2 | 3/2014 | O'Brien |
| 2002/0158085 A1 | 10/2002 | Ophardt et al. |
| 2004/0245281 A1 | 12/2004 | Oke |
| 2005/0171634 A1 | 8/2005 | York et al. |
| 2006/0233684 A1 * | 10/2006 | Centanni et al. ......... 422/186.12 |
| 2006/0237483 A1 | 10/2006 | Ophardt |
| 2008/0237368 A1 | 10/2008 | Hengsperger et al. |
| 2009/0008408 A1 | 1/2009 | Ophardt et al. |
| 2009/0045221 A1 | 2/2009 | Ophardt |
| 2009/0084082 A1 | 4/2009 | Martin et al. |
| 2009/0145296 A1 | 6/2009 | Ophardt |
| 2009/0145925 A1 | 6/2009 | Wegelin |
| 2009/0200340 A1 | 8/2009 | Ophardt |
| 2009/0266842 A1 | 10/2009 | Snodgrass |
| 2009/0308887 A1 | 12/2009 | Woo et al. |
| 2010/0111735 A1 | 5/2010 | Tu |
| 2010/0213212 A1 | 8/2010 | Custodis et al. |
| 2011/0108410 A1 | 5/2011 | Ophardt |
| 2011/0303762 A1 | 12/2011 | Wegelin et al. |

* cited by examiner

METHOD FOR GENERATING OZONE CONTAINING FLUID

RELATED APPLICATION

This application is a continuation of U.S. patent application Ser. No. 13/470,025 filed May 11, 2012 which is a continuation-in-part of U.S. patent application Ser. No. 12/929,315 filed Jan. 14, 2011 which is a continuation-in-part of U.S. patent application Ser. No. 12/659,127 filed Feb. 25, 2010 which is a continuation-in-part of U.S. patent application Ser. No. 12/379,786 filed Feb. 27, 2009 and claims the benefit of 35 U.S.C. 120.

SCOPE OF THE INVENTION

This invention relates to a product dispensing apparatus adapted for using manually applied forces from a user not only to dispense product but also to generate electrical energy as, for example, use in powering of a communication link associated with the dispensing apparatus and estimating the amount of product dispensed.

This invention also relates to a method and apparatus of generating ozone containing fluids including foam and, more particularly, to a method of dispensing and dispensers for dispensing fluids containing ozone, preferably as a foam of ozonated air and liquid.

This invention also relates to an advantageous construction of a pump for use in dispensing fluids with or without ozone.

BACKGROUND OF THE INVENTION

Various manual dispensers of products are well known for dispensing products such as hand and skin cleaning fluids, whether as liquids or foamed soap, paper towel dispensers as for use in washrooms, toilet tissue dispensers as for use in washrooms, toilet cover dispensers as for use in washrooms, feminine hygiene product dispensers, and beverage dispensers in cafeterias. Known such manual dispensers are manually operated in the sense that manual forces are applied to dispense the product. One difficulty which arises with such dispensing apparatus is to provide for timely maintenance, servicing and monitoring such as, for example, to ensure that there is always product to be dispensed and that the dispenser is operating properly.

The present inventor has appreciated a desire to provide for communication of such dispensing apparatus with various other systems. However, a disadvantage arises insofar as such manual dispensers are not connected to any electrical power source and thus are not adapted to drive electrically powered communication systems.

Replaceable batteries are known for placement in dispensing apparatus so as to drive dispensing motors and/or electronics associated with the apparatus, however, such replaceable batteries suffer the disadvantage that they are another component of the system which is prone to failure. Moreover, in manual dispensing apparatus, the cost of the batteries substantially decreases the commercial viability of the manual dispensing apparatus particularly in a competitive market favouring simple inexpensive manually operated dispensing apparatus.

Fuel cells for the creation of electrical energy by the conversion of alcohol compounds, such as ethanol, are known as are techniques for manufacturing such fuel cells in the mass production manner as on the plastic film.

Direct alcohol fuel cells are taught in U.S. Pat. No. 5,132,193 to Ready, issued Jul. 21, 1992 which teaches generation of electricity in a small compact alcohol fuelled fuel cell electric power plant in which poisoning by reaction intermediates is avoided or minimized. As alcohol fuels, lower primary alcohols are preferred particularly methanol and ethanol with other lower primary alcohols such as 1-propanol, 1-butanol and n-amyl alcohol also operative.

Piezoelectricity is the ability of some materials notably crystals and certain ceramics to generate an electric field or electric potential in response to applied mechanical stress. A piezoelectric generator converts motion and force to electrical power, as charge and voltage. A piezoelectric generator can be configured to generate an electric potential when the generator is bent, compressed or stretched by the manual energy applied in manually activating a dispenser. For example, a piezoceramic may be constructed to generate a voltage differential across its electrodes when the piezoceramic is bent, compressed or stretched.

Persons skilled in the art appreciates that there are multiple ways to fabricate piezoceramic that creates an electrical voltage when deformed. In one method, two compressing piezoceramics are stacked together. The piezoceramics are polarized in opposite directions. When such a stack is mechanically bent, one piezoceramic compresses while the other one stretches and an electric potential is created across the stack or a portion of the stack. A single piezoceramic layer may also be polarized to create an electrical potential when bent.

Previously known soap dispensers suffer the disadvantage that they do not have the capability to readily determine the amount of fluid dispensed or the amount of fluid remaining in a reservoir.

Many fluids are known as useful for cleaning and disinfecting.

Ozone ($O_3$) is a strong oxidizing agent having an oxygenation potential more than 1.5 times that of chlorine and approximately 1.2 times that of hydrogen peroxide. Ozone is normally produced by passing an oxygen-containing gas through ultraviolet light or a corona discharge. Ozone has been shown to be a relatively reactive oxidant capable of destroying pathogenic microorganisms. Ozone naturally decomposes into oxygen within relatively short periods of time.

Presently known devices do not provide for adequate methods or apparatus for generation and dispensing of small amounts of ozone as can be useful, for example, in hand cleaning soap dispensers.

Piston pumps are known for engagement in the neck of a fluid containing bottle to dispense fluid from the bottle. Such known pumps suffer a disadvantage as to the limited volume which can be provide in compartments formed in the pump, particularly compartments to receive air.

SUMMARY OF THE INVENTION

To at least partially overcome some of these disadvantages of previously known devices, the present invention provides a dispensing apparatus in which product is dispensed by a user moving an actuation mechanism and in which an electrical generator is provided for generating electrical energy such that, as a result of movement of the activation mechanism, the generator generates electrical power.

To at least partially overcome some of these disadvantages of previously known devices, the present invention provides a method of generating ozone containing fluid comprising drawing atmospheric air into an air compartment, generating ozone within the air compartment, discharging the ozonated air from the air compartment and mixing the ozonated air with a flowable fluid to form a ozonated fluid air mixture. Preferably, the method is carried out in a pump having the air compartment, more preferably with the air compartment having a volume which varies with operation of the pump. Preferably, the ozonated fluid-air mixture are dispensed in the form of a foam.

To at least partially overcome other disadvantages of the previously known devices, the present invention provides a construction for a piston pump to be received in a neck of a container having a compartment outside the neck of a greater diameter than the diameter of the neck.

An object of the present invention is to provide an inexpensive dispensing apparatus preferably a fluid dispensing apparatus with an electrical generator for generating electrical energy.

Another object is to provide a dispensing apparatus preferably for dispensing fluids which when manually operated to dispense product generates small amounts of electrical energy in an electrical generator, preferably for storage in a storage device and to be utilized for various purposes including preferably those for wired or wireless communication links such as preferably those which will communicate with a remote computer as by Wi-Fi and Bluetooth.

Another object is to provide a dispensing apparatus preferably for dispensing fluids which when operated to dispense product generates electrical energy and the electrical energy generated is measured to estimate the amount of fluid dispensed.

An object of the present invention is to provide a method and apparatus for generating ozone containing fluids, preferably, as a foam in small amounts as suitable for use in dispensing from, for example, wall mounted hand cleaning fluid dispensers.

Another object is to provide a novel arrangement for a pump assembly, preferably one adapted to generate ozone with an air compartment within the pump.

The present invention provides a dispensing apparatus including a product dispenser in which product is dispensed by manual movement of an activation mechanism as, for example, by moving a lever with a person's hand, arm or foot. The dispensing apparatus includes an electrical generator for generating electrical energy as a result of the manual movement of the activation mechanism. The nature of the electrical generator is not limited. Mechanical generators may be used which convert mechanical energy into electrical energy, preferably by electromagnetic induction. Generators which provide energy by electrochemistry may also be used. Generators which provide energy by piezoelectric effect may be used.

As one preferred electrical generator, movement of the activation mechanism moves a magnetized element relative a wire coil to generate electrical power. As another electrical generator, movement of the activation mechanism moves fluid product to be dispensed through a fuel cell to provide electrical energy. As another electrical generator, movement of the activation mechanism applies mechanical stress or strain which by piezoelectric effect is converted into electrical energy. For example, a piezoelectric element such as a piezoceramic may be attached to a spring member such that when the spring member is deflected in manual operation of the dispenser the piezoceramic element is compressed, expanded or bent and electric potential is created across electrodes of the element to generate electrical energy.

The electrical energy from the generator may be utilized for many different purposes, without limitation. The electrical energy generated may be used virtually simultaneously although is preferably accumulated in a storage device to store electrical energy. Preferred uses for the electrical energy generated includes without limitation one or more of the following: to power a communication unit; for estimating the amount of fluid dispensed; and to generate ozone. Preferred dispensing apparatus include an electrical generator and one or more of a communication unit, a system for estimating the amount of fluid dispensed and a system to generate ozone.

As one preferred usage the energy may be utilized in the dispensing apparatus to power a data communication unit for receiving information about the product dispenser and transmitting the information to a receiver, preferably but not necessarily wirelessly. Preferably, electrically powered components of the apparatus including the communication unit, any controller, processor and any sensors for detecting information about the apparatus and providing it to the communication unit will have small electrical power requirements.

The present invention also provides a combination of a manually operated fluid dispenser using manual energy to dispense fluid from a reservoir and an electrochemical cell to produce the electric energy, in which the electric energy is derived from chemical conversion of the fluid to be dispensed, and used for example to power a communications unit to transmit information about the dispensing apparatus, preferably wirelessly. The fluid is to be dispensed for use in a purpose other than providing the electrical energy for dispensing. Thus, for example, the fuel after dispensing is for use as a cleaning or a disinfectant solution. The fluid contains suitable compounds, such as, alcohol compounds, which can be chemically converted into electrochemical cells to produce current flow between the electrodes.

The present invention also provides in a fluid dispenser which in operation to dispense fluid generates electrical energy, the improvement in which the electrical energy produced is measured and the resultant measure is used to estimate the amount of fluid dispensed. For example, in the context of a manually operated fluid dispenser with a lever to move a piston of a piston pump to dispense fluid, the extent to which and the manner in which the lever is moved bears a relationship to the volume of fluid dispensed. The extent to which and the manner in which the lever is moved also bears a relationship to the electrical energy generated. Therefore from the electrical energy generated in dispensing an estimate of the fluid dispensed can be made.

In one aspect, the present invention provides a dispensing apparatus comprising:

a product containing reservoir, a dispensing mechanism which on activation causes the product to be discharged from the reservoir, an activation mechanism for activation of the dispensing mechanism by the engagement by a user moving the activation-mechanism, characterized by:

an electrical generator for generating electric energy, the electrical generator coupled to the activation-mechanism such that on movement of the activation-mechanism the generator generates electrical energy.

Preferably, the dispensing apparatus includes one or more of:

(a) an electrical storage device coupled to the generator to store electrical energy generated by the generator, (b) a dispenser sensor unit in said dispenser for detecting information about the dispensing apparatus, a data communications unit in communication with said dispenser sensor unit and configured for receiving information from said dispenser sensor unit, and the transmitting information, (c) a control mechanism that estimates as a function of the electrical energy generated by the generator the amount of fluid dispensed, and (d) an ozone generator to create ozone in air to be discharged with the fluid.

Another aspect of the present invention provides a fluid dispensing apparatus comprising:

a fluid containing reservoir, the reservoir having an outlet opening, a dispensing mechanism which on activation causes fluid from the reservoir to be discharged from the outlet opening to a discharge outlet, an activation mechanism for activation of the dispensing mechanism by the engagement by a user moving the activation mechanism from a first position to a second position, an electrical generator for generating electric energy, the electrical generator generating electrical energy as a result of manual movement of the activation mechanically preferably the electrical generator selected from the group consisting of: an electromagnetic generator coupled to the activation mechanism such that on movement of the activation mechanism from the first position to a second position a magnetized member moves relative a coil member to generate electrical power, a piezoelectric generator with a member which is compressed, expanded or bent on movement of the activation mechanism, and a fuel cell coupled to the activation mechanism such that on movement of the activation mechanism from the first position to the second position, the fluid to be dispensed flows through the fuel cell, and preferably an electrical storage device coupled to the generator to store electrical energy generated by the generator.

In another aspect the present invention provides a fluid dispensing apparatus comprising:

a fluid containing reservoir, a dispensing mechanism which on activation causes fluid to be discharged from the reservoir, an activation mechanism for activation of the dispensing mechanism by movement of the activation mechanism, the activation mechanism adapted for engagement by a user to move the activation mechanism, an electrical generator for generating electric energy, the electrical generator coupled to the activation-mechanism such that on movement of the activation-mechanism to activate the dispensing mechanism the generator generates electrical energy, a control mechanism which:

a. measures at least one feature of the energy generated to produce a measured result, which feature is selected from the group consisting of a feature of the current of the energy generated, a feature of the voltage of the energy generated, a feature of the energy generated and combinations thereof, and b. estimates as a function of said measured result for the feature an estimated amount of fluid discharged.

In another aspect the present invention provides a method of operation of a fluid dispensing apparatus, the fluid dispensing apparatus comprising:

a fluid containing reservoir, a dispensing mechanism which on activation causes fluid to be discharged from the reservoir, an activation mechanism for activation of the dispensing mechanism by movement of the activation mechanism, the activation mechanism adapted for engagement by a user to move activation mechanism, an electrical generator for generating electric energy, the electrical generator coupled to the activation-mechanism such that on movement of the activation-mechanism the generator generates electrical energy, the method comprising the steps of:

(a) moving the activation-mechanism by the to discharge fluid with the dispensing apparatus and to generate electrical energy with the generator:

(b) measuring at least one feature of the energy generated to produce a measured result, which feature is selected from the group consisting of a feature of the current of the energy generated, a feature of the voltage of the energy generated, a feature of the energy generated and combinations thereof, (c) estimating as a function of said measured result for the feature an estimated amount of fluid discharged.

In another aspect, the present invention provides a method of generating ozone containing fluid comprising:

drawing atmospheric air into an air compartment, generating ozone within the air compartment from air in the air compartment by conversion within the compartment of oxygen in the air within the compartment into ozone to form ozonated air, discharging the ozonated air from the air compartment, mixing the ozonated discharged air with a flowable fluid to form an ozonated fluid-air mixture, and passing the ozonated fluid-air mixture out a discharge outlet.

In another aspect, the present invention provides a method of generating ozone containing fluid comprising:

providing a pump having an air compartment, operating the pump in a cycle of operation including the steps of drawing atmospheric air into the air compartment and discharging air from the air compartment, generating ozone within the air compartment from air in the air compartment by conversion within the air compartment of oxygen in the air within the air compartment into ozone to form ozonated air in the air compartment, mixing the ozonated air with a flowable fluid to form an ozonated fluid-air mixture, and passing the ozonated fluid-air mixture out a discharge outlet.

Preferably, the method involves generating ozone within the air compartment by radiating air in the compartment with radiation adequate to convert the oxygen into ozone. Preferably, the radiation is ultraviolet radiation and the step of generating ozone creates an initial ozone concentration in the air in the compartment of at least 0.1% immediately after creating the ozone, more preferably, with the initial ozone concentration to be in the range of 0.05% to 5%. Preferably, the liquid is capable of foaming and the method includes passing the ozonated air and flowable fluid simultaneously through a foam generator to generate foam for discharge out of the discharge outlet.

Preferably, the pump has a liquid chamber in communication with a reservoir containing the flowable fluid and the cycle of operation of the pump includes the steps of drawing liquid into the liquid compartment, discharging liquid from the liquid compartment including discharging the liquid from the liquid compartment before mixing the liquid with the ozonated air.

Preferably, the pump comprises a housing and an impeller movable within the housing such as a piston or rotor with the air compartment and liquid compartment formed within the housing between the housing and the impeller. Preferably, the impeller is movable relative the housing in a cycle of operation in which the air compartment has a variable volume which changes from a minimum volume to a maximum volume and with the step of generating ozone in each cycle including generating ozone when the volume of the air compartment is proximate its maximum. Preferably, the pump may be selected from a piston pump and a rotary displacement pump.

Preferably, the air compartment is defined at least in part by a wall of the housing which transmits ultraviolet radiation and the method includes passing ultraviolet radiation through the wall into the air compartment to irradiate air in the air compartment with radiation adequate to convert the oxygen in the air into ozone.

Preferably, the method includes controlling the generation of ozone in the air chamber such that if a predetermined period of time passes after last generation of ozone without discharge of air from the air compartment, then additional ozone is generated within the air compartment as to compensate for natural decomposition of the ozone into oxygen.

In another aspect, the present invention provides a hand cleaner dispenser dispensing ozone containing fluid onto a user's hand comprising:

a fluid containing reservoir, a pump mechanism including a housing and an impeller movable within the housing, an air compartment and a liquid compartment formed within the housing between the housing and impeller, the impeller movable relative the housing in a cycle of operation (a) to successively draw atmospheric air into the air compartment and discharge air from the air compartment and (b) to successively draw liquid from the reservoir into the liquid compartment and discharge liquid from the liquid compartment, the air compartment defined at least in part by a wail of the housing which is transmits ultraviolet radiation, an emitter of ultraviolet radiation when activated directs ultraviolet radiation through the wall into the air compartment to irradiate air in the air compartment with ultraviolet radiation adequate to convert oxygen in the air in the air compartment into ozone forming ozonated air, and a mixing chamber for simultaneous passage of ozonated air which has been discharged from the air compartment and fluid which has been discharged from the liquid compartment.

Preferably, the pump mechanism is selected from a piston pump and a rotary displacement pump.

Where the pump is a piston pump, a preferred arrangement is with the piston pump attached to a fluid containing reservoir with the air compartment provided to be external of the reservoir with a wall of the housing forming the air compartment being accessible to provide for a radiation of air within the air compartment via an ultraviolet emitter. To provide for increased volume of the air chamber, the air chamber can advantageously be provided to have a diameter which is greater than a diameter of an outlet from the fluid containing reservoir.

A dispensing assembly to produce ozone may optionally be manually operated and in which electrical energy to create the ozone may be supplied by an electrical generator manually operated to dispense fluid. The ozone producing assembly may optionally include a communication unit and/or a system for estimating the volume of fluid dispensed.

In another aspect, the present invention provides a dispenser dispensing ozone containing foam comprising:

an ozone generator comprising an ozone generating chamber, the ozone generating chamber having an air inlet in communication with a source of air and an outlet, an ozone generator within the ozone generating chamber to generate ozone from air in the ozone generating chamber by conversion within the ozone generating chamber of oxygen in the air within the ozone generating chamber into ozone to form ozonated air, a fluid containing reservoir containing a fluid capable of foaming, a liquid pump, an air pump, the air pump comprising a piston pump having a piston-forming element reciprocally coaxially slidable within a piston chamber-forming member in which an air compartment is formed between the piston-forming element and the piston chamber-forming member, the piston-forming element reciprocally movable relative the piston chamber-forming member in a cycle of operation between a retracted position and an extended position, the air compartment having a variable volume which changes from a minimum volume to a maximum volume, the volume of the air compartment being at the maximum volume when the piston-forming element is in a first position of the retracted position and the extended position, the volume of the air compartment being at the minimum volume when the piston-forming element is in a second position of the retracted position and the extended position different than the first position, the outlet of the ozone generating chamber in communication with an ozone inlet to the air compartment, the piston-forming element movable relative the housing in a cycle of operation to draw ozonated air from the chamber into the air compartment and discharge ozonated air from the air compartment, the liquid pump operative to draw liquid from the reservoir and discharge liquid, a foam generator for simultaneous passage of ozonated air which has been discharged from the air compartment and fluid which has been discharged from the liquid pump to generate foam for discharge out a discharge outlet, wherein the operation of the air pump is controlled such that a rest period is provided between successive cycles of operation during which rest period the piston-forming element is not moved and optionally the piston-forming element is maintained in the second position.

In another aspect, the present invention provides a dispenser dispensing ozone containing foam comprising:

an ozone generator comprising an ozone generating chamber, the ozone generating chamber having an air inlet in communication with a source of air and an outlet, an ozone generator within the ozone generating chamber to generate ozone from air in the ozone generating chamber by conversion within the ozone generating chamber of oxygen in the air within the ozone generating chamber into ozone to form ozonated air, a fluid containing reservoir containing a fluid capable of foaming, a liquid pump, an air pump, the air pump comprising a piston pump having a piston-forming element reciprocally coaxially slidable within a piston chamber-forming member in which an air compartment is formed between the piston-forming element and the piston chamber-forming member, the piston-forming element reciprocally movable relative the piston chamber-forming member in a cycle of operation between a retracted position and an extended position, the air compartment having a variable volume which changes from a minimum volume to a maximum volume, the volume of the air compartment being at the maximum volume when the piston-forming element is in a first position of the retracted position and the extended position, the volume of the air compartment being at the minimum volume when the piston-forming element is in a second position of the retracted position and the extended position different than the first position, the outlet of the ozone generating chamber in communication with an ozone inlet to the air compartment, the piston-forming element movable relative the housing in a cycle of operation to draw ozonated air from the chamber into the air compartment and discharge ozonated air from the air compartment, the liquid pump operative to draw liquid from the reservoir and discharge liquid, a foam generator for simultaneous passage of ozonated air which has been discharged from the air compartment and fluid which has been discharged from the liquid pump to generate foam for discharge out a discharge outlet, an ozone charging stroke is defined as movement from the second position to the first position and an ozone discharging stroke is defined as movement from the first position to the second position, the operation of the ozone generator is controlled such that an amount of ozone required for each cycle of operation of the air pump is substantially generated by the ozone generator during that cycle of operation and a portion of the rest period immediately preceding that cycle of operation, and optionally the operation of the ozone generator is controlled such that initiating the generation of ozone is initiated in the ozone generator at a time prior to commencement the charging stroke.

In a further aspect, the present invention provides a dispenser dispensing ozone containing foam comprising:

an ozone generator comprising an ozone generating chamber, the ozone generating chamber having an air inlet in communication with a source of air and an outlet, an ozone generator within the ozone generating chamber to generate ozone from air in the ozone generating chamber by conversion within the ozone generating chamber of oxygen in the air within the ozone generating chamber into ozone to form ozonated air, a fluid containing reservoir containing a fluid capable of foaming, a liquid pump, an air pump, the air pump comprising a piston pump having a piston-forming element reciprocally coaxially slidable within a piston chamber-forming member in which an air compartment is formed between the piston-forming element and the piston chamber-forming member, the piston-forming element reciprocally movable relative the piston chamber-forming member in a cycle of operation between a retracted position and an extended position, the air compartment having a variable volume which changes from a minimum volume to a maximum volume, the volume of the air compartment being at the maximum volume when the piston-forming element is in a first position of the retracted position and the extended position, the volume of the air compartment being at the minimum volume when the piston-forming element is in a second position of the retracted position and the extended position different than the first position, the outlet of the ozone generating chamber in communication with an ozone inlet to the air compartment, the piston-forming element movable relative the housing in a cycle of operation to draw ozonated air from the chamber into the air compartment and discharge ozonated air from the air compartment, the liquid pump operative to draw liquid from the reservoir and discharge liquid, a foam generator for simultaneous passage of ozonated air which has been discharged from the air compartment and fluid which has been discharged from the liquid pump to generate foam for discharge out a discharge outlet, an ozone charging stroke is defined as movement from the second position to the first position and an ozone discharging stroke is defined as movement from the first position to the second position, the operation of the ozone generator is controlled such that a volume of ozonated air required for at least one cycle of operation of the air pump is maintained within the ozone chamber at all times prior to a charging stroke with an ozone concentration which meets a desired limit by controlling the operation ozone generator to generate ozone during cycles of operation and rest periods when either an ozone sensor indicates that the concentration of ozone in the ozone generating chamber is below a desired level, or a controller for the dispenser indicates that additional ozone is required by the controller estimating the ozone in the ozone chamber by monitoring one or more of the time of and number of cycles of the air pump over time, the time of and amount of ozone generated over time, and the time of and amount of ozone decayed to oxygen with time.

BRIEF DESCRIPTION OF THE DRAWINGS

Further aspects and advantages of the present invention will be apparent from the following description taken together with the accompanying drawings in which.

DETAILED DESCRIPTION OF THE DRAWINGS

Figure 1:
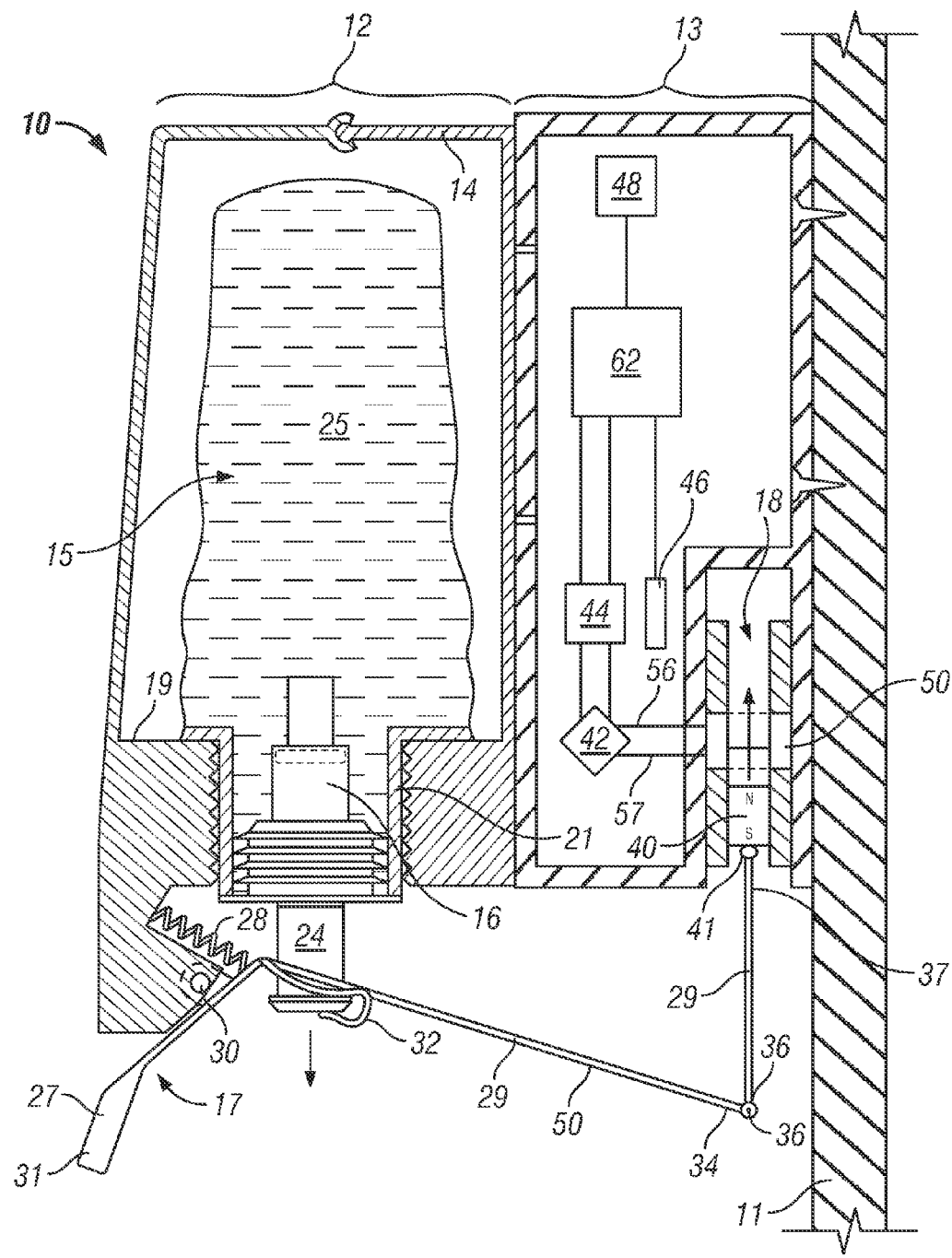
FIG. 1 is a partially cut-away side view of a first preferred embodiment of a fluid dispenser in accordance with the first aspect of the present invention as mounted to a wall with an actuator lever in a forward rest position and showing a first embodiment of an electrical generator.
Figure 2:
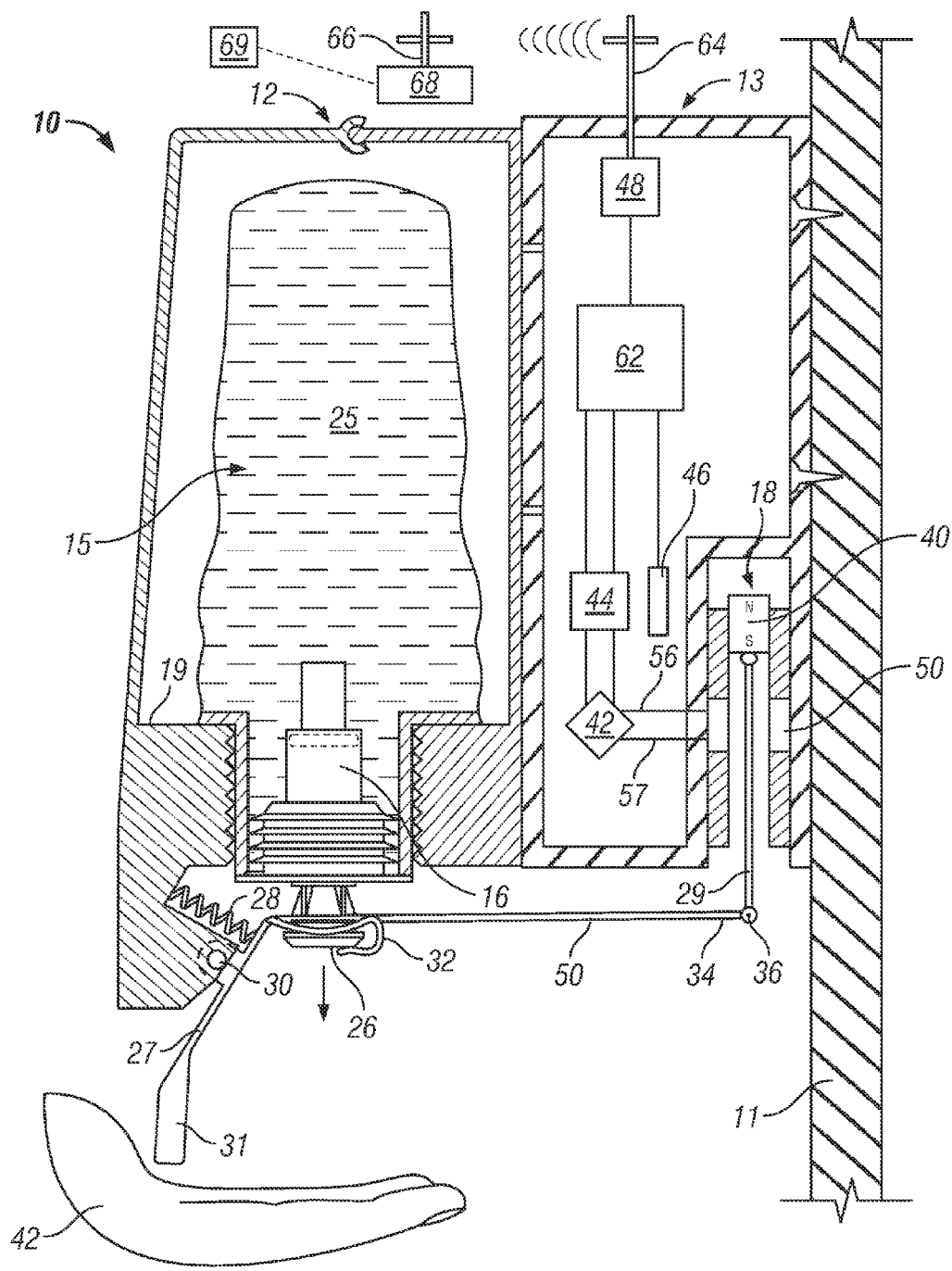
FIG. 2 is a side view the same as FIG. 1 but showing the actuator lever in a rear position.

Reference is made to FIGS. 1 and 2 which show a dispenser assembly 10 mounted to a wall 11. The dispenser assembly 10 includes a dispenser 12 and a back housing 13. The dispenser 12 includes a front housing 14 which carries and supports a reservoir bottle 15, a pump assembly 16 and a lever assembly 17. The dispenser 12 is mounted via its front housing 14 to the front of the back housing 13 and the back housing 13 is mounted to the wall 11.

The dispenser 12 comprises a manually operated fluid dispenser substantially the same as that disclosed in the applicant's U.S. Pat. No. 5,489,044 to Ophardt issued Feb. 6, 1996, the disclosure of which is incorporated herein by reference. The back housing 13 is shown to schematically carry an electrical generator 18 as well as an electrical storage device 44 coupled to the generator 18 to store electrical power generated by the generator 18, a controller 62, a dispenser sensor unit 46 for detecting information about the dispenser 12, and a data communications unit 48 in communication with the dispenser unit 46 and configured for receiving information from the dispenser sensor unit 46 and for transmitting information.

The front housing 14 is shown to have a bottom support plate 19 to receive and support the bottle 15 and the pump assembly 16. The support plate 19 has a circular opening therethrough. The bottle 15 sits supported on the support plate 19 with a neck 21 of the bottle extending through the opening and secured in the opening as by friction fit.

Figure 3:
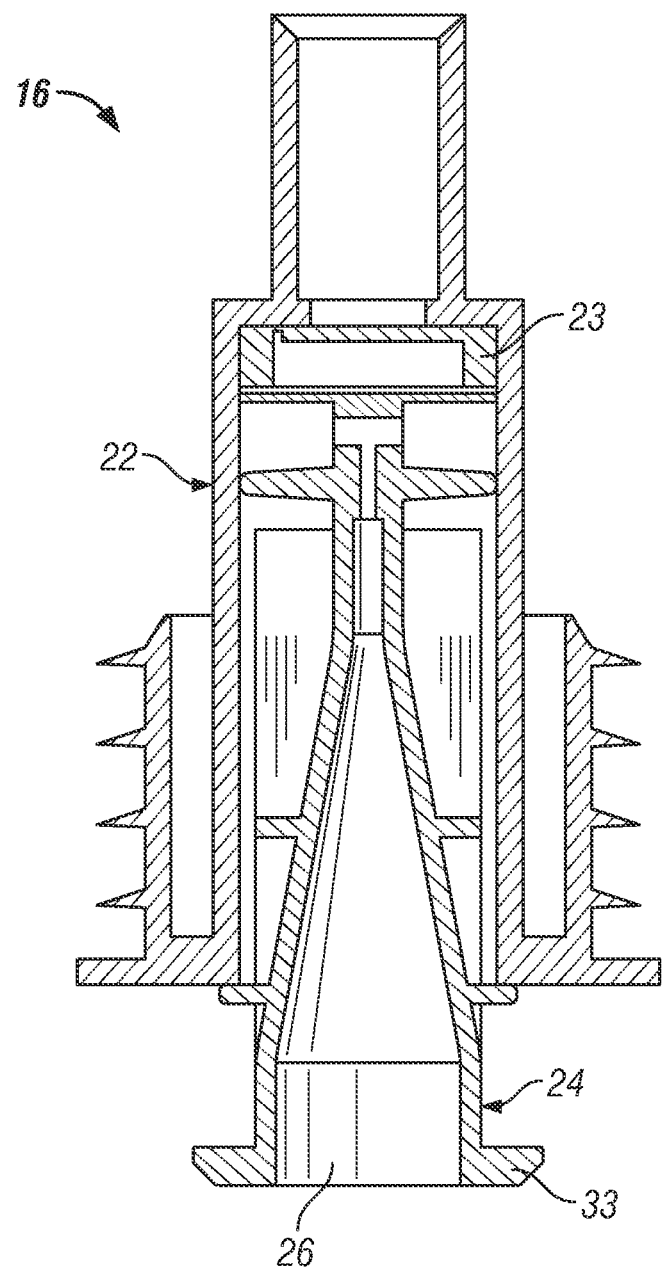
FIG. 3 is a cross-sectional side view of the pump assembly in the fluid dispenser shown in FIG. 1.

The pump assembly 16 has a construction as illustrated in FIG. 3 as taught, for example, in U.S. Pat. No. 5,489,044 to Ophardt, issued Feb. 6, 1996, the disclosure of which is incorporated herein by reference. The pump assembly 16 includes a piston chamber-forming member 22 secured in the neck 21 of the bottle 15. The piston chamber-forming member 22 carries a one-way valve member 23 and an axially reciprocal piston member 24 such that in a known manner reciprocal axial movement of the piston member 24 within the piston chamber-forming, member 22 will dispense fluid 25 within the bottle 15 out a discharge outlet 26 of the piston member 24.

The front housing 14 carries a lever assembly 17 which includes an activating lever 27, a spring 28, and a rigid link 29. The actuating lever 27 is mounted to the bottom support plate 19 for pivoting about a horizontal lever pivot axis 30 with the spring 28 disposed between the bottom support plate 19 and the actuating lever 27 to urge the actuating lever 27 to pivot clockwise as shown.

The actuating lever 27 includes a manual engagement handle 31, a hook member 32 and a rear extension arm 50. The actuating lever 27 carries forward and downward from the pivot axis 30, the manual engagement handle 31 for engagement by a user to move the actuating lever 27 counterclockwise against the bias of the spring 28. The actuating lever 27 carries rearwardly from the lever pivot axis 30 the hook member 32 which engages an engagement flange 33 on the piston member 24 such that with pivoting of the actuating lever 27 to different positions about the lever pivot axis 30, the piston member 24 slides axially within the piston chamber-forming member 22. The actuating lever 27 carries the extension arm 50 so as to extend rearwardly past the hook member 32 to a rear end 34. The rear end 34 is pivotally coupled to the link 29 for relative pivoting about a horizontal link pivot axis 35 at a first end 36 of the link 29. A second end 37 of the link 29 is pivotally connected to a lower first end of a magnet 40 for relative pivoting about a second horizontal link pivot axis 41.

Reference is made to FIG. 1 which shows the pump assembly 16 with its piston member 24 in an extended position as biased to this position by reason of the actuating lever 27 being biased clockwise by the spring 28. With the dispenser assembly 10 in the rest position as shown in FIG. 1, a user may activate the dispenser 12 preferably by manually urging, with the rear of an upwardly facing palm of a user's hand 42 shown in FIG. 2, the engagement handle 31 rearwardly towards the wall 11 with the palm and fingers under the discharge outlet 26. In such movement, the actuating lever 27 is pivoted counterclockwise relative to the bottom support plate 19 against the bias of the spring 28 with the hook member 32 moving the piston member 24 axially inwardly into the piston chamber-forming member 22 and with the rear end 34 of the extension arm 50 of the actuating lever 27 being moved upwardly moving the link 29 upwardly and sliding the magnet 40 upwardly.

Figure 4:
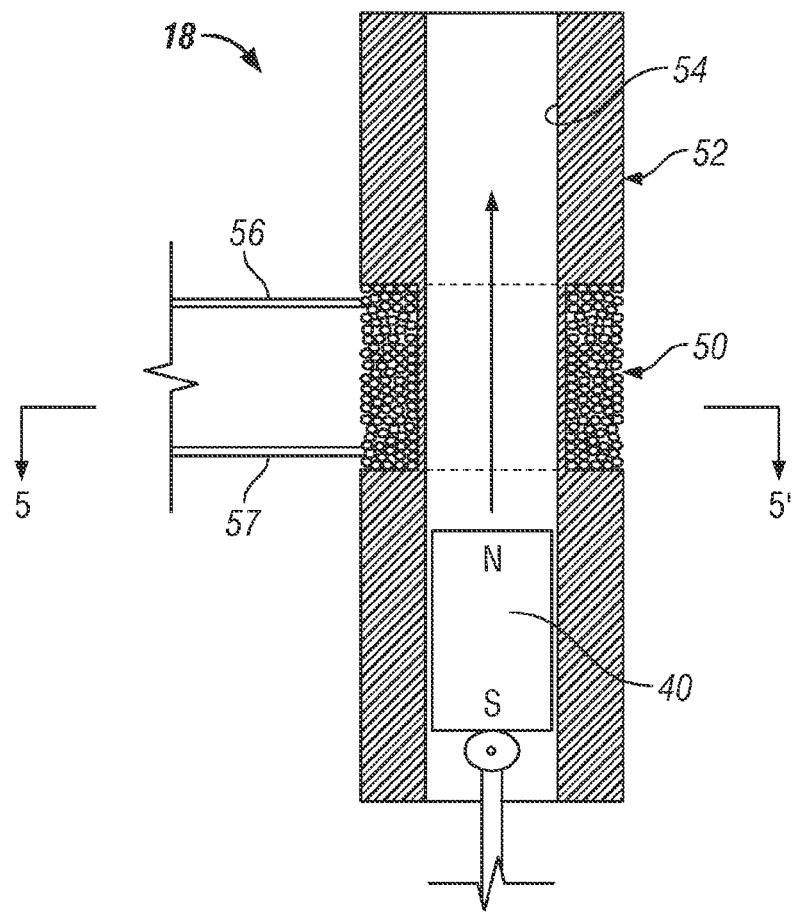
FIG. 4 is an enlarged view of portions of FIG. 1 showing the first embodiment of the electrical generator.
Figure 5:
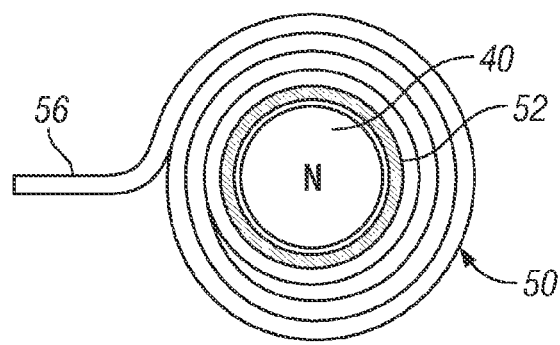
FIG. 5 is a cross-sectional view along section line 5-5 shown in FIG. 4.

The electrical generator 18 includes the magnet 40, a wire coil 50 and a cylindrical slide tube 52. As may be seen from FIGS. 4 and 5, the magnet 40 is shown to be generally cylindrical and coaxially slidable within a cylindrical passageway 54 provided within the slide tube 52. The magnet 40 is a permanent magnet having, as illustrated, a north pole N at one axial end and a south pole S at the other axial end. The wire coil 50 is only schematically shown but comprises a winding of insulated wire, preferably insulated copper wire within an annular groove in the slide tube 52. The wire coil 50 comprises a continuous length of such wire extending from a first end 56 to a second end 57. Electrical energy is generated as by current which moves through the wire when the magnet 40 moves inside the passageway 54 through the wire core 18.

Figure 6:
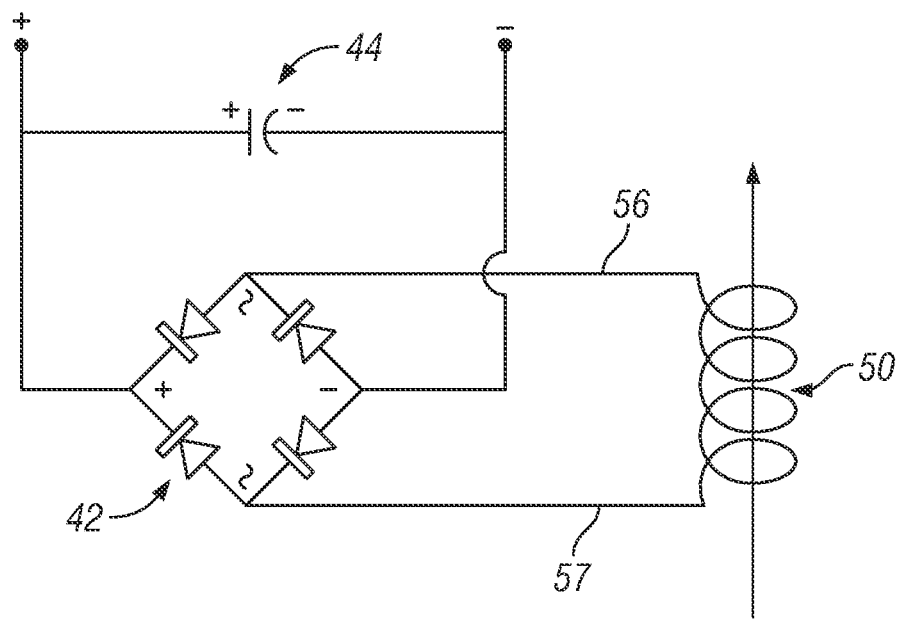
FIG. 6 is a schematic diagram showing an electrical circuit of the dispenser of FIG. 1.
Figure 6:
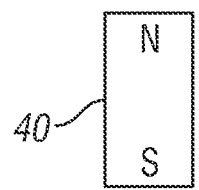

In a cycle of operation of the dispenser assembly 10, the actuating lever 27 is manually moved from the forward rest position in FIG. 1 to the rear position in FIG. 2 and when released by the hand of a user, the actuating lever 27 then returns under the bias of the spring 28 to the forward rest position. In the cycle of movement of the actuating lever 27, as seen by comparing FIGS. 1 and 2, the magnet 40 is moved from a position below the coil 50 through the coil 50 to a position above the coil 50 and then back through the coil 50 to a position below the coil 50. Such cyclical movement of the magnet 40 relative to the coil 50 generates electricity in a manner to be understood by a person skilled in the art and is briefly explained with reference to FIG. 6. FIG. 6 is a schematic diagram illustrating the wire coil 50 as having the ends 56 and 57 of its wire connected to a bridge rectifier 42 which, in turn, is connected with an electrical storage device 44 illustrated in FIG. 6 as being a capacitor. In a simple sense, as the magnet 40 passes through the wire coil 50, a sinusoidal voltage wave is created between the two wires 56 and 57 thus generating an alternating current. Each sinusoidal wave is converted into a pair of positive waves by bridge rectifier 42. These positive waves charge the capacitor 44 which accumulates additional charge with each pass of the magnet 40.

The capacitor 44 is schematically illustrated as providing power to an electronically operated controller 62. The dispenser control unit 46 is only schematically illustrated but in the preferred embodiment is a counter which counts the number of times that the lever 27 is actuated. The counter 46 preferably operates by sensing the change in magnetic field which arises each time the magnet 40 is moved to an upper position and then withdrawn therefrom.

The data communications unit 48 is schematically illustrated in FIGS. 1 and 2 and intended to receive information from the dispenser sensor unit 46, preferably via the controller 62, and to transmit information wirelessly as to a wireless receiver 68. The controller 62 is schematically illustrated as receiving power from the electrical storage device 44 and coupling the dispenser sensor unit 46 and the data communication unit 48 for exchange of information and for powering of each for their operation. FIG. 2 schematically shows the data dispensing unit 48 as having an antenna 64 for transmitting information wirelessly to the antenna 66 of a remote wireless receiver 68 only schematically shown. The receiver 68 preferably also comprises a wireless hub interconnecting with a computer 69 that preferably employs a web browser for viewing information sent via the hub.

The embodiment of FIGS. 1 and 2 illustrates the dispenser 12 as comprising a separate unit from the back housing 13. This arrangement can be advantageous so as to modify an existing manual dispenser 12 by providing a suitable back housing 13 and modifying the actuating lever 27 of the housing 14 so as to provide the rear extension arm 50 to the actuating lever 27. In this manner, a known existing manual dispenser 12 may be retrofitted by coupling a suitable back housing 13 thereto and provide a combination in which there is a capability of transmitting information preferably wirelessly. In an alternate arrangement, the front housing 14 and the back housing 13 may be combined so as to provide in a single housing the capability of transmitting information preferably wirelessly. Of course, insofar as there may be a single housing, at the time of manufacture, a selection can be made as to whether or not the manual dispenser 12 may or may not be provided with all the components necessary for providing transmission of information.

Figure 7:
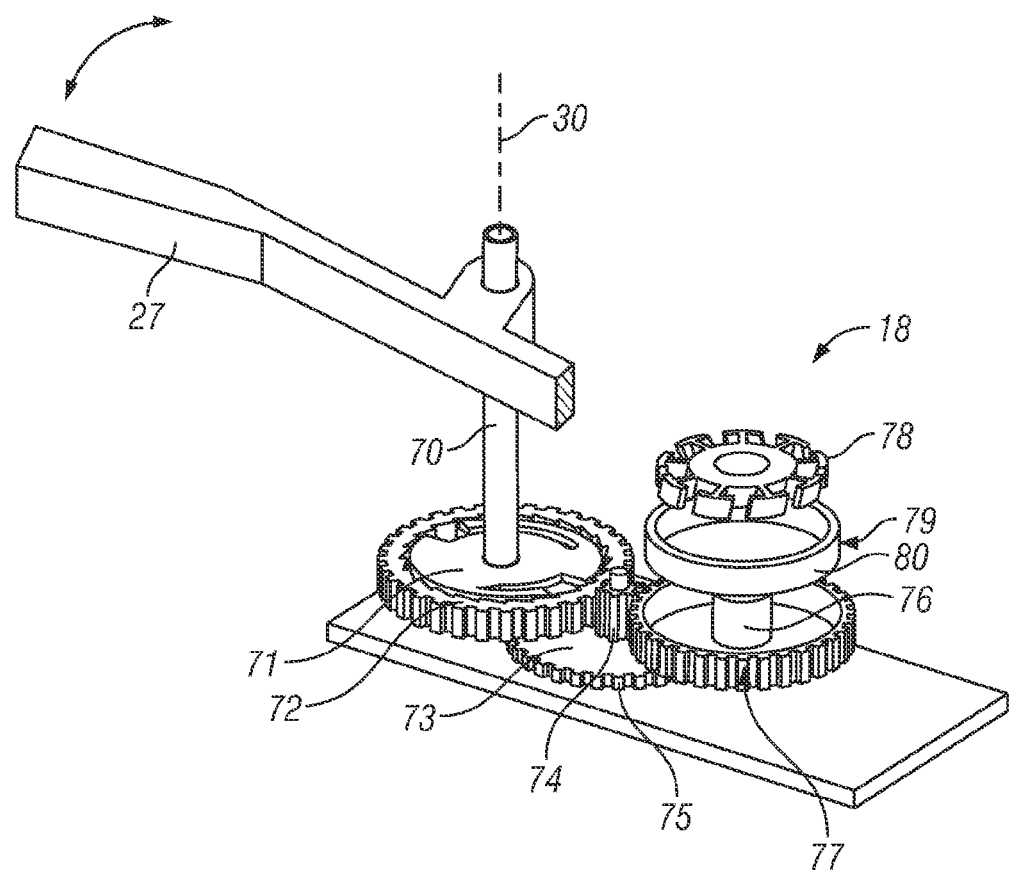
FIG. 7 is a schematic pictorial view of a second embodiment of an electrical generator mechanism coupled to the actuator lever of FIG. 1.

Reference is made to FIG. 7 which schematically illustrates a second embodiment of an electrical generator 18 coupled to the actuating lever 27. In FIG. 7, the actuating lever 27 is only partially shown. The actuating lever 27 is pivotable about the pivot axis 30 with activating lever 27 fixedly secured to an axle member 70. The axle member 70 rotates a one-way clutch 71 which rotates an input gear 72 which transfers motion to an intermediate gear 73. The intermediate gear 73 receives motion from the input gear 71 via a small diameter wheel 74 and transfers motions from the input gear 71 to an alternator assembly 77 via a large diameter gear 75 which meshes with a small diameter rotor gear, not clearly shown on the bottom of a rotor 79 of the alternator assembly 77. The rotor 79 is in the form of a flattened cup with a downwardly extending boss and with the small diameter rotor gear mounted on this boss. The intermediate gear 73 transfers motions from the input gear 72 to the alternator assembly 77 and, at the same time, increases the relatively low speed input from the input gear to a higher speed output. The alternator rotor 79 has mounted therein magnetic segments 80 which provide the rotor poles. An alternator stator 78 carries on its radial arms copper windings which are not shown. The alternator preferably uses a three phase stator winding with nine stator teeth and twelve rotor pulls making in total six pull pairs. The stator 76 is preferably made up of a number of laminations of thin steel. In a known manner, with rotation of the rotor 79 relative the stator 78 electrical energy is generated. The output from the alternator assembly is taken to a rectification module, not shown, which houses a three phase rectifier which converts the three phase alternating current power output from the alternator assembly to direct current. The output from the rectification module is supplied to a storage device to accept energy in electronic format.

Figure 8:
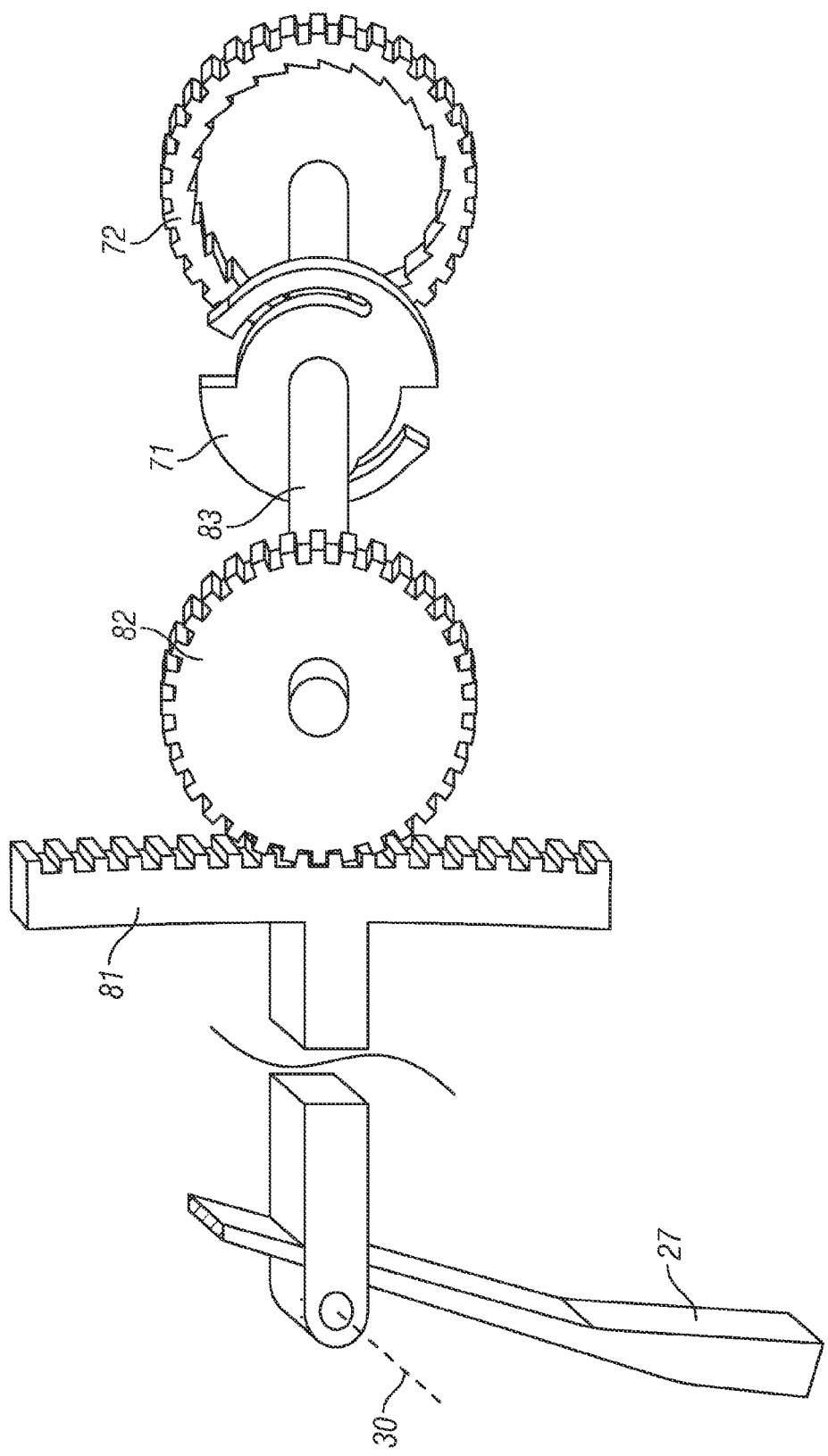
FIG. 8 is a schematic exploded pictorial view showing a second embodiment of a gear train for the electrical generator mechanism of FIG. 7.

Reference is made to FIG. 8 which is a schematic exploded pictorial view showing an alternate manner for connection of the lever 27 to the one-way clutch 71. In FIG. 8, fixedly connected to the lever 27 for pivoting therewith about the axis 30 is a toothed rack 81 for engagement with a rack engaging gear 82 fixedly connected to an axle member 83 upon which the one-way clutch 71 is fixedly engaged. As is the case in both FIGS. 7 and 8, the one-way clutch 71 is adapted to be received coaxially inside the input gear 72 such that rotation of the one-way clutch 71 in a counterclockwise direction rotates the input gear 72, however, rotation of the one-way clutch 72 in the opposite clockwise direction does not rotate the input gear 72. The provision of the one-way clutch 71 as shown in FIGS. 7 and 8 is not necessary and the output from the lever may be connected directly to the input gear 51. Providing the one-way clutch 71 is advantageous insofar as the gearing arrangement provides as in the manner of a fly wheel for continued rotation of the rotor 79 due to the inertia of the rotor and the gear train after initial movement by the lever 27 on a user manually moving the lever and without the need for the spring 28 on returning the lever 27 to the rest position to stop the rotation of the gear train and move the gear train in a reverse direction.

Figure 9:
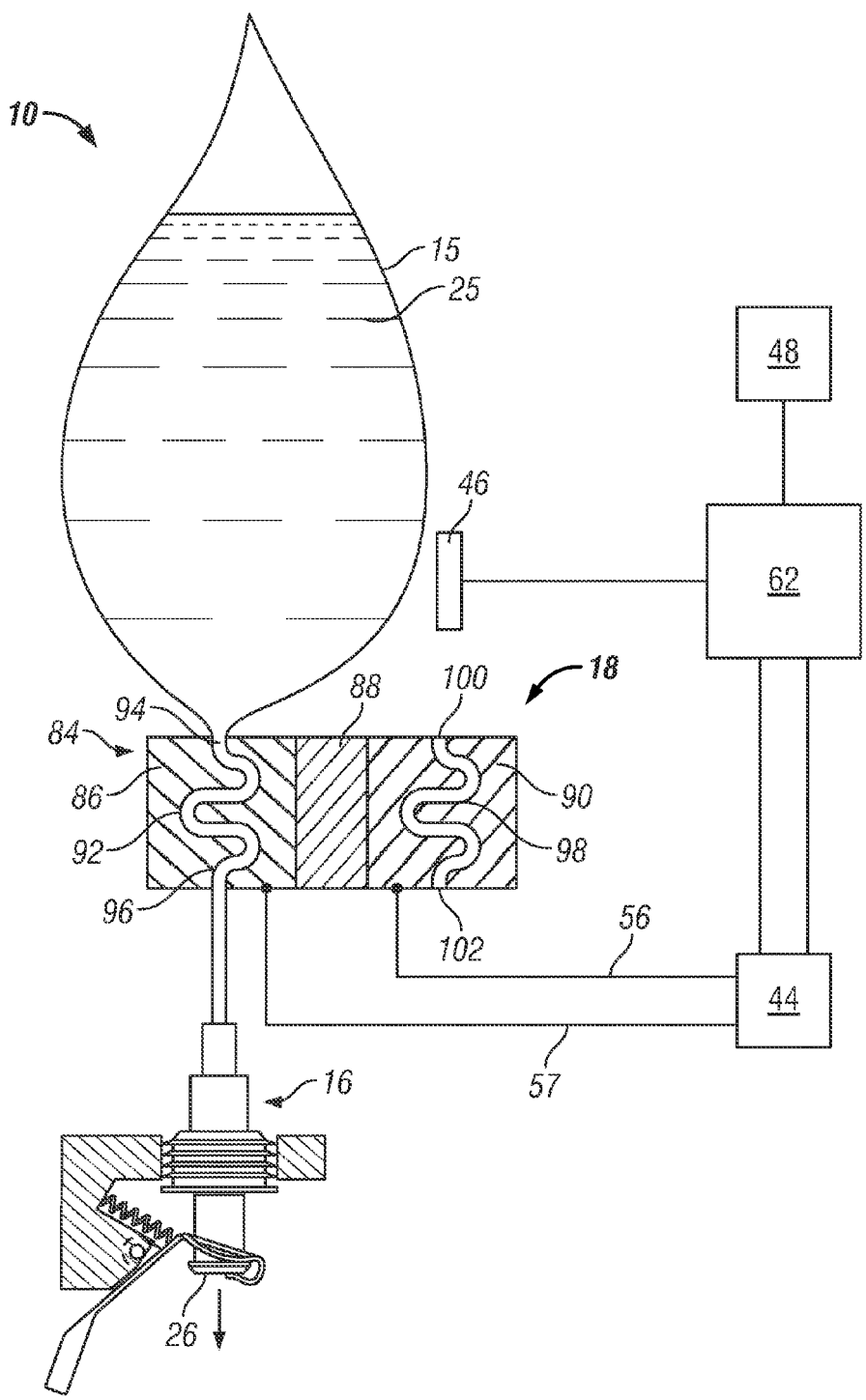
FIG. 9 is a schematic view of a dispensing apparatus in accordance with a third embodiment of this invention using a fuel cell as an electrical generator mechanism.

Reference is made first to FIG. 9 which is a schematic view of a dispenser apparatus 10 in accordance with a third embodiment of the present invention and incorporating as the electric generator 18 a fuel cell 84 open at an outlet. The reservoir 15 has flexible walls 105, preferably made of flexible recyclable plastic sheet material.

The fuel cell 84 comprises a fuel electrode 86, an electrolyte 88 and a non-fuel electrode 90. A fluid passageway 92 extends through the fuel electrode 86 so as to place fluid from the reservoir 15 into communication and contact with the fuel electrode 86. The fluid passageway 92 extends from an inlet 94 to an outlet 96. With the outlet of the reservoir 15 connected to the passageway inlet 94, fluid passes through the fluid passageway 92 to the passageway outlet 96.

A non-fuel passageway 98 extends through the non-fuel electrode 90 to place atmospheric air containing oxygen into communication with the non-fuel electrode and permit water created at the non-fuel electrode to exit the non-fuel passageway 98. The non-filet passageway extends from an inlet 100 to an outlet 102. Air may enter the non-fuel passageway 98 via inlet 100 and, if necessary, water may exit the non-fuel passageway 98 under the influence of gravity via outlet 102.

A manual piston pump assembly 16 similar to that shown in FIG. 1 has an inlet connected to the outlet 96 of the fluid passageway 92. When the pump assembly 16 is operated by a user, fluid is fluid is drawn from the reservoir 10 through the fuel cell 84 via the fluid passageway 92 and discharged for use as, for example, onto a user's hand out of the pump outlet 26.

FIG. 9 schematically shows a simple electrical circuit including a first lead wire 56 connecting the filet electrode 86 to the electrical storage element 44 and a second lead wire 57 connecting the non-fuel electrode 90 and the electrical storage element 44. In known manner with the fuel cell in an operative condition such that the two electrodes are electrically connected across the electrical storage element 44 then current flow between the electrodes will generate electrical energy which may be captured by the electrical storage element 44. The electrical storage element 44 may include suitable control or conversion components to assist in optimizing receipt of electrical energy from the fuel cell 84 as, for example, a control arrangement to render the fuel cell inoperative if additional electrical energy is not at any time required. As in a similar manner to that described with reference to the first embodiment of FIG. 1, the dispensing apparatus 10 includes a controller 62, a dispenser sensor unit 46 for detecting information about the dispenser 12, and a data communications unit 48 in communication with the dispenser unit 46 and configured for receiving information from the dispenser sensor unit 46 and for transmitting information.

In a known manner, the fuel cell whether an acid electrolyte fuel cell or an alkaline electrolyte fuel cell preferably chemically converts components in the fluid at the fuel electrode 86 at the same time that oxygen from the air is consumed at the non-fuel electrode, typically to produce water.

Figure 10:
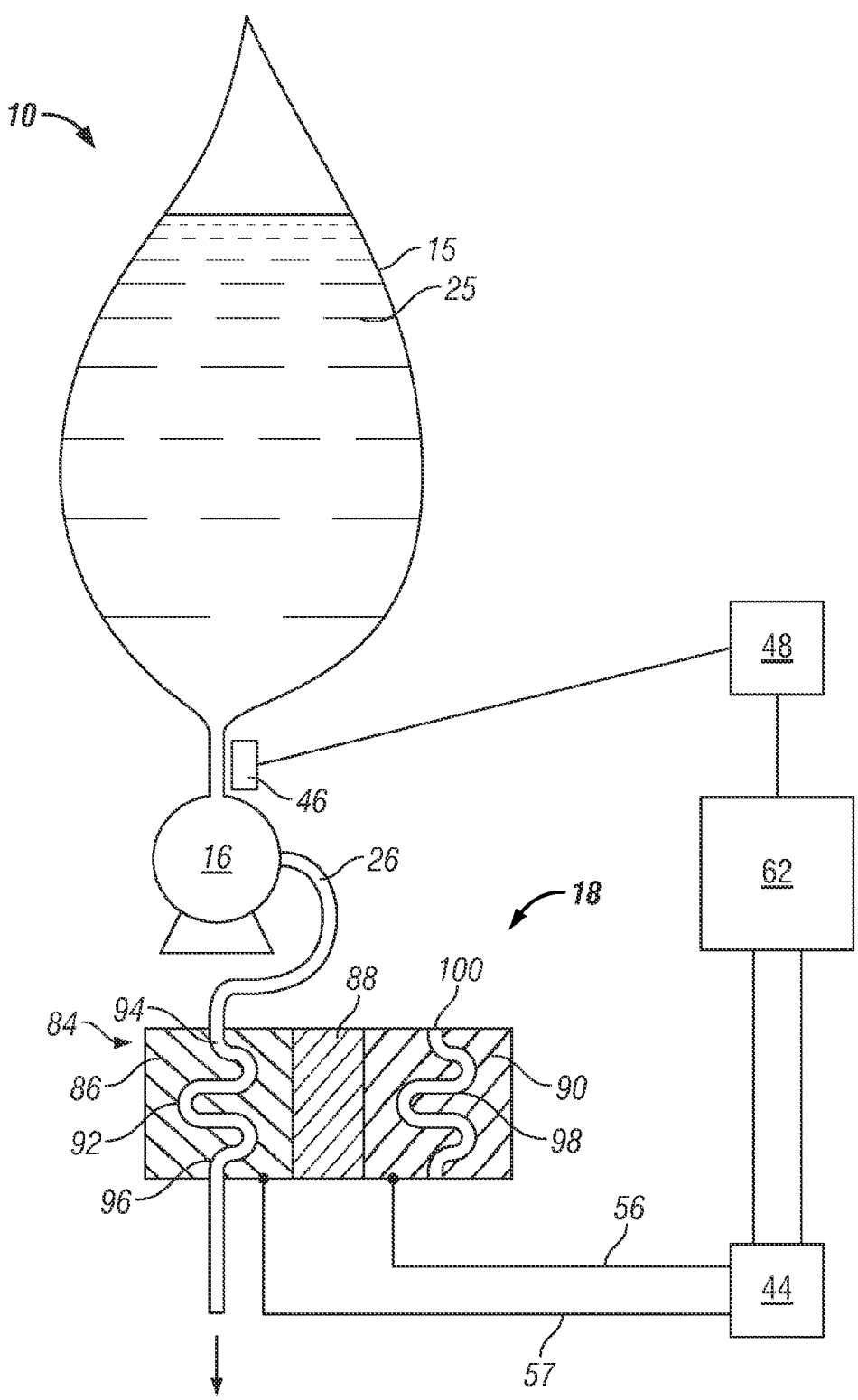
FIG. 10 is a schematic view of a dispensing apparatus in accordance with a fourth embodiment of the present invention using a fuel cell as an electrical generator mechanism.

As contrasted with the embodiments of FIG. 9 in which the fuel cell 84 of the electrical generator 18 is upstream of the pump 16, FIG. 10 shows a fifth embodiment in which the fuel cell 84 is downstream of the manually operated pump 16 with fluid to pass through the fluid passageway 92 in the fuel electrode 86 after exiting the pump outlet 26. The pump 16 is only schematically shown in FIG. 10.

Figure 11:
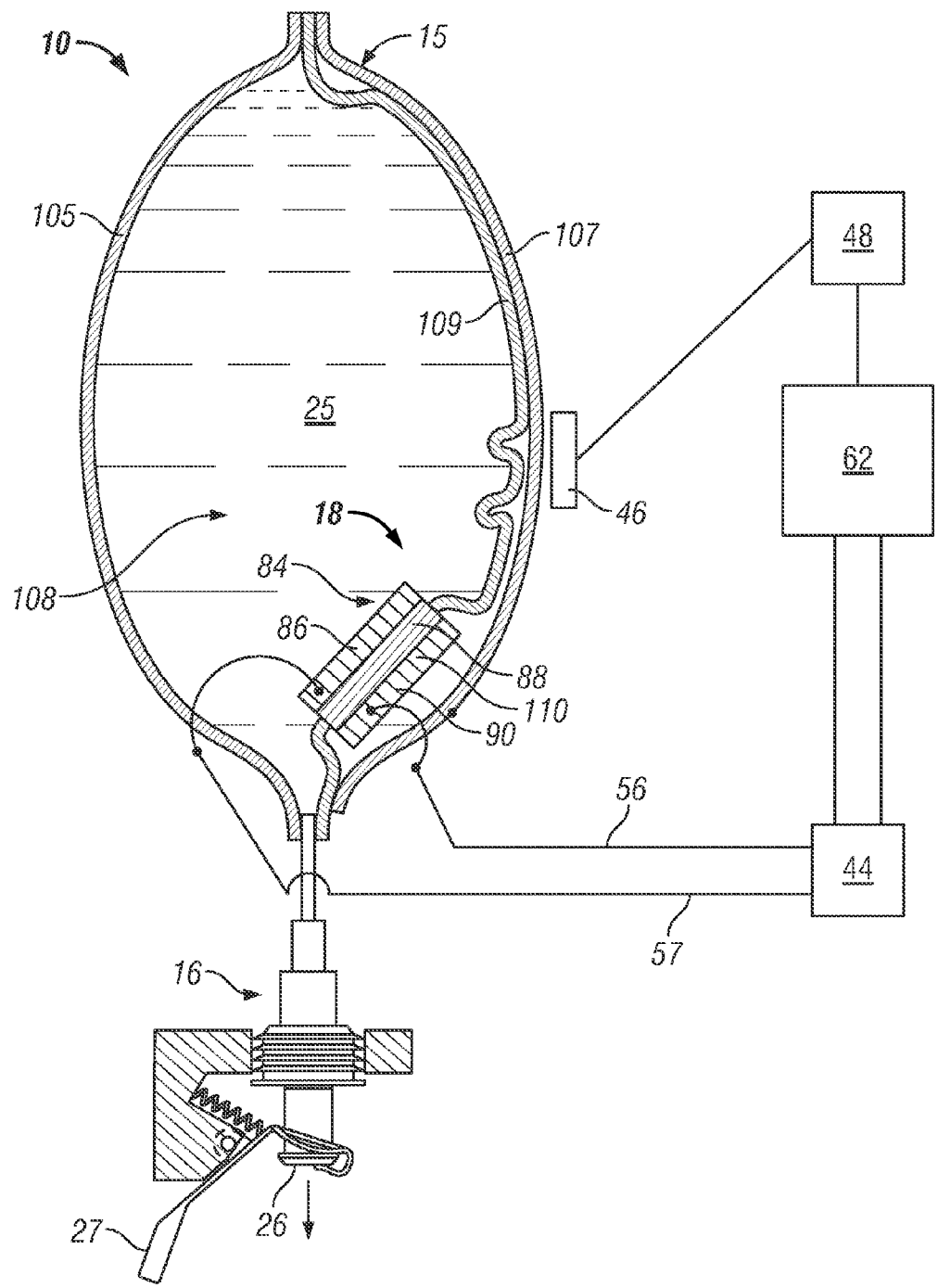
FIG. 11 is a schematic view of a dispensing apparatus in accordance with a fifth embodiment of the present invention using a fuel cell as an electrical generator mechanism.

Reference is made to FIG. 11 which shows another dispensing apparatus 10 in which the electrical generator 18 comprises a fuel cell 84 in accordance with a sixth embodiment of the present invention.

In the embodiment illustrated in FIG. 11, the reservoir 15 comprises a collapsible bag formed of sheet materials and open merely at its outlet. The flexible reservoir 15 is effectively formed with two compartments. The reservoir 10 has two flexible outside walls 105 and 107 and an interior dividing wall 109 also made of the fluid and gas impermeable flexible sheet material. The dividing wall 109 has a central opening therethrough within which there is sealably received a three layer fuel cell 84 comprising membranes comprising a first electrode 86, an electrolyte 88 and a second electrode 90. The dividing wall 109 and the first wall 105 form a first compartment 108 which is filled with fluid 25 such that the fluid 25 is in contact with the first electrode 86. The dividing wall 109 and the second wall 107 form a second compartment 110 open to the second electrode 90. The dividing wall 109 seatably engages one or more of the first electrode 86, electrolyte 88 and second electrode 90 so as to provide the first compartment 108 sealed from the second compartment 110. The first compartment 108 is initially filled with fluid and will collapse on the fluid being dispensed. The second compartment 110 is initially collapsed and is intended to receive and become expanded by the generation of gas at the second electrode 90 with chemical conversion of the fluid. Separating the gas in the second compartment from the fluid 25 in the first compartment 108 can be advantageous to ensure that the presence of gas in the fluid 25 does not impair the operation of the cell in producing electricity.

With the initial volume of the fluid placed in the reservoir bag to fill the bag, the bag may be sized to provide for adequate additional space, if necessary, to accommodate gases which may be produced. Creation of gas pressure within the reservoir 15 can assist in the expelling of fluid from the reservoir.

One preferred fluid for use as fuel is a fluid containing alcohol compounds, most preferably, ethanol which is also known as ethyl alcohol.

Alcohol compounds may be selected from the group comprising a methyl alcohol (also known as methanol), ethyl alcohol, propyl alcohol, isopropyl alcohol (also known as isopropanol), butyl alcohol, isobutyl alcohol, sec-butyl alcohol, tert-butyl alcohol, 1-pentanol, 1-hexanol, ethylene propylene glycol, glycerol (also known as glycerine) and benzyl alcohol. Preferred such alcohol compounds may be those which are non-toxic and have lower flammability. Commercially available disinfectants and cleaners are known which comprise substantial portions of such alcohol compounds. For example, Gojo Industries of Akron, Ohio, has a product by the name "Purell" (trade name) instant hand sanitizer dry hands formula which is a liquid and includes about 62% of ethanol, in the range of about 10% of isopropanol and about 3% of glycerin. Other useful fluids as a fuel would be water/ethanol mixtures that are effectively equivalent to automotive windshield wiper fluids. Other fluids which would be useful include alcohol beverages for liquid consumption such as vodka which has a sufficiently high alcohol content.

The fuel cell may be an acid electrolyte fuel cell with the fuel being chemically converted to release hydrogen ions which pass through the electrolyte to the non-fuel electrode which then combined with oxygen to form water at the non-fuel electrode and by which electrons flow between the non-fuel electrode and the fuel electrode. However, the fuel cell could also function as an alkaline electrolytic cell with hydroxy ions to pass through the electrolyte.

Figure 12:
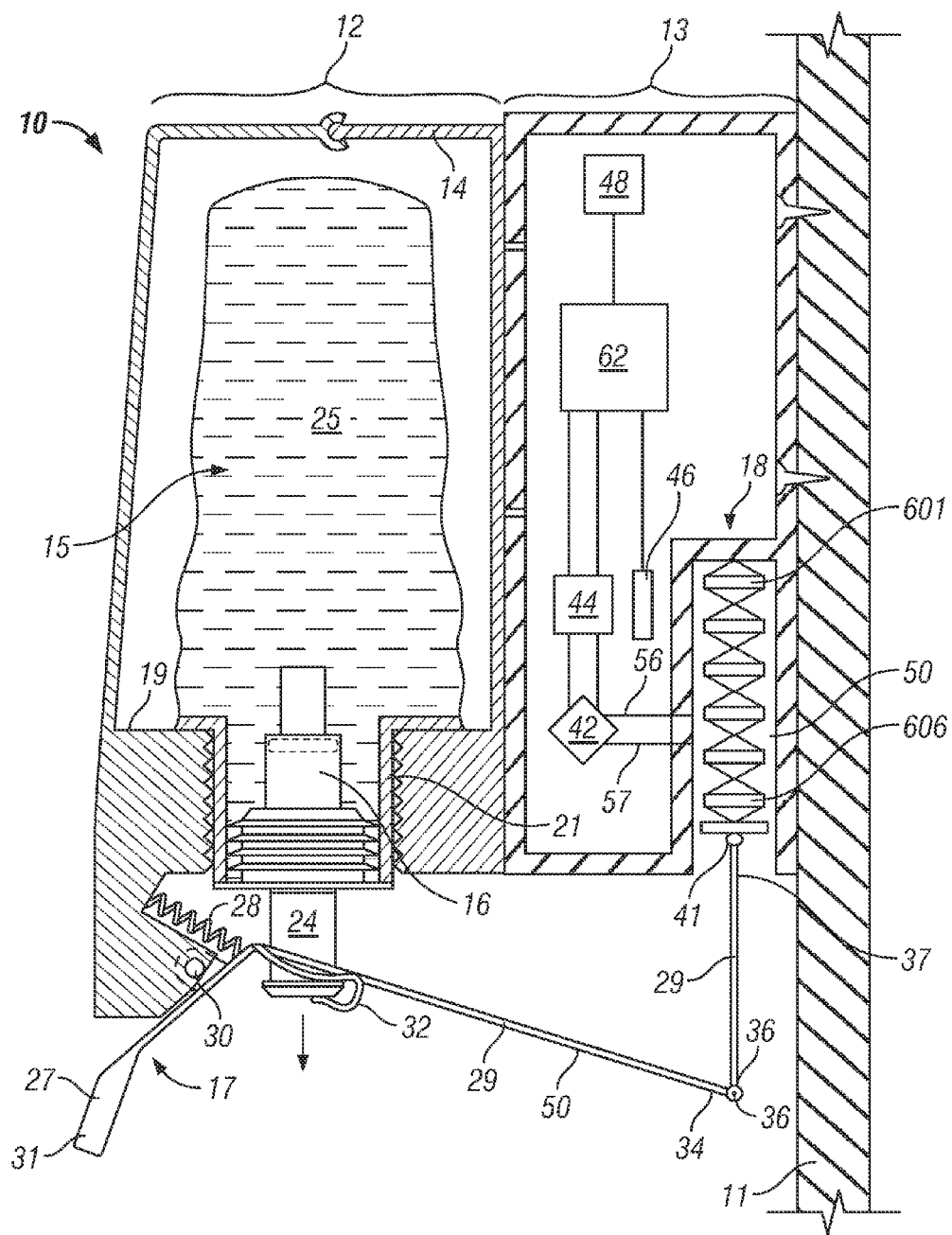
FIG. 12 is a side view of a sixth embodiment of a fluid dispenser of the present invention.
Figure 13:
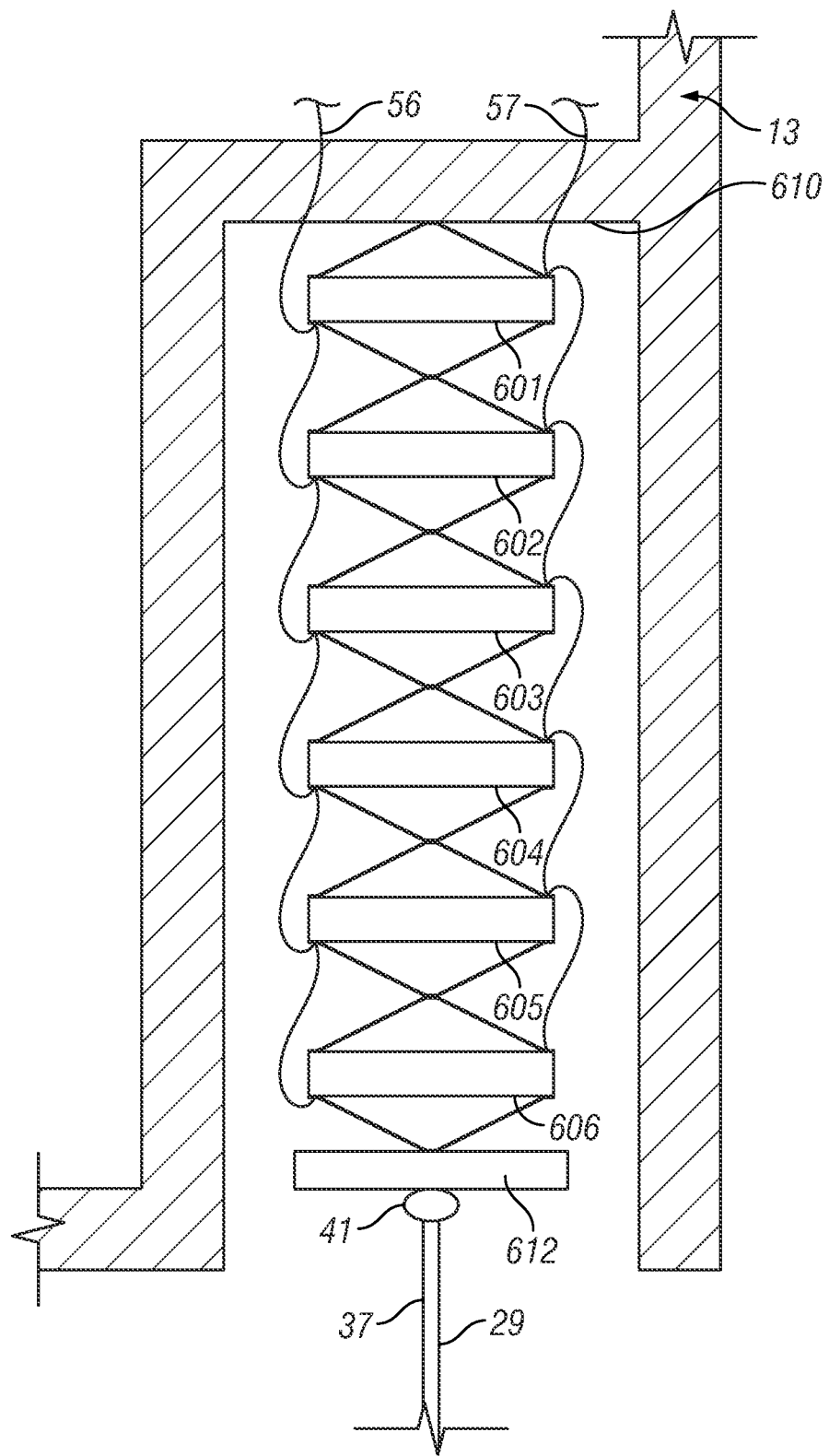
FIG. 13 is an enlarged view of portions of FIG. 12 showing a further embodiment of the electrical generator comprising a stack of piezoelectric harvesters.

Reference is made to FIG. 12 which illustrates a dispenser 12 identical to that in FIG. 1 with the exception that the electric generator 18 is shown in FIG. 12 is a piezoelectric electric generator rather than an electromagnetic induction electric generator. As seen in FIGS. 12 and 13 a plurality of piezoelectric harvesters 601, 602, 603, 604, 605 and 606 are arranged in a stack and are adopted to be compressed vertically between an upper stop surface 610 of the back housing 13 and a press plate 612 connected to the second end 37 of the link 29 by the second horizontal link pivot 41 on a user manually urging the engagement handle 31 rearwardly. Compression of each piezoelectric harvester 601 to 606 which are electrically connected in series generates electrical power delivered via wires 56 and 57 to a suitable electrical component 42.

Figure 14:
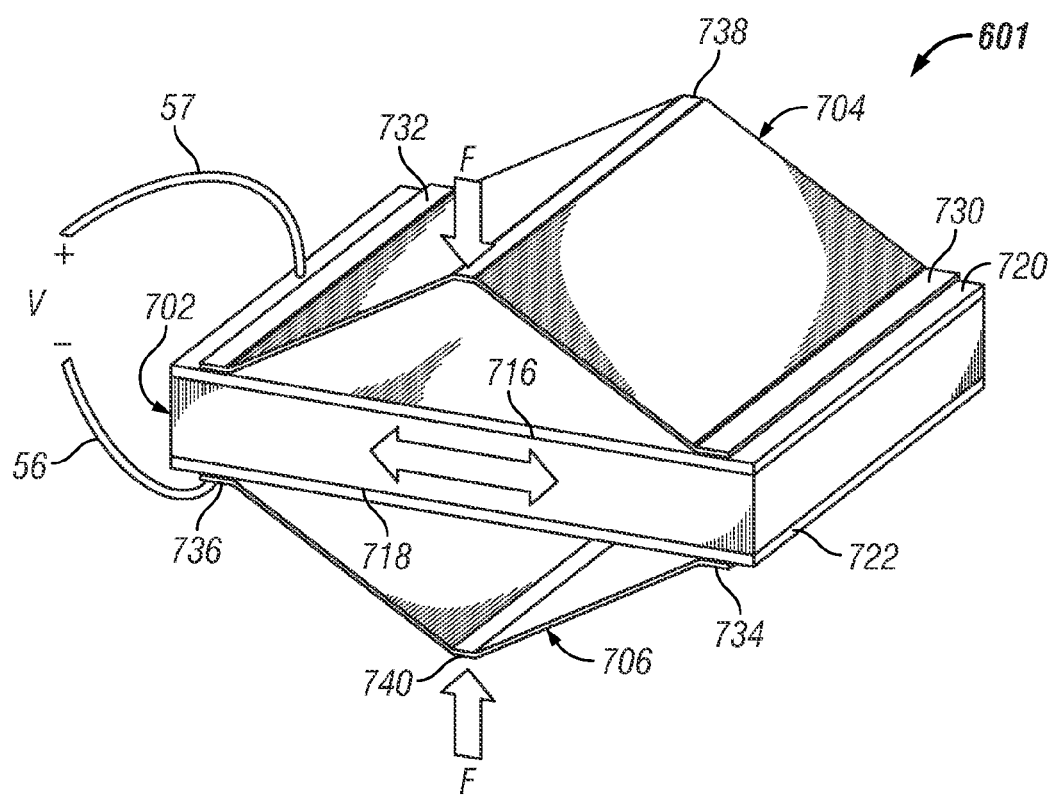
FIG. 14 is a schematic pictorial view of one prior art piezoelectric harvester shown in FIG. 13.
Figure 15:
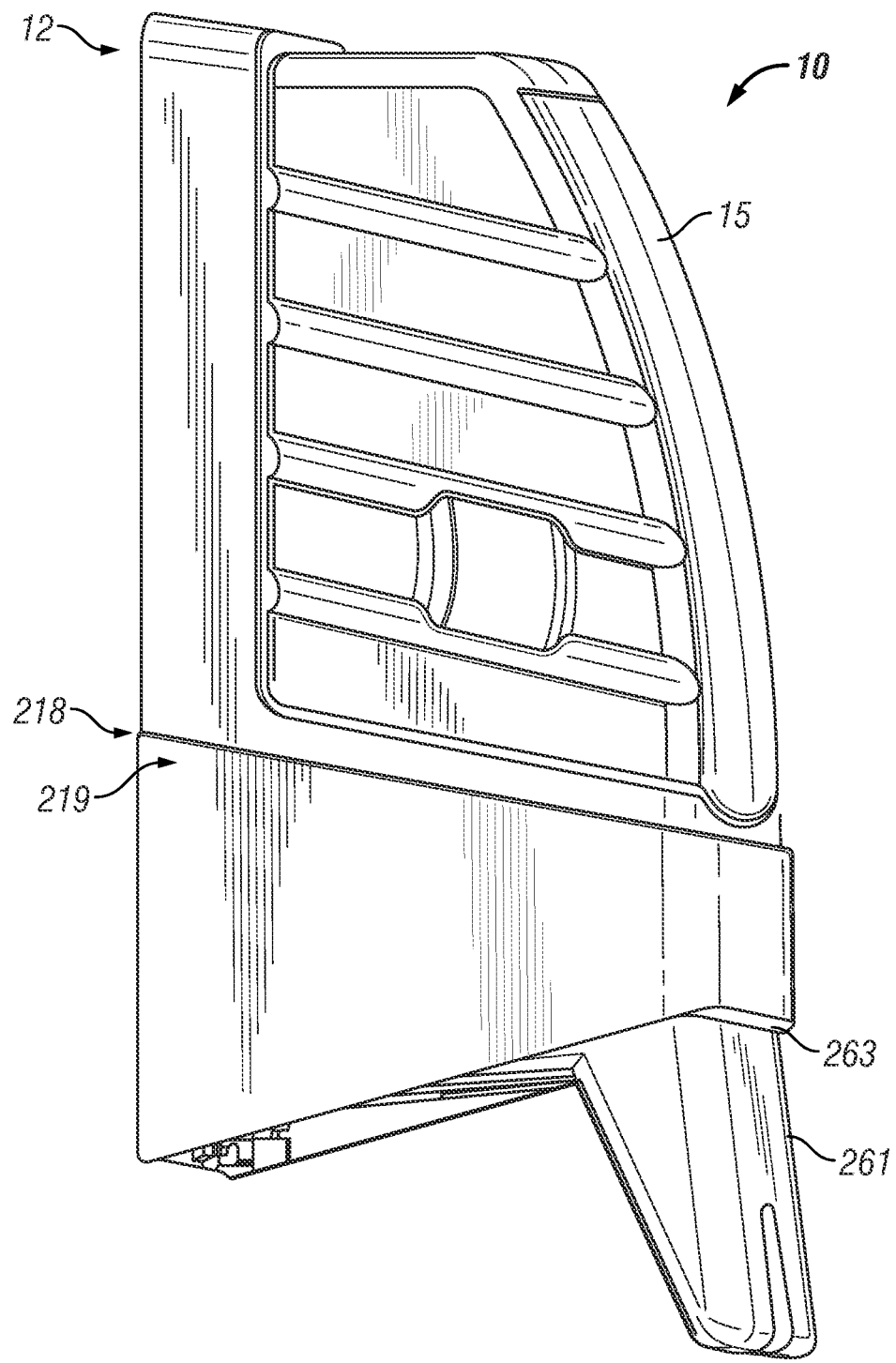
FIG. 15 is a perspective view of a dispenser in accordance with a seventh embodiment of the present invention fully assembled.

One piezoelectric harvester 601 is shown in prior art FIG. 14 and disclosed in U.S. Pat. No. 6,407,486 to Oliver et al, issued Jun. 18, 2002 the disclosure of which is incorporated by reference. FIG. 14 shows a plate 702 of piezoelectric material and two force amplifiers 704 and 706 are bonded to opposite surfaces of the plate. The plate 702 has a polarization along its thickness. The plate 702 has major surfaces 716 and 718 covered by electrode coatings 720 and 722 from which leads 56 and 57 extend. When the plate 702 is stretched along its length a voltage is produces across the major surfaces 716 and 718 by piezoelectric effect. The force amplifiers 704 and 706 are stiff metal sheets which are bonded at their ends 730, 732, 734 and 736 to the electrodes and elevated at their centers 738 and 740. A mechanical fence F applied at the center 738 and 740 is translated into a mechanical tension "T" along the length of the plate 702.

Figure 16:
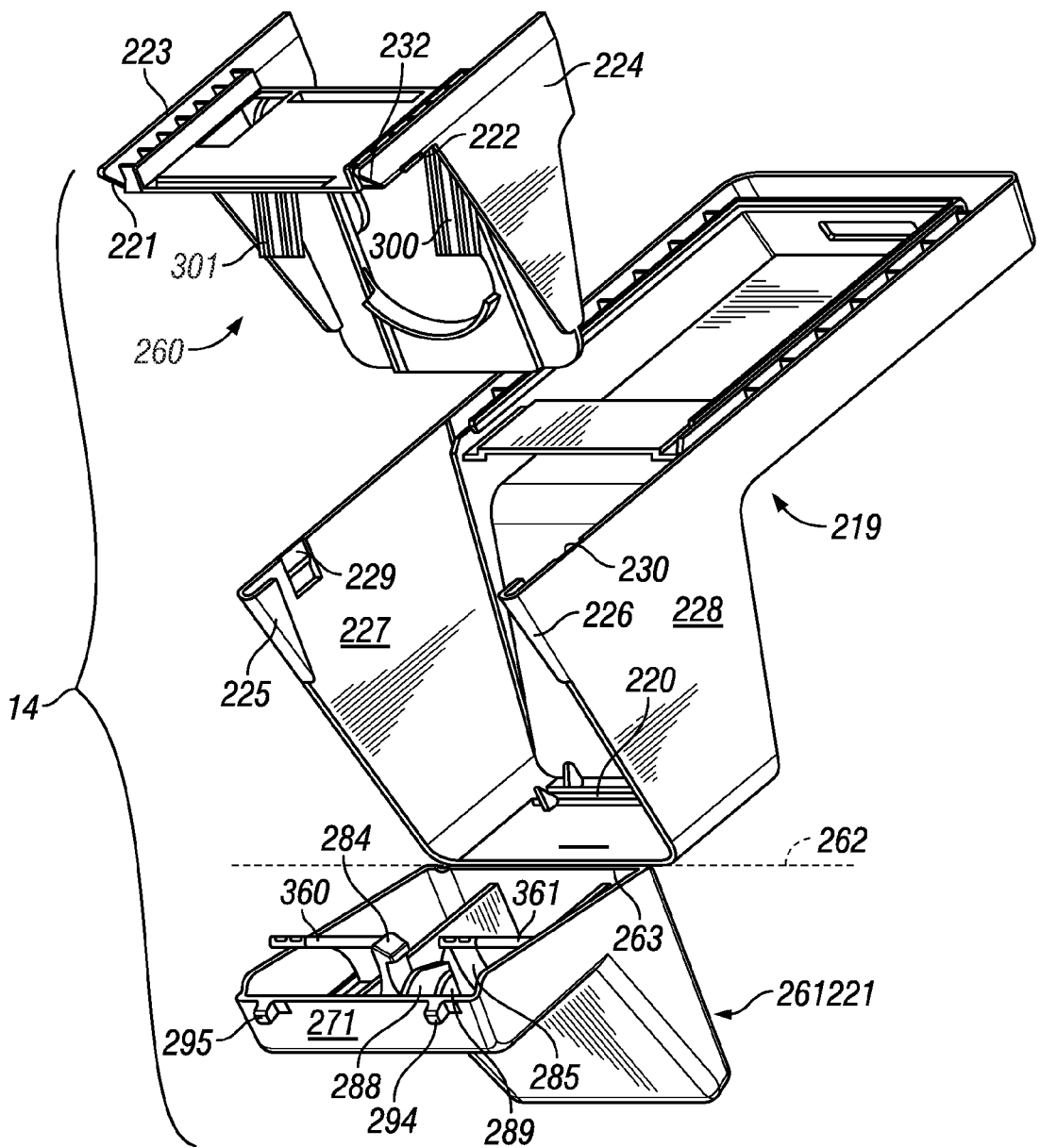
FIG. 16 is an exploded view illustrating an integral housing member and presser member with a removable support plate member for the dispenser of FIG. 15.
Figure 17:
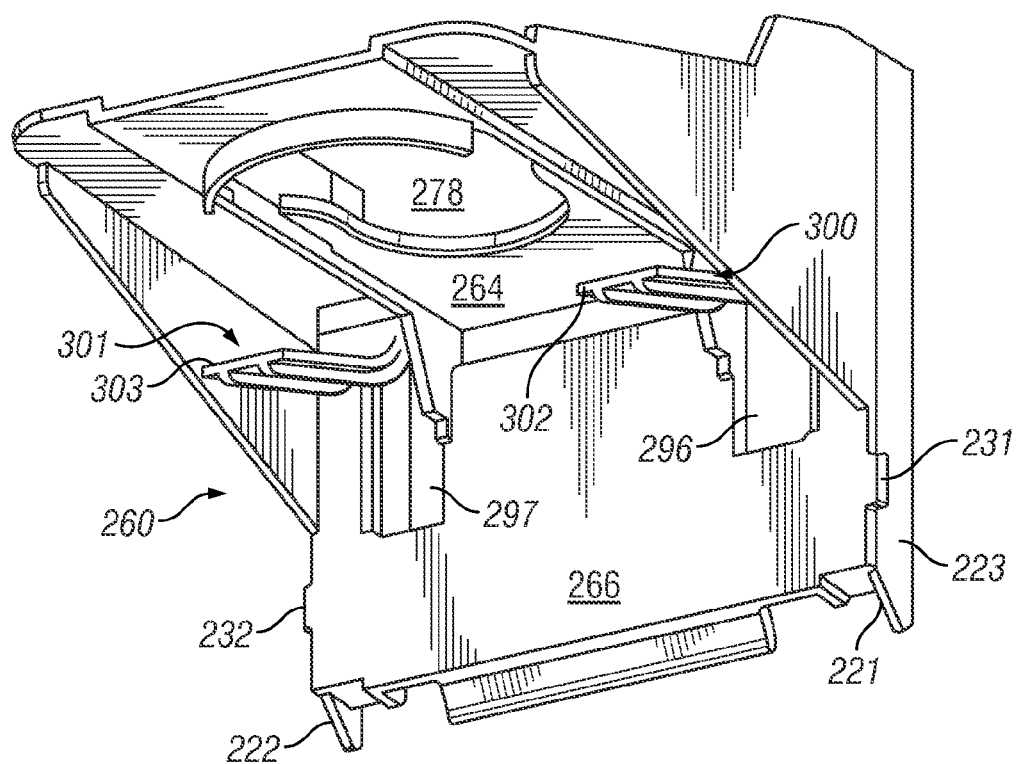
FIG. 17 is a perspective view of the support member also shown in FIG. 16.
Figure 18:
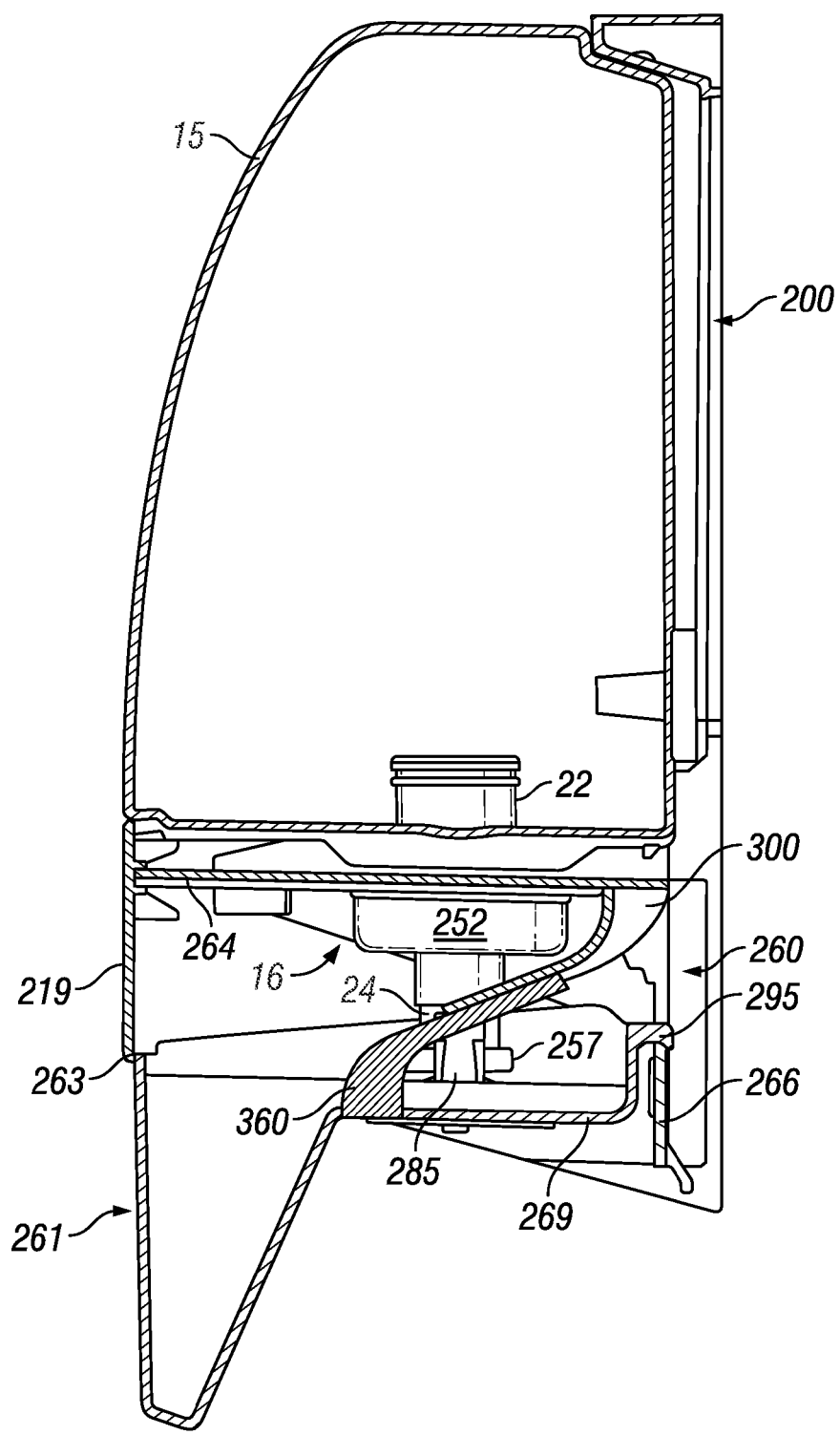
FIG. 18 is a schematic cross-sectional side view through the dispenser of FIG. 15 showing the bottle in a seated position relative to the housing member.

Reference is now made to the seventh embodiment of a dispenser in accordance with the present invention as illustrated in FIGS. 15 to 21. In the seventh embodiment, similar reference numerals are used to refer to elements similar to elements in the first embodiment. The second embodiment illustrates a soap dispenser similar to that disclosed in U.S. Pat. No. 7,568,598 to Ophardt et al, issued Aug. 4, 2009 the disclosure of which is incorporated herein by reference. The second embodiment shows a dispenser assembly 10 comprising a dispensing unit 12 adapted to be removably coupled to a wall plate 200 shown in FIG. 18. The dispensing unit 12 comprises an assembly of a reservoir bottle 15, a piston pump assembly 16, a housing 14. The housing 14 is formed as an integral member having a housing member 219 joined by a living hinge 263 to a presser member 261 for relative pivoting about a hinge axis 262 as seen in FIG. 16. A support member 260 is removably secured to the housing member 219 to be securely received therein as, for example, to be assembled as illustrated in side view in FIG. 18 with a front edge of a support shelf 264 being received in a support slotway 220 on a front wall 221 of the housing member 219 and with a lowermost portion 222 of each side wall 223 and 224 of the support member 260 received in support channels 225 and 226 provided at the rear lower edge of the side walls 227 and 228 of the housing member 219. When the support member 260 is assembled to the housing member 219, the support member 260 is effectively fixedly secured to the housing member 219 against relative movement and provides a housing sub-assembly.

The piston pump assembly 16 comprises a piston chamber-forming member 22 secured in the neck of the bottle 15 and a piston member 24. The reservoir bottle 15 with the piston pump assembly 16 pre-attached thereto as a bottle sub-assembly is coupled to the housing sub-assembly with the neck of the bottle 15 extending through the elongate opening 278 of the support shelf 264, and two resilient piston catch fingers 284 and 285 carried on the presser member 261 engaging an engagement flange 257 of the piston member 24 to couple the piston member 24 for movement with the presser member 261.

The support member 260 carries two elongate spring members 300 and 301 provided on the support member 260 carried on the shelf 264 and extending from a rear end on the shelf 264 forwardly and away from the shelf 264 to distal forward ends 302 and 303. The presser member 261 also carries two elongate ramp members 360 and 361 carried by the shelf 269 of the presser member 261 and extending from a forward end of the shelf 269 rearwardly and upwardly away from the shelf 269 such that the ramp members 360 and 361 extend out of the plane of the shelf 269. The ramp members 360 and 361 have distal second forward ends to engage the distal forward ends 302 and 303 of the spring members 300 and 301 provided on the support member 260. As seen in FIG. 16, the spring members 360 and 361 are provided outwardly from each of the piston catch fingers 284 and 285.

As seen in FIG. 16, the presser member 261 carries on its rear wall 271 two rearwardly extending hook-like catch members 294 and 295 which are adapted to be received in two slots 296 and 297 provided in the rear wall 266 of the support member 260. Each of the slots 296 and 297 have a blind end to engage with the catch members 294 and 295 on the presser member 261 and prevent pivoting of the presser member 261 away from the support member 260 beyond a fully extended position shown in FIGS. 18 and 19. From the extended position of the presser member 261 relative to the support member 60 shown in FIGS. 18 and 19, the presser member 261 may be pivoted about the hinge axis 262 to a retracted position as illustrated in FIG. 20. Reciprocal movement in a cycle between the extended position of FIG. 19 and the retracted position of FIG. 20 will move the piston member 14 of the pump assembly 16 relative the piston chamber forming member 22 and dispense fluid from the bottle 15. In the range of movement between the extended position shown in FIG. 19 and the retracted position shown in FIG. 20, the spring members 300 and 301 on the support member 260 engage the ramp members 360 and 361 on the presser member 261 and bias the presser member 261 to pivot about the hinge axis 262 towards the extended position.

Figure 19:
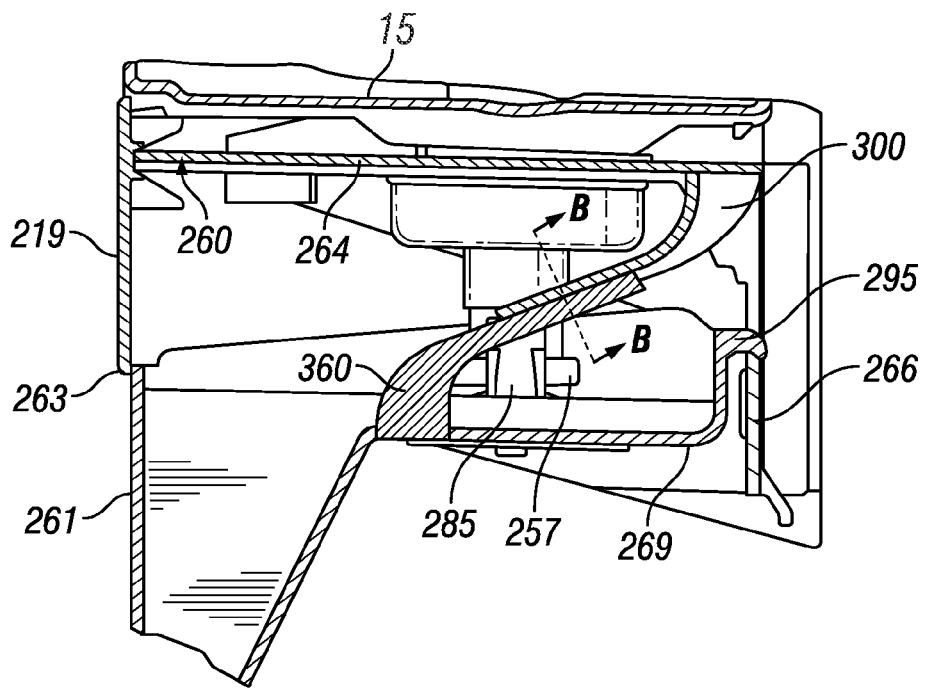
FIG. 19 is an enlarged cross-sectional side view of portions of FIG. 18.
Figure 20:
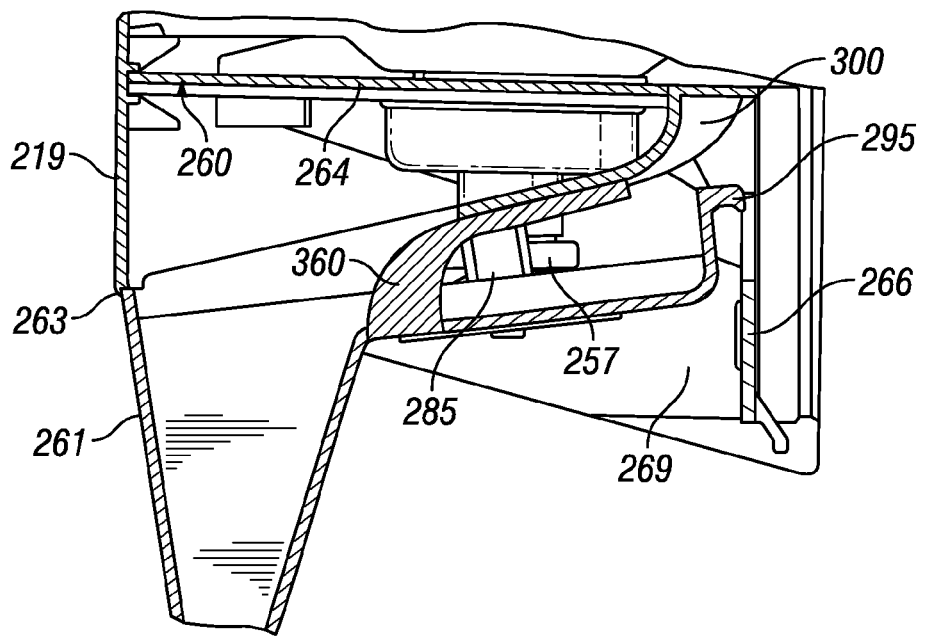
FIG. 20 is a cross-sectional side view the same as FIG. 19, however, showing the presser member pivoted inwardly.
Figure 21:
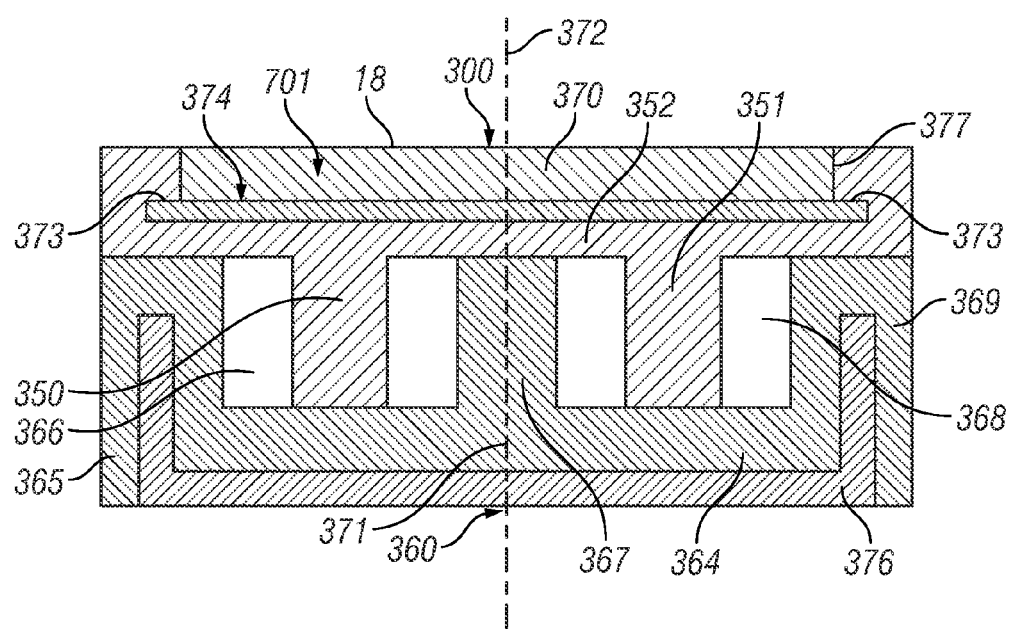
FIG. 21 is a cross-sectional side view along section line 8-8 of the spring elements in FIG. 19.

Reference is made to FIG. 21 which illustrates a cross-sectional side view through the spring member 300 and the ramp member 360 along section lines 8-8 in FIG. 19. As seen, the spring member 300 has an elongate web 352 and a pair of parallel flanges or leg members 350 and 351 extending normal to the web 352. The ramp member 360 of the presser member 261 similarly have an elongate web 364 and three parallel leg members 365, 367 and 369 extending normal to the web 364. As seen in cross-section in FIG. 21, the flange-like legs 350 and 352 of the spring member 300 of the support member 260 are received in the channels 366 and 368 between the legs 365, 367 and 369 of the ramp member 360 contacting the web 364 therebetween. Similarly, the three legs 365, 367 and 369 of the spring member 260 engage the web 352 of the spring member 300 on either side of the legs 350 and 351. The legs 350 and 351 on the spring member 300 effectively form with the portion of the web 352 therebetween a U-shaped member. Any two of the legs 365, 367 and 369 with the web 364 therebetween also form a U-shape member on ramp member 360. The nesting of a leg of the spring member in the channel between the legs of the ramp member provide an advantageous structure such that the spring members 300, 301 which engage the ramp members 360, 361, respectively, will be maintained longitudinally of each other with displacement prevented of one member laterally relative another member that they will not become disengaged from each other.

As seen in side view in FIGS. 19 and 20, the extent to which any one of the flange-like legs 350, 351 extends from the webs 352 is greatest at a first end of the respective spring member 300 where it is coupled to the support member 260 and decreases towards its remote distal end. This is believed to be advantageous to distribute the locations where the spring member 300 may resiliently deform.

Each spring member 300 and 301 and each ramp member 160 and 161 extends longitudinally about a longitudinal axis. The longitudinal axis is schematically illustrated respectively as 370 and 371 for the members 300 and 360 in FIG. 21 and extending the length of each spring member 300, 360 centrally along its respective web 352, 364. In deflection of the spring members, the spring members are resiliently deflectable from an unbiased condition to a deflected condition in a direction generally normal to this longitudinal and preferably in any spring member deflecting between the unbiased condition and the deflected conditions in moving the longitudinal of the spring member remains disposed in a common, flat plane illustrated, for example, as 372 in FIG. 21. The flat plane 372 in which the longitudinal of the spring member 300 moves preferably is normal to the hinge axis 262.

As best seen in FIGS. 19 and 20, each of the webs of the spring members 300 and the ramp member 360 extend from their respective first end as a relatively curved portion merging into a relatively straight portion proximate their distal end. The straight portions of the opposed members 300 and 360 overlap where there is engagement between the opposed members and with pivoting of the presser member 261 relative to the support member 260, the straight portions of each spring members 300 and 360 are permitted to slide longitudinally relative the ramp members 160, 161.

The seventh embodiment illustrates the spring members and ramp members being formed as integral elements with the presser member 261 or support member 260 from which they depend. This is not necessary and each of these members could be provided as a separate element. The seventh embodiment shows a dispenser assembly 10 with the presser member 261 formed integrally with the housing member 219. This is not necessary.

The cantilevered spring members and ramp members need not be made from plastic material but be made, from other materials including spring metal, preferably, continuing to have a similar shape as to the webs and legs. Whether or not the spring members may be formed from plastic or from other materials such as metal, the construction of the spring member to extend along this longitudinal, adapted to deflect normal to the longitudinal and including the web having legs extending away from the web, preferably perpendicular thereto and parallel to its longitudinal, is an advantageous configuration.

The spring member 300 shown in FIG. 21 comprises a composite of a plastic member, preferably integrally formed with the presser member 261 or support member 260 from which it depends, together with a metal spring strip 374 and, as a key component of the electrical generator 18, a piezoelectric harvester 701. In this regard, FIG. 21 shows the spring member 300 as having an elongate open channel 377 disposed along the length of its web 352 provided with opposed slots 373 in each side wall of the channel 371 to extend the length of the spring member 300. The metal spring strip 374 is a flat thin elongate strip of spring metal which is received in the slots 373 and extends across the channel 377. The piezoelectric harvester 701 is secured in the channel 377 outwardly of the strip 374. The spring metal strip 374 has an inherent tendency to assume a preset configuration. The strip 370, while not necessary, is advantageous to ensure that the spring member 300 will maintain operative spring characteristics as, for example, under temperature conditions beyond that normally to be experienced in heated and air conditioned work and living premises, and for extended periods of time. The spring member 300 together with its spring metal strip 374 and piezoelectric harvester 701 are bent along the longitudinal 370 with movement of the presser member 231 between the positions of FIGS. 19 and 20. The spring metal strip 374 and the piezoelectric harvester 701 extend longitudinally of the spring member 300 in the channel 377 over the longitudinal portion of the spring member 300 that are bent with movement of the presser member 231 between the position of FIGS. 19 and 20.

The piezoelectric harvester 701 creates an electrical voltage when bent, for example, as taught in U.S. Pat. No. 3,500,451 to Yando, issued Jun. 29, 1967 the disclosure of which is incorporated by reference. The piezoelectric harvester 701 can be utilized to generate electrical energy as it is bent by the forces applied by the user to move the spring member 300 to a deflected and/or as the spring member 300 returns, from a deflected condition to a rest position under its inherent bias.

While not shown in FIGS. 15 to 21 a manner similar to that in the first embodiment of FIGS. 1 and 2, electrical leads 57 and 57 from the piezoelectric harvester 701 are to be delivered to an arrangement for storing and using the electrical power generated including for example a capacitor 44, dispenser control unit 46 and data communication unit 48 as shown in FIG. 1 which may be provided within the housing 319 or in the wall plate 200.

The ramp members 360 and 361 are preferably rigid and do not deflect. Rigidity can be provided as shown in FIG. 21 by incorporating in the ramp member 360 a rigid metal beam member 376 which extends along the length of the ramp member 360 and prevents bending of the ramp member 360 such that in movement between the extended position of FIG. 19 and the retracted position on FIG. 20 merely spring members 300 and 301 carrying the piezoelectric harvester are deflected. This is not necessary however and the ramp members 360 and 361 could also be elongate deflectable cantilevered spring members and may carry similar piezoelectric harvesters.

While the embodiments describe the electrical storage device 44 as being a capacitor, various other forms of energy storage devices may be used such as rechargeable batteries such as nickel cadmium, nickel metal hydride, lithium ion and lithium polymer rechargeable batteries.

The preferred embodiments illustrate but two versions of electromagnetic electrical generators, one for generating electricity by linear movement and another for generating electricity by rotary movement. It is to be appreciated that various other forms of electrical generators may be used coupled to dispenser 12 such that the cyclical movement of the actuating lever to dispense product results in the generation of electricity. The particular nature of the types of electrical generators which may be used is not limited.

The preferred embodiments illustrate hut two arrangements of piezoelectric generators, one disposed between a lever and a housing and the other disposed in a deflectable spring beam. Many other arrangements for use and placement of piezoelectric generators are possible such that the manual forces applied to the dispenser create stress in a piezoelectric harvester.

The preferred embodiments show the use of a lever pivotable about a pivot axis as an actuator mechanism to activate the dispensing mechanism. Such actuator members are not limited to levers and many other forms of actuating members may be used including a slide member slidable along a slide path and a rotatable member journalled for rotation about a journal axis. The actuator mechanism may utilize a combination of mechanical force conveying arrangements.

The preferred embodiment of FIGS. 1 and 2 illustrates the dispenser sensor unit 46 as being a counter which counts the number of times that the lever 27 is cycled. The number of cycles of the lever 27 can be used as an indication as to whether or not the bottle 15 may be empty of fluid. For example, with knowledge of the approximate dosage that the pump assembly 16 will dispense with each cycling of the lever 27, a calculation can be made as to the number of cyclings of the lever 27 that will result in the bottle 15 being substantially emptied. The dispenser sensor unit 46 can count the number of cycles which count can be used to generate an empty signal when a maximum number of cycles has been exceeded since last replacement of the bottle 15, which maximum number of cycles can be considered to represent an indication that the bottle 15 needs to be replaced. When this empty signal is generated, the information can be communicated to the data communication unit 48 which can transmit the information as a suitable signal wirelessly to the receiver 68. A mechanism for resetting the counter with replacement of the bottle may be provided.

The preferred embodiment of FIGS. 1 and 2 teaches a dispenser sensor unit 46 merely adapted for counting the number of cycles of the actuating lever 27. However, in accordance with the present invention, the dispenser sensor unit 46 may sense one or more of a wide variety of information about the dispensing apparatus, its use, and environment including without limitation any one or more of the following:
  i) an indication as to whether the bottle 15 is full;
  ii) an indication as to the last time that the lever 27 was activated;
  iii) an indication as to the date when the dispensing unit was first activated;
  iv) an indication as to when the bottle was last replaced;
  v) measurement of the fluid level in the bottle;
  vi) information about the nature of bottle 15 which is placed in the dispenser and its fluid 25 and labelling on the bottle 15;
  vii) information about the nature of the dispenser;
  viii) information about the persons using the dispenser; and
  ix) room temperature and humidity.

Dispenser sensor unit 46 could employ a wide variety of different sensors capable of determining product low conditions including infrared sensors, mechanical levers and mechanical strain gauges.

Figure 22:
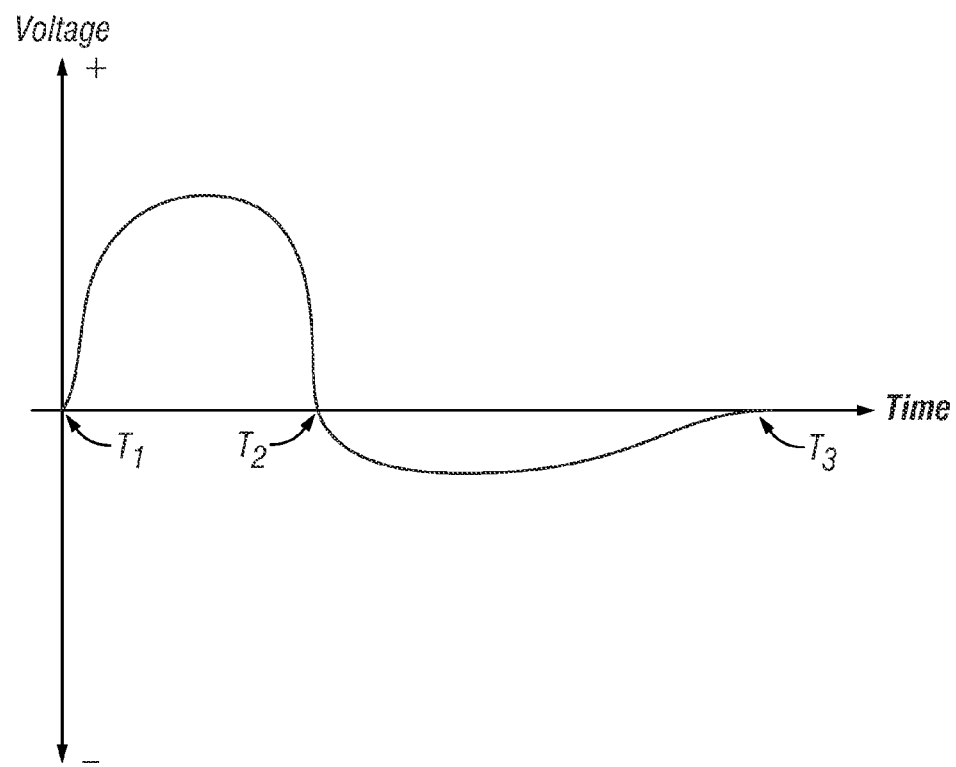
FIG. 22 shows a relationship between voltage generated by the generator of FIGS. 1 and 2 and time.

Reference is made to FIG. 22 which is a graph showing on a vertical axis the voltage and on the horizontal axis time. FIG. 22 illustrates the voltage generated with time by the embodiment of FIGS. 1 and 2 with T1 representing the time at the beginning of the cycle with the dispenser assembly in the extended position shown in FIG. 2, T2 representing the time during cycle after the compression stroke when the dispenser assembly is in the retracted position shown in FIG. 2 and T3 representing the end of a cycle after the extension stroke when under the influence of the spring the lever is returned to the extended position shown in FIG. 1. Since electrical energy is defined by the formula $E=VC$ where "E" is the electrical energy, "V" is the voltage and "C" is the current, similar graphs could be developed for the electrical energy generated to show either the current or the voltage as developed during the cycle. In FIG. 22, the duration of the compression stroke is the time between T1 and T2 and the duration of the extension stroke is the time between T2 and T3. While the relative duration of the extension stroke and the compression stroke will depend on the manner of operation and the configuration of the dispenser, generally it is considered that ape/son using the dispenser in FIGS. 1 and 2 would, in a relatively short period of time in the compression stroke, move the lever from the extended position to the retracted position and thereafter the spring due to its inherent resiliency would move the device in the extension stroke from the retracted position to the extended position with the extension stroke being longer than the retraction stroke. FIG. 22 shows that voltage is generated in the embodiment in FIGS. 1 and 2 in both the compression stroke and the extension stroke. The system and its circuitry can be selected and controlled so as to harvest energy in merely one or both of these strokes. Merely harvesting energy in the retraction stroke while a user is moving the lever can be advantageous such that the return spring need not have any additional load arising due to electrical energy generation in the extension stroke.

When electrical energy is generated, one or more of the features of the energy generated may be measured so as to produce a measured result. The feature to be measured may be selected from the group consisting of a feature of the voltage of the energy generated, a feature of the current of the energy generated and a feature of the energy generated or combination of these. Thus, for example, as seen in FIG. 22 with the voltage the measured feature may include the existence of a pulse of one or more of current, voltage or energy; a duration of a pulse of one or more of a current, voltage or energy and a feature of pulse of one or more of the current, voltage or energy including features such as the duration of a pulse, the amplitude of a pulse and the average value of a pulse. The measured feature may also be selected from a peak voltage or current level generated within a time period, a peak rate of generation of electrical energy, and a summation of the voltage, current or electrical energy generated within a time period.

The measured result of the feature of the energy generated can be used in accordance with the present invention to provide an estimated amount of the fluid discharged.

In accordance with the present invention there is provided a method of operation of a fluid dispensing apparatus of each of the seven embodiments of the present invention with the method comprising the steps of (a) moving an actuation mechanism to cause the discharge of fluid by activating a dispensing apparatus and to generate electrical energy with the generator, (b) measuring at least one feature of the energy generated to produce a measured result and (c) estimating as a function of said measured result an estimated amount of fluid discharged. The estimated amount of fluid discharged may be for any one individual stroke or for a series of successive strokes over time. As in the preferred embodiments, the fluid dispensing apparatus for use in a method in accordance with the present invention preferably contains a dispensing mechanism which on activation causes fluid, as from a reservoir, to be discharged, and for activation for a dispensing mechanism by movement of an activation mechanism between different relative positions, with the activation mechanism adapted for engagement by a user to move the activation mechanism and an electrical generator for generating electricity with the electrical generator coupled to the activation mechanism such that on movement of the activation mechanism to discharge fluid the generator generates electrical energy.

The function which is used to estimate the estimated amount of fluid discharged from the measured result for the feature of the electrical energy generated may be determined in a number of ways. One preferred way is to operate a test dispenser substantially the same or comparable to the fluid dispensing apparatus in a calibration test including a plurality of the above-mentioned step (a) and for each step (a) performing step (b) to measure the feature of energy generated and additionally performing an additional step (x) of measuring the actual amount of fluid discharged in each step (a). From such data which may be selected so as to provide in the calibration test a series of different movements of the activation mechanism characteristic of a relatively full range of movements which may be expected in normal operation of the fluid dispenser, a person skilled in the art can then establish the function, for example, as a mathematical relationship approximating the relationship, covering all the test steps (a), between the measured result for the feature of each test step (a) and the amount of fluid discharged for each test step (a). Such mathematical modelling is well known to persons skilled in the art. Other methods for determining the function can include estimating the volume of fluid discharged relative to the relative extent of movement of the actuation mechanism between different of said positions and correlating this with an estimate of the relative extended movement of the activation mechanism which would provide for various values for the measured result for the feature of the energy generated. Calibration whether by experimentation or calculation is within the skill of a person skilled in the art so as to select a function of the measured result of the energy generated which will estimate the amount of fluid discharged for any particular pump having regard to, amongst other things, the nature of the pump to the nature of the fluid dispensed, temperature, modes of operation and the like.

One preferred use of the method of estimating the amount of fluid discharged is to provide a signal or arrangement which assists in ensuring that a minimum dose of fluid is dispensed to each user.

For example, in the context of a hand cleaning fluid dispenser, a determination may be made, for example, that 3 mm of the fluid in question is required for adequate cleaning of a user's hands. The method may be carried out so as to determine for each user whether the desired minimum dose has been dispensed and to provide a suitable signal to the user. For example, for a given step (a), step (b) may be carried out to produce a measured result for step (a) and subsequently step (c) is carried out to estimate an estimated amount of fluid discharged for the given step (a). Furthermore, a step (d) may be then be carried out for comparing the estimated amount of fluid discharged for the given step (a) to a predetermined minimum dose volume and providing a signal to the user indicative of whether the estimated amount of fluid discharged for the given step (a) is (j) less than the predetermined minimum dose or (ii) at least equal to the predetermined minimum dose. If the estimated amount of fluid discharged is at least equal to the predetermined minimum dose, then a signal to that effect may be given to the user. If after providing the signal to the user indicative of the estimated amount of fluid discharged for the given step being less than predetermined minimum dose, then after a next step (a) is performed step (b) is carried out to produce a measured result for the next step (a) and then step (c) is carried out to determine an estimated amount of fluid discharged for the next step. Subsequently a further step (e) is carried out for comparing the sum of the estimated amounts of the fluid discharged for the given step (a) and the next step (a) to the predetermined minimum dose and providing a signal to the user indicative of whether the new sum is (i) less than the predetermined minimum dose or (ii) at least equal to the minimum predetermined dose. This sequence can be repeated after each step the sum of the estimated amounts of fluid discharged in a successive series of step at least equal to the predetermined minimum dose.

Such a method is useful for example in a soap dispenser in which a normal dose dispenses on each activation by a user, for example, about 1 ml to 1.5 ml of fluid, but the minimum dose is for example 3 ml. In manually operated dispensers of the type disclosed in the preferred embodiments, the amount of fluid disposed in any one cycle of operation can vary dependent upon the extent to which the user may adequately move the actuator mechanism such that the lever shown in FIGS. 1 and 2 may generate a full stroke of movement of the piston. As well, the speed or force applied by the user can have an effect on the amount of fluid dispensed. Further, the extent to which the user may not for example permit the lever to be returned to a fully extended position of the piston can have an effect on the amount of fluid dispensed. Estimating some of the estimated amounts of fluid dispensed to an individual user can be advantageous to better ensure that an individual user actually receives a minimum dose of fluid.

In order to distinguish dispensing by one user from an earlier or later user, the time between individual strokes, that is for example between pulses of generated electrical energy can be monitored and if the time is for example greater than a preset time then the new operation can be considered to be operation by a new user.

As to the nature of the signal to a user, the signal may be a visual signal, an audio signal or a combination of audio and visual signals. For example, the visual signals might be an arrangement by which a green light on the exterior of the dispenser is illuminated adjacent a notice indicating that a minimum dose has been obtained or a red light is illuminated adjacent a notice indicating that a minimum dose has not been obtained and/or requesting the user operate the lever again to dispense additional fluid. Audible signals could of course provide such a signal to the user in spoken wording and any such visual and audible signals could be provided in combination.

As a matter of compliance with washing regulations, the controlled mechanism could also be operated to keep track of incidences where users did not operate the dispenser so as to receive a minimum dose. As well, the control mechanism may keep track of the number of times the dispenser needed to be operated a plural of times to discharge a minimum dose a user. Such information for compliance and monitoring the operation of the dispenser could for example be communicated by a communication unit to remote controller.

The individual dispensing apparatus may be operated in a manner so as to change the predetermined minimum dosage which is to be desired to be dispensed dependent on a number of different factors. These factors can include factors which could readily be sensed by the dispensing unit including the temperature of the environment where the apparatus is located, the length of time since fluid was last dispensed and the length time since which the reservoir initially had fluid dispensed from it. Additionally, the predetermined minimum dose could be selected dependent upon the nature of the fluid being dispensed which could be adjusted as for example on changing a replaceable reservoir from containing one fluid to containing another fluid. Additionally, the minimum dose could be changed to depend upon information regarding the threat or risk of infection in the environment in which the apparatus is located. Such information could, for example, be provided to the dispenser as input from a remote controller as for example received by wireless communication. A method can be carried out wherein a step of generating ozone creates an initial ozone concentration in the air in the compartment immediately after creating the ozone which initial ozone concentration is selected to meet one of a plurality of pre-determined minimum ozone concentrations and selecting one of the plurality of pre-determined minimum ozone concentrations as a function of the information received regarding the threat or risk of infection to provide an increased initial ozone concentration with an increase in the threat or risk of infection.

The method of the present invention involving estimating the amount of fluid discharged can be used to provide signals indicative of the amount of fluid remaining in a reservoir based on for example a comparison of a cumulative sum of estimated amounts of fluid discharged from the reservoir after the reservoir first has fluid dispensed therefrom and an estimated volume of fluid in the reservoir prior to the reservoir first having fluid dispensed therefrom. For example, in the context of a fluid dispenser having a replaceable reservoir, the control mechanism may have an initialization indicator which determines when a reservoir is being inserted. The control mechanism can thereafter calculate a cumulative sum of the estimated amounts of fluid discharged. By comparison of the cumulative sum to the estimated initial volume of fluid in the reservoir, the control mechanism can provide various signals indicative of the amount of fluid remaining in the reservoir. These signals can indicate conditions selected for example from a condition that the reservoir is estimated to be empty and a condition that the reservoir is estimated to have fluid remaining therein below a certain percentage of the estimated initial volume of fluid in the reservoir. Such signals may not only be displayed for example visually on the individual dispenser they may also preferably be communicated via a data communications unit configured for transmitting information preferably wirelessly to a wireless receiver which would pass the information on to a remote controller. By such an arrangement, the manual soap dispenser can provide signals to the central controller that the replaceable reservoir is in need of replacement. The control mechanism could also keep track of the time when a new replaceable reservoir is inserted and if the cumulative sum of the estimated amounts of fluid discharged from the reservoir after it is inserted does not reach a condition that the reservoir is expected to be empty within a set product life period of time, then a suitable signal may be sent. Towards keeping the complexity of control mechanism in the manual dispenser at a minimum, the control mechanism may be preferably be structured so as to wirelessly transmit data regarding its stats operation and use to the central remote controller rather than retain substantial information in the control mechanism in the manual dispenser.

The control mechanism for the fluid dispensing apparatus may include various elements to carry the desired operations including a measurement device that measures the feature of the energy generated, a computational device that estimates from the measured results for the feature the estimated amount of the fluid discharged. The measurement device may include a dispenser sensor unit which measures the feature.

In the preferred embodiment, the dispenser is shown as a fluid dispenser preferably a soap dispenser as for use in a washroom or an alcohol cleaning fluid dispenser as for use in hospitals. The nature of the manual dispenser is not limited to fluid dispensers. Other dispensers with which the present invention can be useful include manually operated paper towel dispensers as for use in washrooms as, for example, notably including those in which a lever is activated to dispense paper towels, however, also including those in which drawing of paper is required for dispensing of the paper in which in the manual drawing on the paper will rotate an axle member about which a roll of paper is engaged. Other dispensers include a fluid dispensing apparatus wherein said dispenser mechanism is selected from the group consisting of a paper towel dispenser, a liquid or foam soap dispenser, a toilet tissue dispenser, and an air freshener dispenser, toilet seat cover dispenser, diaper dispenser, a feminine product dispenser; a beverage dispenser, and a sunscreen fluid dispenser.

The data communication unit 48 preferably uses wireless communication technology such as is well known in the art and includes Wi-Fi (Wireless Fidelity) and Bluetooth communication technology. The communication may merely be one-way as from the data communication unit 48 to the receiver 68, however, may preferably be two-way communication. The receiver 68 may comprise a remote computer or an interface or gateway for connection between electronic devices such as a remote computer. A gateway may incorporate an http server for accessing data from the data control unit 48 and for transmission of this data back to the data transmission unit 48. The individual dispenser 10 may be accessed as if the dispenser assembly 10 was on a website, and the information could be displayed on a web browser.

Wireless communication to and from the data communication unit 48 is preferred, however, wired communication as along a wired connection from the data communication unit 48 to the receiver 66 is also within the scope of this invention.

Outputs from the data communication unit 48 could be incorporated into known systems and methods for measuring monitoring controlling washroom dispensers and products of the type disclosed in U.S. Patent Publication 2005/0171634 to York et al dated Aug. 4, 2005, the disclosure of which is incorporated herein by reference.

Rather than utilize a piston pump assembly as shown in FIGS. 1 to 3 which discharges in a retraction stroke, a piston pump assembly could be used which discharges in a withdrawal stroke, that is, when the housing is moving from the forward position to the rear position. The manually operated pump assembly illustrated in FIG. 1 is adapted for applying manual pressure to the manual engagement handle 31 of the lever 27 to move the lever 27 rearwardly relative to the housing. It is to be appreciated that a different arrangement of an activating lever could be provided in which a manual engagement handle is to be moved forwardly away from the wall. An activating lever which is moved forwardly could be used in conjunction with a piston pump which discharges in a withdrawal stroke rather than in a retraction stroke.

The dispenser may have side mounted activation levers such as taught in U.S. Pat. No. 7,367,477 to Ophardt issued May 6, 2008, the disclosure of which is incorporated herein by reference.

As a pump assembly for dispensing a fluid, the embodiment illustrates the use of a piston type pump. The invention is not so limited that any manner of fluid discharge mechanism may be suitable when the product is a fluid including, for example, rotary pumps, peristaltic pumps, and valve arrangements releasing fluids from pressurized bottles and the like, without limitation.

The dispenser is preferably adapted for dispensing fluid onto a user's hand disposed below the dispenser, however, the dispenser can also be adapted to dispense onto a user's hands in front of or to the side of the dispenser.

The preferred embodiments show a fluid dispenser to dispense liquids. The fluid dispensers in accordance with the present invention include dispensers in which the fluid is dispensed as a spray or as a foam. For example, by suitable selection of a pump and nozzle, fluid dispensed may be sprayed as in an atomized mist. Known spray dispensers include dispensers to dispense a spray of alcohol disinfectant onto a person's feet. Foam dispensers provide a foam as by mixing liquid to be dispensed with air.

The dispenser need not be limited to dispensing of fluids onto a person's hands and may be adapted for dispensing another application such as to dispense a food product such as ketchup or mustard as used in fast food industries, to dispense cream or milk, to dispense fluid medications as into a cup or receptacle or the like, without limitation.

Figure 23:
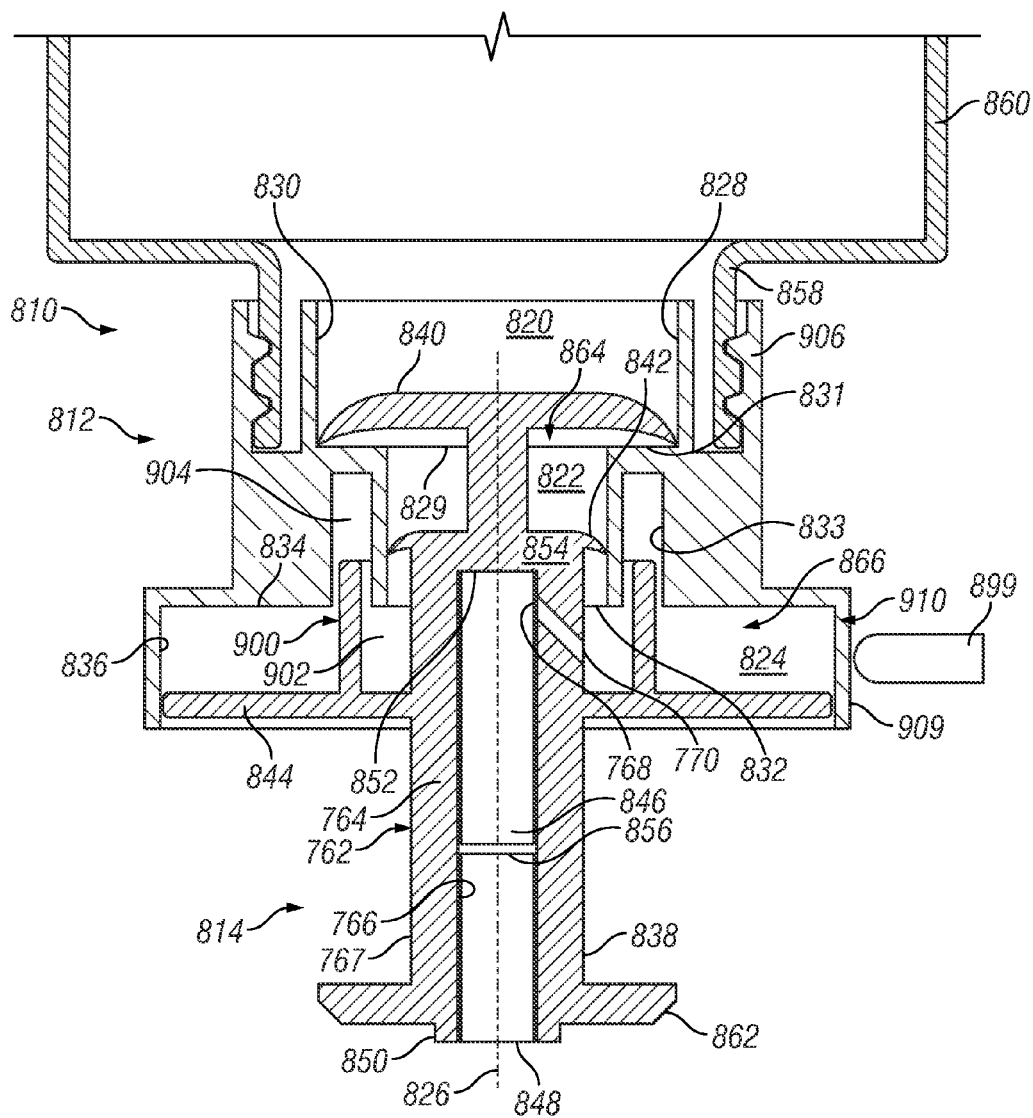
FIG. 23 is a schematic cross-sectional side view showing the combination of: a piston pump assembly in accordance with an eighth embodiment of the present invention with the piston in a fully extended position; a fluid containing reservoir; and an ultraviolet radiation emitter.
Figure 24:
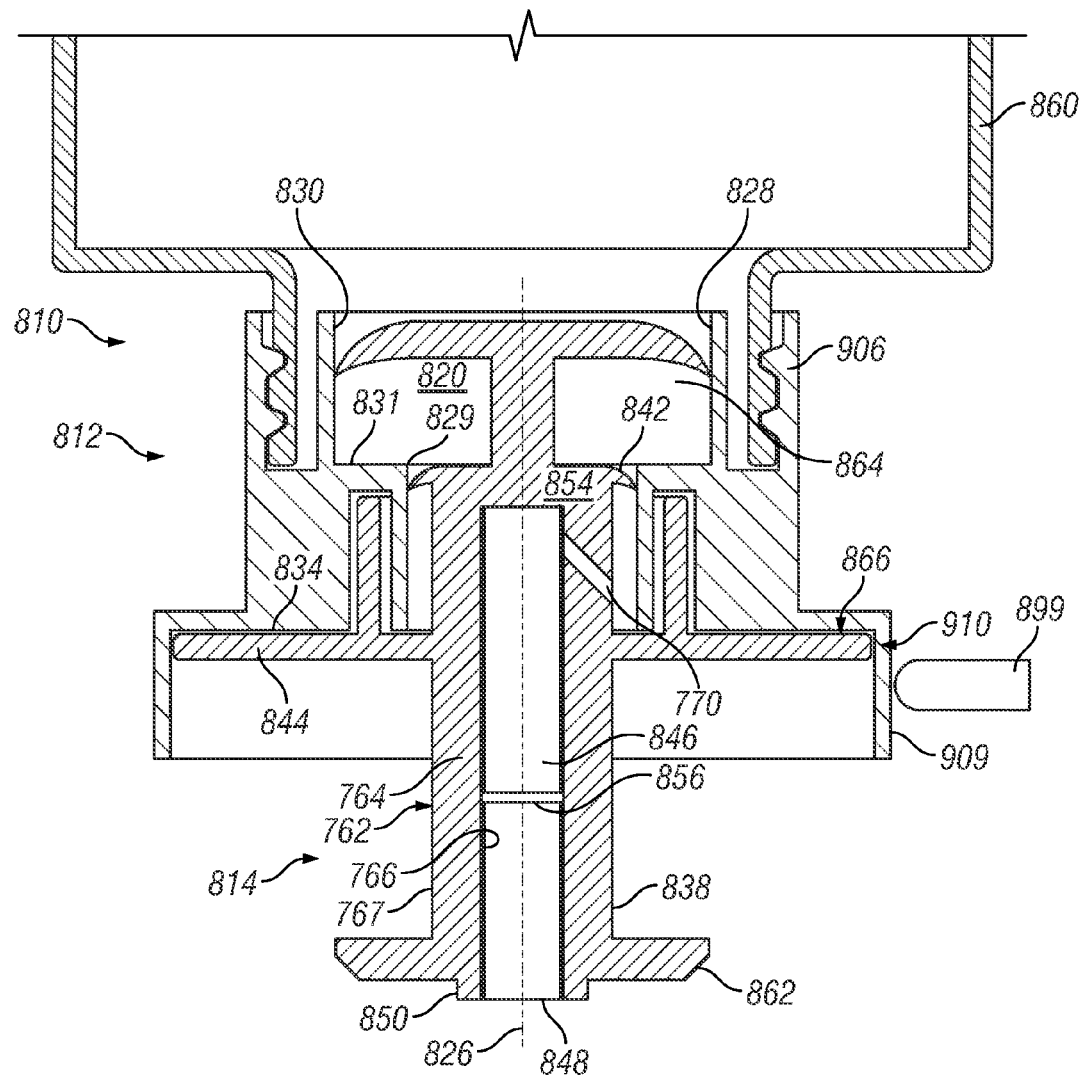
FIG. 24 is a cross-sectional side view of the pump assembly the same as in FIG. 23 but with the piston in a fully retracted position.
Figure 25:
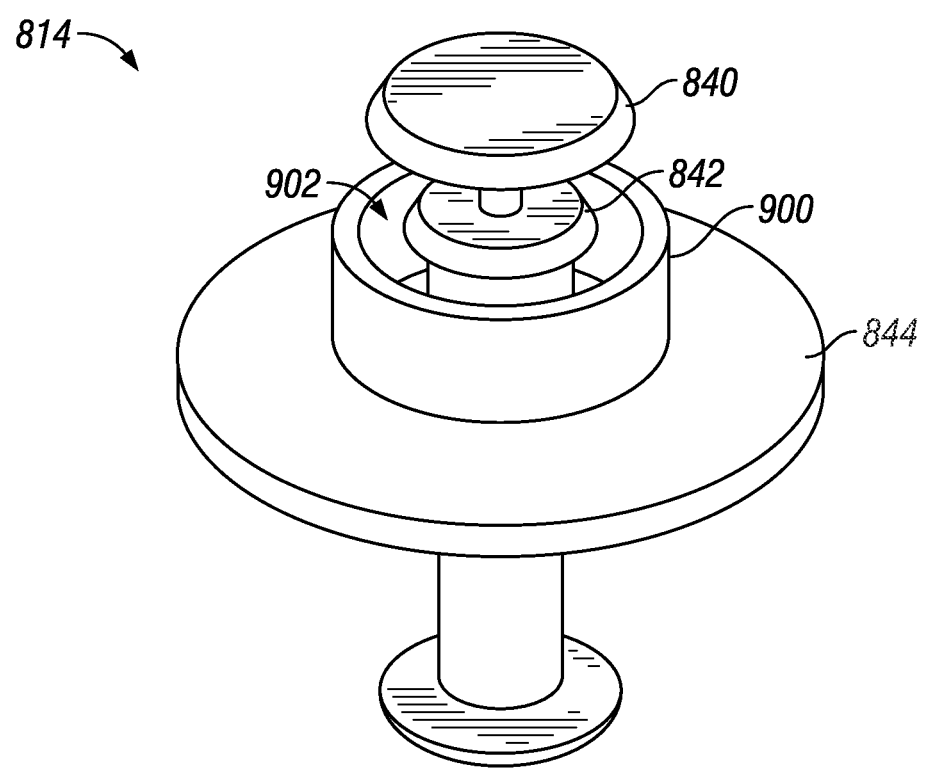
FIG. 25 is a perspective view of the piston of the pump assembly shown in FIG. 23.

Reference is made first to FIGS. 23, 24 and 25 which show an eighth embodiment of a pump assembly generally indicated 810 in combination with a fluid containing reservoir 860 and an ultraviolet radiation emitter 899. Pump assembly 810 comprises two principal elements, a piston chamber-forming member or body 812 and a piston forming element or piston 814 which has a configuration similar to that disclosed in U.S. Patent Application Publication US 2009/0145296 to Ophardt et al published Jun. 11, 2009, the disclosure of which is incorporated herein by reference.

The piston chamber-forming body 812 has three cylindrical portions illustrated to be of different radii, forming three chambers, an inner chamber 820, an intermediate chamber 822, and an outer chamber 824, all coaxially disposed about an axis 826. The intermediate cylindrical chamber 822 is of the smallest radii. The outer cylindrical chamber 824 is of a radius which is larger than that of the intermediate cylindrical chamber 822. The inner cylindrical chamber 820 is of a radius greater than that of the intermediate cylindrical chamber 822 and, as well, is shown to be of a radius which is less than the radius of the outer cylindrical chamber 824.

The inner chamber 820 has an inlet opening 828 and an outlet opening 829. The inner chamber has a cylindrical chamber side wall 830. The outlet opening 829 opens into an inlet end of the intermediate chamber 822 from an opening in a shoulder 831 forming an outer end of the inner chamber 820. The intermediate chamber 822 has an inlet opening, an outlet opening, 82, and a cylindrical chamber side wall 833. The outlet opening 832 of the intermediate chamber 822 opens into an inlet end of the outer chamber 824 from an opening in a shoulder 834 forming the inner end of the outer chamber 824. The outer chamber 824 has an inlet opening, outlet opening and a cylindrical chamber side wall 836.

Piston 814 is axially slidably received in the body 812. The piston 814 has an elongate stem 838 upon which four discs are provided at axially spaced locations. An inner flexing disc 840 is provided at an innermost end spaced axially from an intermediate flexing disc 842 which, in turn, is spaced axially from an outer sealing disc 844. The inner disc 840 is adapted to be axially slidable within the inner chamber 820. The intermediate disc 842 is adapted to be axially slidable within the intermediate chamber 822.

The intermediate disc 842 has a resilient peripheral edge which is directed outwardly and adapted to prevent fluid flow inwardly yet to deflect to permit fluid flow outwardly therepast. Similarly, the inner disc 840 has a resilient outer peripheral edge which is directed outwardly and is adapted to prevent fluid flow inwardly yet to deflect to permit fluid flow outwardly therepast.

The outer sealing disc 844 is adapted to be axially slidable within the outer cylindrical chamber 824. The outer sealing disc 844 extends radially outwardly from the stem 838 to sealably engage the side wall 836 of the outer chamber 824, and prevent flow therepast either inwardly or outwardly. The outer sealing disc 844 carries an upwardly inwardly extending cylindrical tube 900 such that an annular central fluid sump 902 is defined inside the tube 900 between the tube 900 and the stem 838 above outer disc 844. As seen in FIGS. 23 and 24, the piston chamber-forming body 812 has an inwardly extending cylindrical recess 904 sized to receive the tube 900 therein but with clearance to provide for fluid passage therebetween.

The piston 814 essentially forms, as defined between the inner disc 840 and the intermediate disc 842, an annular inner compartment 864, sometimes referred to herein as a liquid compartment or inner liquid compartment, which opens radially outwardly as an annular opening between the discs 840 and 842. Similarly, the piston 814 effectively forms between the intermediate sealing disc 842 and the outer sealing disc 844 an annular outer compartment 866, sometimes referred to herein as an air compartment or an outer air compartment, which opens radially outwardly as an annular opening between the discs 842 and 844.

The stem 838 has an outermost hollow tubular portion 762 with a cylindrical side wall 764 generally coaxially about the central axis 826 defining a central passageway 846 within the tubular portion 762. The central passageway 846 extends from an outlet 848 at the outermost end 850 of the stem 838 centrally through the stem 838 to a closed inner end 852.

The cylindrical side wall 764 of the hollow tubular portion 762 of the stem 838 extends radially of the central axis 826 from an inner side wall surface 766 to an outer side wall surface 767. An inlet passageway 854 provides communication through the stem 838 into the central passageway 846. The inlet passageway 854 extends through the cylindrical side wall 764 from an inner opening 768 in the inner side wall surface 766 to an outer opening 770 in the outer side wall surface 767. The inlet passageway 854 has its outer opening 770 located on the stem 838 in between the outer disc 844 and the intermediate disc 842. The inlet passageway 854 in extending from the inner opening 768 to the outer opening 770 radially outwardly and axially outwardly so as to provide the inner opening 768 located on the stem 838 axially inwardly from the outer opening 770. The inlet passageway 854 extends about an inlet axis extending in a flat plane including the central axis 826 and with the inlet axis in that flat plane extending at an angle to the central axis 826 as the inlet axis extends radially outwardly and axially outwardly.

The inlet passageway 854 has its inner opening 768 at a height above the height of its outer opening 770.

A foam inducing screen 856 is provided in the central passageway 846 intermediate between the inner opening 768 and the outlet 848. The screen 856 may be fabricated of plastic, wire or cloth material. It may comprise a porous ceramic measure. The screen 856 provides small apertures through which an air and liquid mixture may be passed to aid foam production as by production of turbulent flow through small pores or apertures of the screen thereof in a known manner.

The piston 814 carries an engagement flange or disc 862 on the stem 838 outward from the outer sealing disc 844. The engagement disc 862 is provided for engagement by an activating device in order to move the piston 814 in and out of the body 812.

The piston chamber-forming body 812 carries an inwardly directed annular flange 906 which is threaded on a radially inwardly directed surface and adapted to threadably engage in a sealed manner with the threads on the neck 858 of the container 860. The neck 858 extends, as seen in FIG. 23, downwardly into an outwardly extending annular cavity formed between the flange 906 and a cylindrical portion defining the inner chamber 820.

FIGS. 23 and 24 show the ultraviolet radiation emitter 899 as being positioned proximate an exterior surface 909 of a wall 910 of the body 812 within which the outer chamber 824 is defined. The emitter 899 is adapted to emit ultraviolet radiation radially through this watt 910 into the outer air compartment 866 so as to generate ozone in the outer compartment 866 by converting oxygen of the air within the outer compartment 866 into ozone. The emitter 899 is preferably operated in a controlled manner such that ultraviolet radiation is emitted into the air compartment 866 at times when the ultraviolet radiation emitted will impinge upon air within the outer air compartment 866. Thus, for example, it is preferable to emit radiation via the emitter 899 into the air compartment 866 as when the air compartment 866 contains air as, for example, when the outer disc 844 is in a position below the emitter 899, such as when the piston 814 is in the fully extended position as shown in FIG. 23 and positions reasonably proximate thereto such as in positions in which the piston 814 is closer to the extended position shown in FIG. 23 than to the retracted position shown in FIG. 24.

In the first embodiment of the pump assembly 810 as shown in FIG. 24, in the fully retracted position, the air chamber 866 contains substantially no air and, therefore, in the retracted position shown in FIG. 24, emitted radiation from the emitter 899 will not practically serve to generate ozone in the air compartment. The emitter 899 may be controlled in a manner to be operated to emit radiation provided that any radiation emitted will reasonably impinge upon air within the air chamber 866.

In a withdrawal stroke with movement from the retracted position of FIG. 24 to the extended position of FIG. 231, the volume between the inner disc 840 and the intermediate disc 842 decreases such that fluid is displaced outwardly past the intermediate disc 842 to between the intermediate disc 842 and the outer disc 844. At the same time, the volume in the annular outer compartment 866 between the intermediate disc 842 and the outer disc 844 increases, with such increase being greater than the volume decrease in the annular inner compartment 864 between the inner disc 840 and the intermediate disc 842 such that in addition to the fluid displaced outwardly past intermediate disc 842, what is referred to herein as inhaled material namely air, liquid and/or foam is drawn inwardly via the outlet 848, central passageway 846, and the inlet passageway 854 into the annular outer compartment 866 between the intermediate disc 842 and the outer disc 844.

In a retraction stroke from the position of FIG. 23 to the position of FIG. 24, the volume in the annular outer compartment 866 between the intermediate disc 842 and the outer disc 844 decreases such that what is referred to herein as exhaled material namely air, any ozone generated, liquid and/or foam in the annular outer compartment 866 and in the central passageway 846 above the screen 856 is forced under pressure out through the screen 856. The gas comprising air and any ozone present plus the liquid simultaneously passing through the screen 856 are mixed and commingled producing foam which is discharged out the outlet 848. At the same time, in the retraction stroke, the volume in the annular outer compartment 866 between the inner disc 840 and the intermediate disc 842 increases drawing liquid from inside the fluid containing reservoir or container past the inner disc 840.

Reciprocal movement of the piston 814 between the retracted and extended positions will successively draw and pump precise amounts of liquid from the container and mix such liquid with air drawn from the atmosphere and dispense the liquid commingled with the air as a foam.

Preferably, in the course of one cycle of the piston 814, ozone is generated from oxygen in the air compartment to create ozonated air which is discharged in the retraction stroke so as to mix with the liquid and form ozonated air-liquid mixture as foam.

In a typical withdrawal stroke, the inhaled material includes material in the inlet passageway 854 and the central passageway 846, whether inwardly or outwardly of the screen 856, at the end of the last retraction stroke. Such material may typically include foam which substantially fills the central passageway 846 outward of the screen, and foam, liquid and/or air and ozone in the central passageway 846 inwardly of the screen 856 and foam, liquid and/or air and ozone in the inlet passageway 854.

The annular outer compartment 866 is, in effect, a closed bottom compartment forming a major sump whose bottom is defined by the outer disc 844, sides are defined by the side wall 836 and the inner side wall surface 766 of the stern 838 and with an overflow outlet defined by the inner opening 768 of the inlet passageway 854. Within this major sump, the annular central sump 902 is defined within the tube 900 with the sump volume of the central sump 902 being the volume of liquid which may be retained within the tube 900 above the outer disc 844 against over flow out the inlet passageway 854 to the central passageway 846.

In a retraction stroke, the material in the annular outer compartment 866 is forced out of the outer compartment 866 via the outer opening 770 of the inlet passageway 854. In the retraction stroke, the expelled material includes air, and any ozone generated and due to a venturi effect, the air being expelled through the outer opening 770 of the inlet passageway 854 entrains liquid and foam in the central sump 902 in the annular outer compartment 866 and draws the level of material in the sump down typically to the height of outer opening 770 of the inlet passageway 854. Subsequently, in the next withdrawal stroke, the inhaled material is drawn into the annular outer compartment 866 via the inlet passageway 854 and, simultaneously, a next allotment of liquid from the annular inner compartment 864 is forced from the annular inner compartment 864 past the intermediate disc 842 into the annular outer compartment 866. The inhaled material and the allotment of liquid come to sit in the central sump 902 with the liquid at the bottom of the sump, the foam above the liquid and air above the foam. With the passage of time, foam in the sump will tend to coalesce, that is, separate into air and liquid, with such coalesced liquid increasing the level of liquid in the sump. In so far as the level of liquid in the central sump 902 is below the inner opening 768 liquid will not flow due to gravity from the outer compartment 866 into the central passageway 846.

Operation of the pump assembly illustrated in FIGS. 23 to 25 will draw liquid out of a container 860 creating a vacuum therein. The pump assembly is preferably adapted for use with a collapsible container 860. Alternatively, a suitable vent mechanism may be provided if desired as, for example, for use in a non-collapsible container to permit atmospheric air to enter the container 860 and prevent a vacuum being built up therein.

Both the piston 814 and the body 812 may be formed as unitary elements or from a minimal number of elements from plastic as by injection molding.

Figure 26:
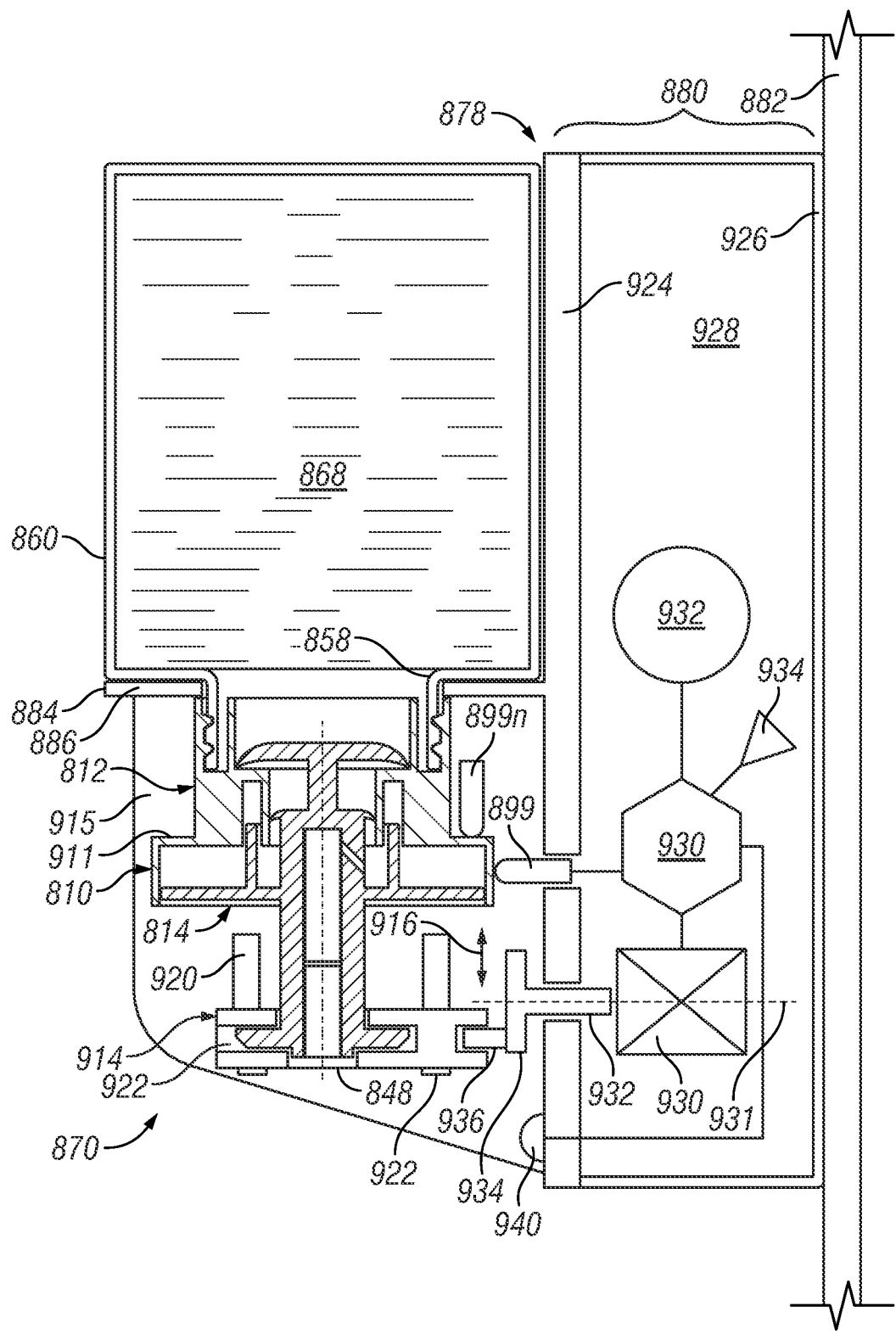
FIG. 26 is a schematic cross-sectional side view of a ninth embodiment showing an automated fluid dispenser incorporating a pump assembly, reservoir and emitter as shown in FIG. 23.

Reference is now made to FIG. 26 which shows a ninth embodiment liquid soap dispenser generally indicated 870 utilizing the pump assembly 810 of FIGS. 23 to 25 secured in the neck 858 of a sealed, collapsible container or reservoir 860 containing liquid hand soap 868 to be dispensed. Dispenser 870 has a housing generally indicated 878 to receive and support the pump assembly 810 and the reservoir 860. Housing 878 is shown with a back plate assembly 880 for mounting the housing, for example, to a building wall 882. A support plate 884 extends forwardly from the back plate assembly 880 to support and receive the reservoir 860 and pump assembly 810. The bottom support plate 884 has a forwardly opening 886 therethrough. The reservoir 860 sits supported on the support plate 884 with the neck 858 of the reservoir 860 extending through opening 886 and secured in the opening as by a friction fit, clamping and the like.

An actuator slide plate 914 is slidably mounted to the housing 878 for limited vertical movement in the direction indicated by the arrow 916. In a known manner, the housing 878 may have two side plates with one side plate 915 on each lateral side thereof which extends downwardly from the support plate 884. The actuator slide plate 914 may extend laterally between these side plates 918 of the dispenser and be engaged within vertical slide grooves 920 and 922 shown in each side plate 915 to guide the slide plate 914 in vertical sliding. The actuator slide plate 914 has a forwardly opening cavity 922 formed therein such that the piston 814 may be slid rearwardly into the cavity 922 so as to receive the engagement flange 862 within the cavity and couple the piston 814 to the slide plate 914 such that vertical sliding of the slide plate 914 slides the piston 814 coaxially within the body 812.

The back plate assembly 880 is shown to include an interior plate 924 and a rear cover 926 forming a cavity 928 therebetween. The emitter 899 is shown as mounted to the interior plate 924 in an aperture passing therethrough. A motor 930 is schematically shown as provided in the cavity 928 which rotates about axis 931 and output shaft 932 carrying a rotating wheel 934 coaxially with the shaft. A crank pin 936 is mounted at one circumferential location on the wheel. The crank pin 936 is received within a rearwardly opening horizontally extending slot in the slide plate 914. With rotation of the shaft 932 and wheel 934, engagement between the crank pin 936 and the slide plate 914 will cause the slide plate 914 to slide vertically upwardly and downwardly in a reciprocal manner relative to the housing 870.

Within the cavity 928, there is schematically shown a control mechanism 930 and a power source 932. The control mechanism 930 controls the manner of distribution of power to the motor 930 and emitter 899. A sensing device 940 is provided on the plate 924 as, for example, to sense the presence of a user's hand underneath the discharge outlet 848 of the pump 810 and activate the operation of the pump 810 in known manners. This sensing device 940 is also connected to the control mechanism 930. The control mechanism 930 may have various manners for remotely communicating with control systems or other devices and, in this regard, a communication mechanism 934 is shown in the cavity 928 connected to the control mechanism 930 which may comprise various means for wired or wireless communication with external communication devices and controllers such as through preferred WI-FI connections with the Internet and external computerized controls.

The control mechanism 930 in controlling the rotation of the motor 930 controls and is aware of the relative location of the piston 814 relative to the piston chamber-forming body 812. As a function of the position of the piston 814 with the body 812, the control mechanism 930 can control when ultraviolet radiation is emitted by the emitter 899. The control mechanism 930 can, as well, control the amount of ultraviolet radiation emitted by the emitter 899 as to, for example, intensity and duration. Preferably in a cycle of operation, the control mechanism 930 controls the emitter 899 to emit radiation into the air compartment 866 adequate to generate ozone in the air in a concentration useful for destroying pathogens. The amount of such ozone is not to be limited, however, preferably, the initial concentration of ozone after generation is at least 0.05% ozone, more preferably, at least 0.1% ozone. As used in this application, the percent of ozone is the volumetric percent of molecules of ozone in the gas at 20° C.

Preferably, in each cycle of operation of a pump, adequate ozone is generated so as to provide the desired levels of ozone in the air in the air compartment.

The control mechanism is also to be operated in a manner so as to maintain an adequate concentration of ozone in air in the air compartment having regard firstly to the natural decomposition of ozone into oxygen with the passage of time and having regard to the time that has passed since the pump was first operated in the cycle of operation to dispense air. For example, if some time has passed since the pump was last cycled, the control mechanism may generate additional ozone at periodic intervals so as to replace ozone in the air compartment which has decomposed back into oxygen. For example, if there is no operation of the pump, then ozone may again be generated every fifteen minutes or every half hour. As well, the amount of radiation which may be generated in each successive generation of ozone can be suitably controlled by the control mechanism, possibly to provide for energy efficient generation.

During the period of time when the dispenser is not expected to be used, then the control mechanism can, for example, discontinue the generation of ozone and with knowledge that it has discontinued generation of ozone, if the pump mechanism is to be cycled when the ozone would be depleted in the air compartment, the control mechanism could ensure that adequate ozone is generated before the dispenser is permitted to be cycled. The control mechanism may be able to generate ozone in a significantly small period of time as by increasing the energy of the radiation emitted through one emitter or by emitting radiation through a number of emitters simultaneously.

As to the power supply 932 which may be used, the power supply may comprise permanent hardwired AC electrical supply or, for example, replaceable batteries.

Figure 27:
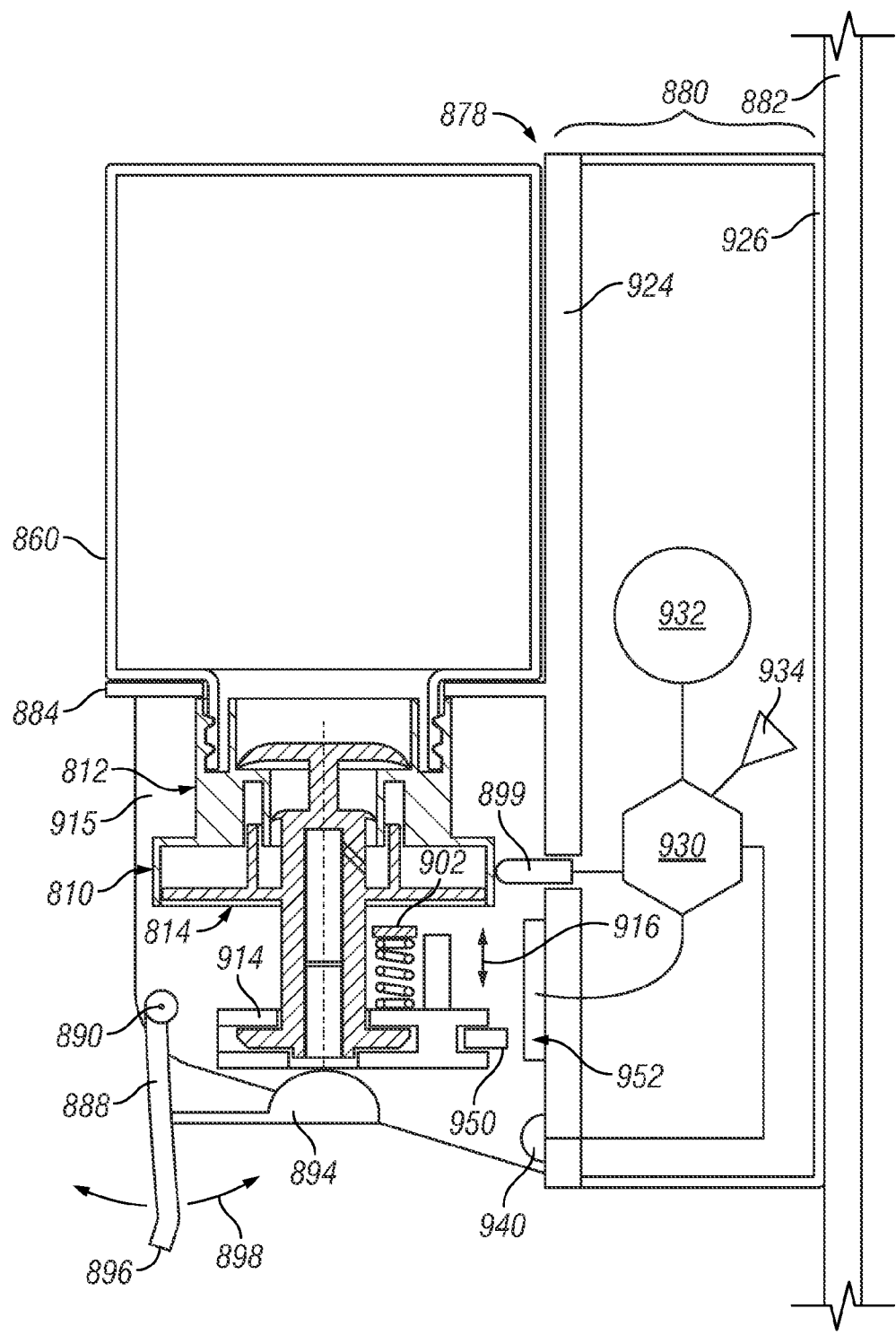
FIG. 27 is a schematic cross-sectional view of a tenth embodiment showing a manually operated fluid dispenser incorporating the pump assembly, reservoir and emitter of FIG. 23.

Reference is made to FIG. 27 which illustrates a tenth embodiment of a dispenser which is adapted to be manually operated. The manually operated dispenser of FIG. 27 is substantially identical to the automated dispenser shown in FIG. 26 with the exception that the motor, its shaft, wheel and crank pin are removed.

In the manually operated embodiment of the dispenser of FIG. 27 between the side plates 915 of the dispenser, there is carried at a forward portion an actuating lever 888 journalled for pivoting about a horizontal axis at 890. The lever 888 carries an arm 894 to engage the actuator slide plate 914 such that manual movement of the tower handle end 896 of lever 888 towards the right in the direction indicated by arrow 898 slides the slide plate 914 and therefore piston 814 inwardly in a retraction pumping stroke. On release of the tower handle end 896, a spring 762 disposed between the housing 878 and the slide plate 914 biases the slide plate 914 downwardly to move the lever and the piston 814 to the fully withdrawn position seen in FIG. 26.

The slide plate 914 is adapted to permit manual coupling and uncoupling of the piston 814 as is necessary to remove and replace reservoir 860 and pump assembly 810.

The manually operated embodiment in FIG. 27 continues to have the control mechanism 930, power source 932, communication unit 934 and sensor 940 as in the embodiment of FIG. 26. While not necessary, to assist the control mechanism in controlling the operation of the pump assembly 810, preferably a mechanism is provided whereby the controller will know the relative position of the piston 814 in the body. This, for example, cart be accomplished by a magnet 950 carried in the slot of the slide plate 914 whose position may be sensed by a magnetic sensor or sensors 952 carried on the interior plate 924 and coupled to the control mechanism.

The manual movement of the lever 888 may be utilized to generate electrical energy in an electrical generator in the same manner as for example in the first to seventh embodiments of FIGS. 1 to 22, however not shown in FIG. 27. The electrical energy generated may power the manual embodiment in creating ozone and its other functions.

Other mechanisms for moving the piston 814 as shown in FIGS. 26 and 27 can be provided including other mechanized and motorized mechanisms.

In use of the dispenser 870, once exhausted, the empty, collapsed reservoir 860 together with the attached pump 810 are removed and a new reservoir 860 and attached pump 810 may be inserted into the housing. Preferably, the removed reservoir 860 with its attached pump 810 are both made entirely out of recyclable plastic material which can easily be recycled without the need for disassembly prior to cutting and shredding.

It is to be appreciated that in the first embodiment of FIGS. 23 to 25, the inner disc 840 and the intermediate disc 842 form a first stepped pump and, similarly, the intermediate disc 842 and the outer disc 844 form a second stepped pump. The first pump and second pump are out of phase in the sense that in any one retraction or extension stroke while one pump is drawing fluid in, the other is discharging fluid out. This is not necessary in accordance with the present invention.

Figure 28:
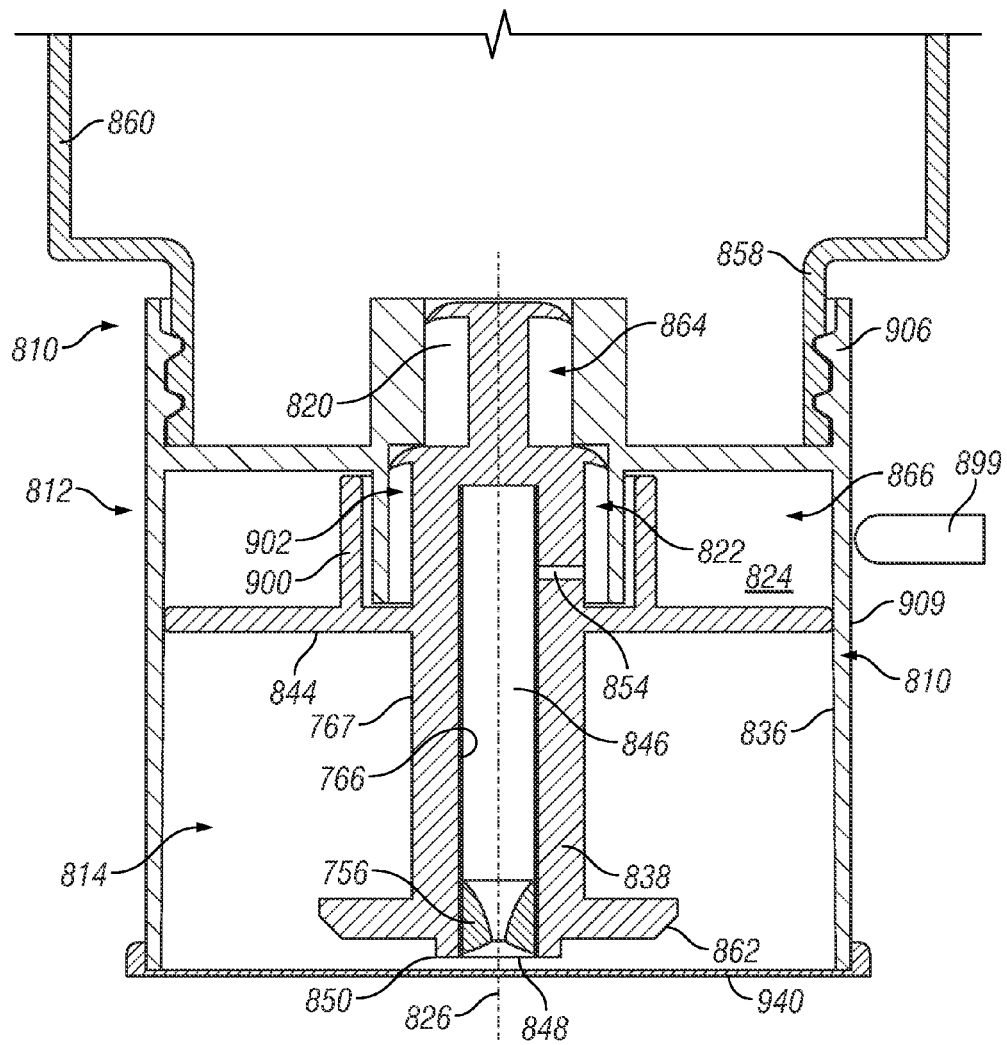
FIG. 28 is a cross-sectional side view showing an eleventh embodiment of a pump assembly in a retracted position in combination with a dispenser and emitter.

Reference is made to FIG. 28 which shows an eleventh embodiment of a pump assembly 810 of the present invention with the piston 814 in an extended position. The pump assembly 810 of FIG. 28 is similar to that of FIGS. 23 to 25 but modified to show a number of different features.

In a first difference, the air compartment 866 in the fully retracted position continues to have a volume which will contain air. Thus, as seen in the fully retracted position in FIG. 28, there continues to be a volume of air in the air compartment 866. This has the advantage that radiation from the emitter 899 can be emitted into the chamber 866 at all times during a cycle of operation and still impinge on air in the air compartment. However, the relative volume of the air chamber 866 in the fully retracted position may be selected so as to ensure that there is adequate pressurization of air in the air compartment 866 in a cycle of operation for dispensing of air and fluid from the discharge outlet 848.

The relative volume of air which may be in the air compartment 866 in FIG. 28 in a fully retracted position may, for example, be selected to be merely enough air that radiation emitted by the emitter 899 will have sufficient air to impinge on to create the ozone. Of course, in accordance with the first embodiment of the pump assembly 810 shown in FIGS. 23 and 24, likely a preferred arrangement is to control the operation of the emitter 899 so as to only emit radiation at times when the radiation will impinge upon air in the chamber having regard to the relative position of the piston 814 in the body 812 in a cycle of operation.

As a second difference, the embodiment of FIG. 28 differs from the embodiment of FIG. 23 in that the foam producing screen 856 has been eliminated and replaced by a nozzle member 756 disposed proximate the outlet 848 to at least partially atomized fluid when liquid and air pass therethrough simultaneously. Nozzle member 756 is shown to always be open to provide communication between the atmosphere and the central passageway 846. The nozzle member 756 receives the ozonated air and the liquid and further mixes them in passage therethrough to discharge an ozonated air and liquid mixture. The ozonated air and the liquid are mixed firstly in being passed together through the inlet passageway 856 and the passageway 846.

In a third difference, the inlet passageway 854 extend ends normal to the axis 826 rather than being inclined.

As a fourth difference in FIG. 28, the inner chamber 820 is of a smaller diameter than the intermediate chamber 822 and the intermediate chamber 822 is of a smaller diameter than the outer chamber 824. In FIG. 28, the inner disc 840 and the intermediate disc 842 form a first stepped pump and the intermediate disc 842 an the outer disc 844 form a second stepped pump. The two stepped pumps are in phase in a sense that both operate to discharge fluid outwardly on a retraction stroke and to draw fluid in between their respective discs on an extension stroke. In an extension stroke, the inner pump effectively serves to draw liquid from the reservoir and between the inner disc 840 and the intermediate disc 842 and to discharge it past the intermediate disc 842 between the intermediate disc 842 and the outer disc 844. The second pump serves to draw air inwardly into between the intermediate disc 842 and the outer disc 844 in a withdrawal stroke and to discharge liquid and air outwardly through the outlet 848 in a retraction stroke.

A fifth difference of FIG. 28 is that the outer wall of the body 812 has a constant outer diameter extending radially outwardly a constant amount about the threaded portion 906 and the wall 910.

A sixth difference in FIG. 28 is that the wall 910 defining the outer chamber 824 is extended axially outwardly to beyond the discharge end 848 of the piston 814 when the piston is in the fully retracted position. This has the advantage that the piston in the retracted position is protected by the body 812 against contact or damage and this can be of assistance in avoiding the need for a cap. Additionally, as a seventh difference in FIG. 28, an optional, removable cap 940 is shown removably engaged to the outer end of the wall 910 and enclosing the piston 814 within the outer chamber 824 as can be advantageous to seal the piston 814 within the chamber 824 against contamination prior to use by removal of the cap.

In the embodiments of FIGS. 23, 24 and 28, merely a single emitter 899 has been shown. However, one or more emitters may be provided in various positions about the air compartment 866. For example, two or more emitters 899 may be provided as circumferentially spaced locations about the wall 910 of the body 812 yet located to not impede the ability of the reservoir 860 and its pump assembly to be coupled and uncoupled to the dispenser 870.

One emitter 999 is shown in solid lines in FIG. 23 as emitting radiation radially into the air chamber 866. Air within the air compartment 866 may be irradiated by radiation from an emitter disposed at any direction. For example, as shown in FIG. 26, a second emitter 899a is shown adapted to direct radiation axially through a thin walled axially extending shoulder 911 into the air compartment 866.

The wall of the air compartment 866 through which radiation from the emitter 899 is to emit radiation needs to be formed of a material which permits the radiation emitted to pass therethrough. While the entire wall 910 circumferentially entirely about the axis 826 may transmit radiation, merely a window portion of the wall 910 may permit radiation to pass therethrough and thus form a window for radiation to be orientated aligned with the emitter 899.

While a portion of the wall may be adapted to permit radiation to pass therethrough into the air compartment 866, it is also within the scope of the invention that other portions of the wall 910, the body 812 and piston 814 defining the air compartment 866 be provided no as to not transmit ultraviolet radiation therethrough thus, for example, serve to entrap radiation therein by reflecting radiation back into the air, chamber or, alternatively, absorbing radiation against its transmission as to a user or other portions of the dispenser where it is not desired. The dispenser 870 may have protective covers or shrouds (not shown) to prevent radiation from being transmitted out of the air compartment as, for example, a protective cylindrical radiation impermeable or reflective shroud which might encircle the pump assembly 810 outside of the reservoir when the pump assembly is installed on the dispenser 870.

A significant advantage of the provision of ozone in an air compartment in a pump as disclosed is that the ozone assists in disinfecting internal parts of the pump and the discharge outlet of the pump in contact with the ozone so as to prevent the growth of pathogens within the pump assembly and dispenser itself. This advantage is in addition to the advantage that the ozone assists in killing pathogens after it is dispensed as, for example, on a person's hands or another use as to which the dispensed ozonated air-liquid mixture or foam may be used.

One particularly useful purpose for the ozonated foam is for use as a foam plug to block discharge of gas odors from waterless urinals as in a manner disclosed in U.S. Pat. No. 8,006,324 to Ophardt, issued Oct. 30, 2011, the disclosure of which is incorporated herein by reference. The ozone in killing pathogens assists in reducing odor in gasses from such toilet systems.

The preferred embodiments show in FIG. 23 and FIG. 24 two different arrangements of piston pumps useful in arrangement for generating ozone internally within a variable volume air chamber within the pump. However, particular configurations of pumps which can be used for generation of ozone therein is not limited to these two embodiments. For example, in any of the various pumps shown in the following U.S. patents may be useful for creation of ozone by a radiation of the air within the air chambers formed therein: U.S. Patent Application Publication US 2009/0145296 to Ophardt, published Jun. 11, 2009; U.S. Patent Application Publication US 2006/0237483 to Ophardt, published Oct. 26, 2006; and U.S. Pat. No. 6,409,050 to Ophardt, issued Jun. 25, 2002, each of which is incorporated herein by reference.

Two examples of dispensers for dispensing foam have been disclosed as FIGS. 26 and 27. Various other automated mechanisms may be utilized for dispensing foam. For example, a dispenser disclosed in U.S. Patent Application Publication US 2009/0084082 to Ophardt, which is incorporated herein by reference, could readily be adapted to use a pump assembly and emitter as shown in FIG. 23.

The two embodiments of piston pumps in FIGS. 23 and 28 have been shown for use in a dispensing apparatus which produces ozone as through the emitter 899. Each of these piston pumps is useful without generation of ozone and each has the advantage of providing a construction in which the piston pump white received in the neck of a container has a compartment outside the neck of a greater diameter than the diameter of the neck. As seen the piston 814 has inner portions formed by the inner disc 840 inside the neck 858 of the bottle 860, but the outer compartment 866 and the outer disc 844 axially outward of the neck 858 as is advantageous for providing increased volume to the outer compartment 866.

Reference is made to FIGS. 29 to 32 which show a twelfth embodiment including rotary foam pump of the type disclosed in U.S. Patent Application Publication US 2009/0200340 to Ophardt et al, published Aug. 13, 2009, the disclosure of which is incorporated herein by reference.

As shown, the foam dispensing apparatus 410 includes a mixing pump 412 having an air inlet 414 in communication with atmospheric air and a liquid inlet 416 in communication with foamable fluid 417 from a reservoir 418 via a fluid feed tube 415. The mixing pump 412 has an outlet 420 from which mixed air and liquid are discharged to pass through a foam generator 421 to produce foam 423 which is discharged out a discharge opening or outlet 422 for use.

Figure 31:
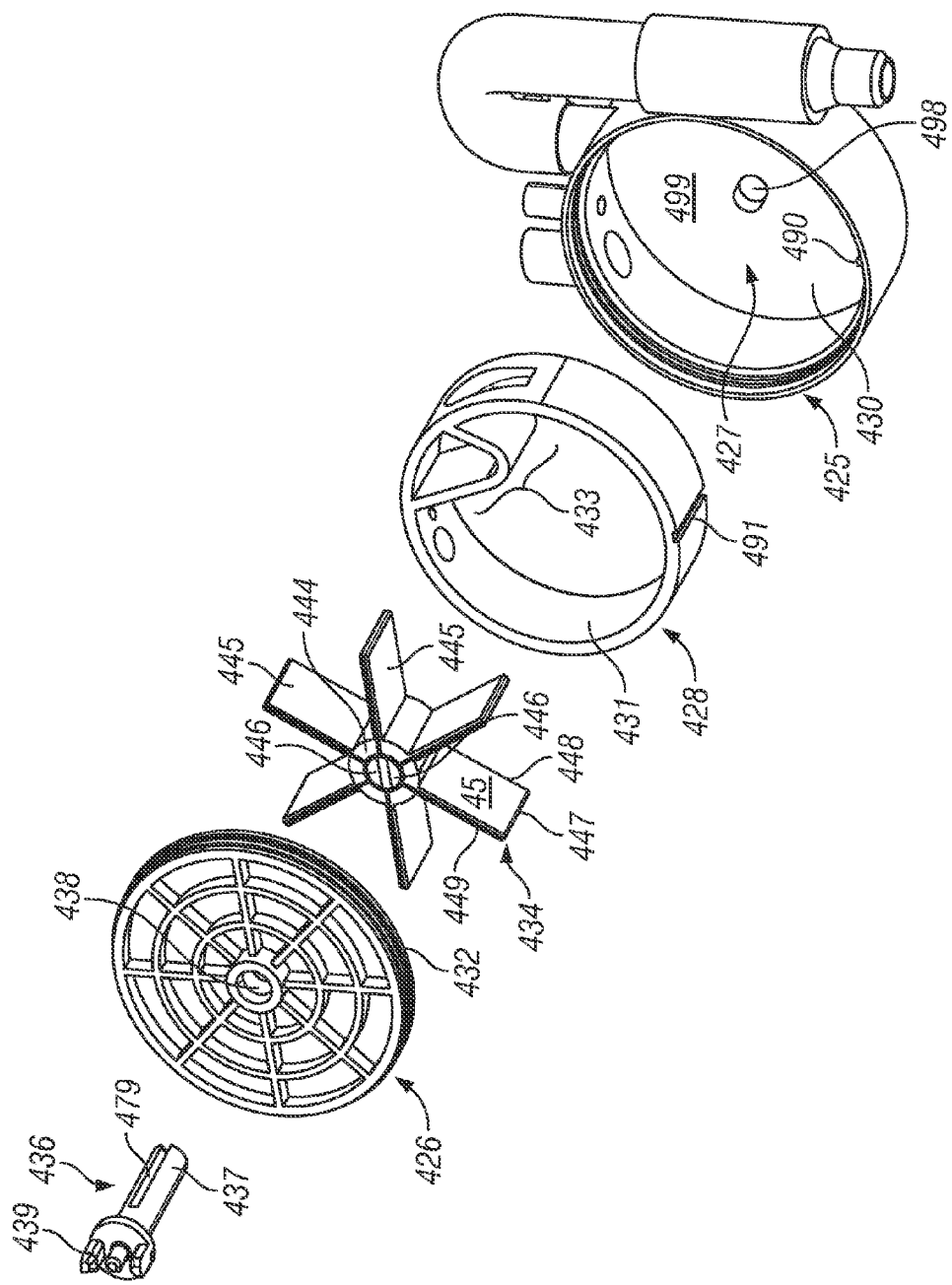
FIG. 31 is a front perspective exploded view of the pump of FIG. 29.

As seen in FIG. 31, the pump 412 has a rotor chamber-forming member comprising a principal housing member 425 and a cap-like closure member 426. A compartment 427 is defined inside the housing member 425 within which a ring member 428 is provided located keyed thereto against rotation as by an axial key 490 which extends radially inwardly on the housing member 425 being received in a keyway slot 491 in the ring member 428. An interior chamber 429 is defined inside the housing member 425 axially between an inner axially directed side wail 430 of the housing member 425 and an axially directed outer side wall 432 on the closure member 426, and radially inwardly of a radially inwardly directed end wall 431 of the ring member 428 which end wall 431 is at varying radial distances from a rotor axis 435.

A rotor member 434 is received in the interior chamber 429 journalled for rotation about the rotor axis 435 by being mounted on a rotor axle 436. The rotor axle 436 as has an axially extending slot 479 open at an inner end which is adapted to be received in two complementary slot-like openings 446 through a central hub 444 of the rotor member 434. The rotor axle 436 may be slid axially through the rotor member 434 for coupling against relative rotation. An inner end of the rotor axle 436 has cylindrical bearing surfaces 437 coaxially about the rotor axis 435 for engagement with coaxial bearing surfaces in a blind bearing bore 498 formed in the inner side wall 430 of the housing member 425. The rotor axle 436 extends through a bearing opening 438 in the closure member 426 for coaxial journaling therein preferably in sealed engagement with the bearing opening 436.

An outer end of the rotor axle 436 carries a coupling member 439 as for quick connection and disconnection with a driving mechanism to rotate the rotor axle 436.

Figure 29:
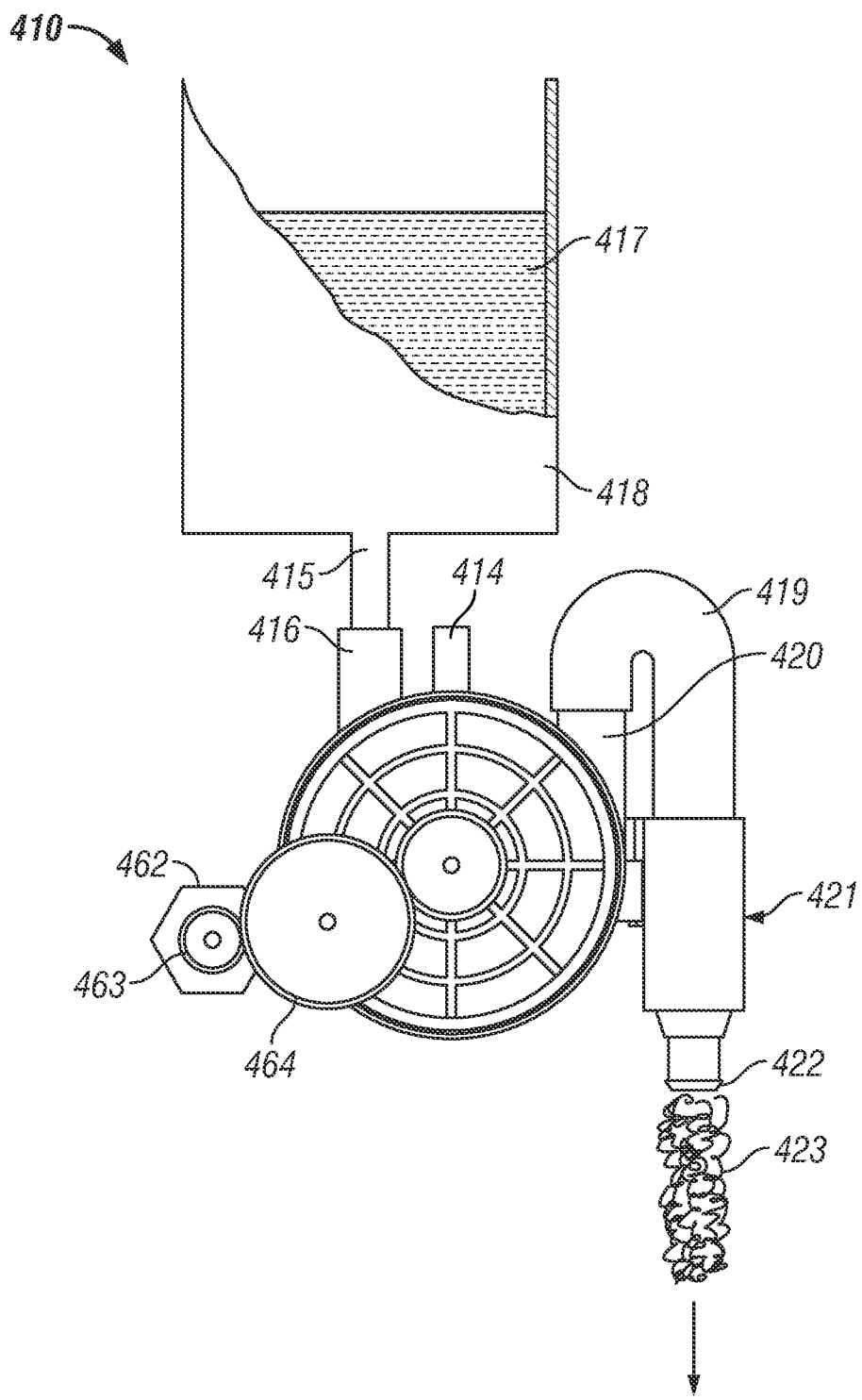
FIG. 29 is a schematic elevation view of the front of a dispenser in accordance with a twelfth embodiment of the present invention.

FIG. 29 schematically illustrates an electric motor 462 which drives a first driven gear 463 which in turn drives a second gear 464 which in turn drive third gear 465 coupled the coupling member 439 of the rotor axle 436 of the mixing pump 412.

The rotor axle 436 preferably is a rigid unitary axle member which carries the coupling member 439 at an outer end and cylindrical bearing surfaces 437 at its inner end. The rotor axle 436 is adapted for coupling with the vaned rotor member 434 for rotation of the rotor member 434 in unison with the rotor axle 436.

Figure 32:
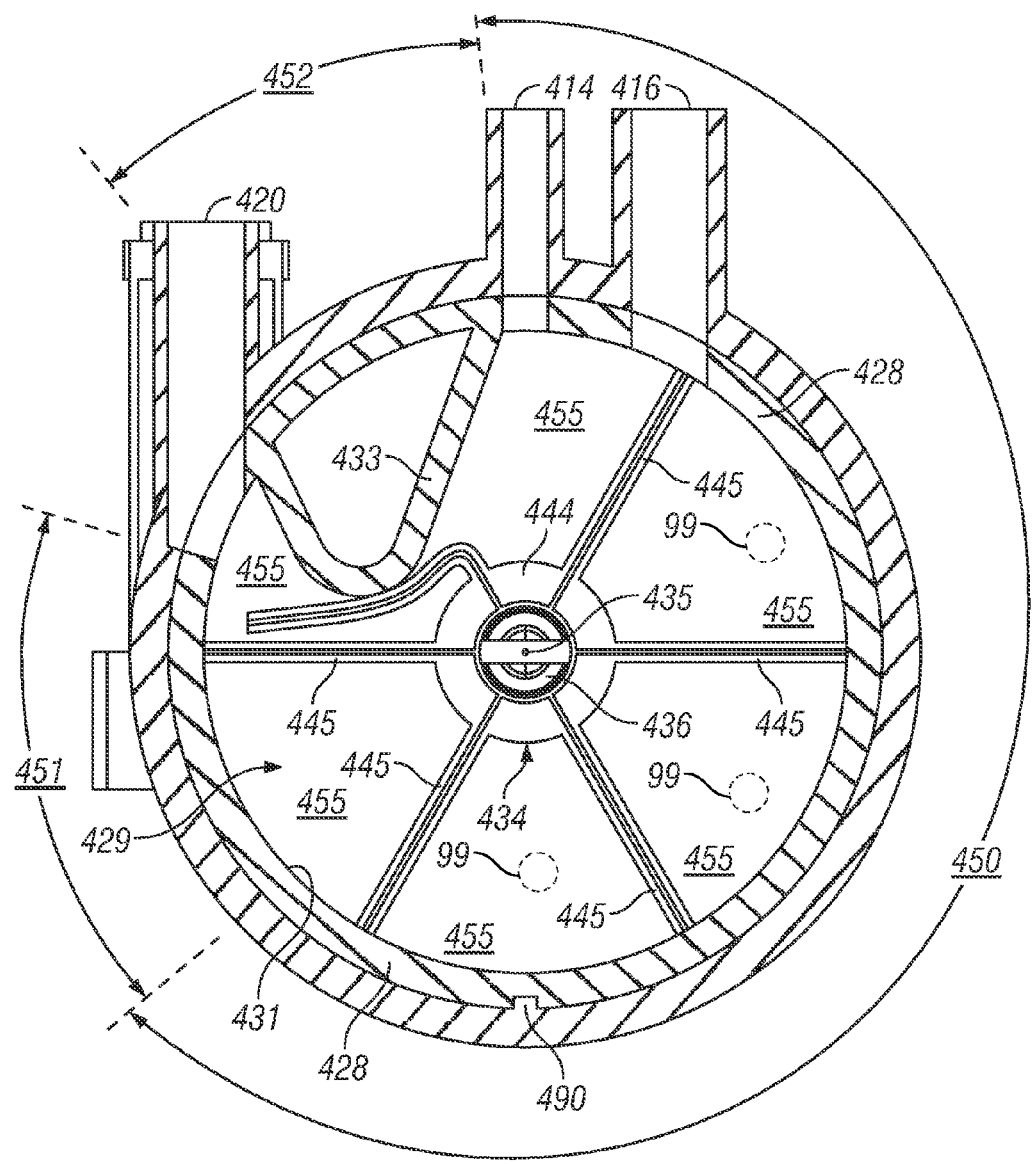
FIG. 32 is a rear view in cross-section through the mixing pump shown in FIG. 29.

The rotor member 434 has an axially extending central hub 444 with the axially extending openings 446 extending therethrough for receipt of and coupling to the rotor axle 436. A plurality of resilient vanes 445 extend radially outwardly from the central hub 444 with the vanes 445 spaced angularly from each other. Each vane 445 has an end surface 447 to be closely adjacent to or to engage the end wall 431 of the interior chamber 429, an inner side surface 448 to be closely adjacent to or engage the inner side wall 430 and an outer side surface 449 to be closely adjacent to or engage the outer side wall 432. The end wall 431 of the interior chamber 429 provided by the ring member 428 has a radial distance from the rotor axis 435 which varies circumferentially, that is, angularly about the rotor axis 435. As seen in FIG. 32, the radial distance or radius of the end wall 431 is shown to be relatively constant other than over bump section 433 where the radius is reduced.

Between each two adjacent vanes 446 and inside the end wall 431 and side walls 430 and 432, a vane chamber 455 is defined. The volume of each chamber 455 depends on the configuration that each of its two vanes assumes. In FIG. 32, the rotor member 435 is rotated clockwise. On one vane 445 first engaging the bump section 433, the vane is deflected reducing the volume of the vane chamber 455 following the deflected vane 455. The volume of that vane chamber 455 will decrease until the following vane 445 engages the bump section. The outlet 420 is open into any vane chamber 455 until the following vane 445 for that vane chamber 455 first engages the bump section. Thus, a discharge sector may be defined as that angular sector during which any vane chamber 455 is decreasing in volume and open to the outlet 420.

With reference to a trailing vane 445 defining a vane chamber, the discharge sector is shown as the angular sector 451.

For any vane chamber 455, once a leading vane 445 clears the bump section 433, as the trailing vane 445 moves down the clockwise side of the bump section 433, the volume of the vane chamber 455 will increase, until the trailing vane 445 clears the bump section. A suction sector arises during which any one vane chamber 455 increases in volume. With respect to a trailing vane 445 defining a vane chamber 455, the suction sector is shown as the angular sector 452.

Between the suction sector 452 and the discharge sector 451, there arises a mixing section 450, with reference to a trailing vane 445 of a vane chamber 455, during which the volume of the vane chamber 455 is relatively constant and next open to any one of the air inlet 414, fluid inlet 416 or outlet 420.

The volume of each of the plurality of vane chambers 455 decreases in volume when each vane chamber 455 is open to the discharge section 451 and increases in volume when each vane chamber 455 is open to the suction section 452.

The air inlet 414 and the liquid inlet 416 are provided through the end wall 431 at an angular location where each vane chamber 455 is open to the suction sector 452.

The outlet 420 is provided through the end wall 431 at an angular location where each vane chamber 455 is open to the discharge sector 451.

Figure 30:
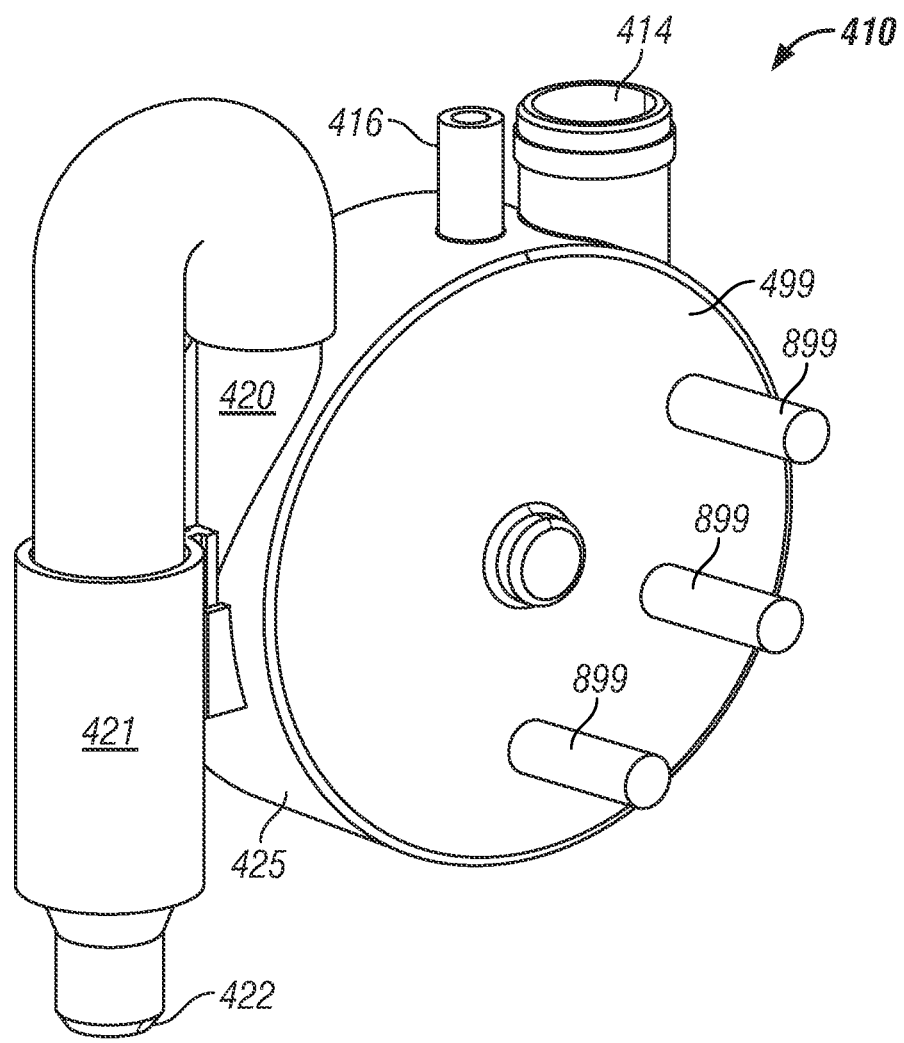
FIG. 30 is a pictorial rear view of the pump assembly of FIG. 29.

FIG. 30 shows three ultraviolet radiation emitters 899 which are arranged so as to emit radiation through the radially extending end wall 499 of the housing member 425 and into the compartment 427 so as to irradiate air within the compartment 427 forming ozone therein.

FIG. 32 schematically shows in dashed line circles the approximate axial location where each of the emitters 899 is located. The emitters 899 will emit radiation into each of the vane chambers 455 as the vane members 845 rotate internally. The radiation may in fact be directed parallel the axis of rotation into each of the compartments 855 or merely selected of the compartments. The radially extending end wall 499 of the housing member 425 is to be provided to permit ultraviolet radiation to be transferred therethrough.

With rotation of the rotor member 434, each vane chamber 455 will in sequence pass through the suction sector 452, then the mixing sector 450 and then the discharge sector 451. The increase in volume of each vane chamber in the suction section draws air into the vane chamber via the air inlet 414 and fluid into the vane chamber via the liquid inlet 416. In rotation of the vane chamber through the mixing sector, the air, ozone and fluid within the vane chamber experience some mixing as due at least partially to the higher density of the fluid compared to the air, due to the tendency of the fluid to flow downwardly under gravity and due to the relative orientation of the vanes forming the vane chamber coming to assume different relative vertical orientations. On each vane chamber 455 passing through the discharge sector 451, the decrease in vane volume will discharge air, ozone and fluid in the vane chamber out of the vane chamber through the outlet 420.

As shown in FIG. 23, the reservoir 418 is connected to the fluid inlet 416 as by a tube 415.

The outlet 420 on the housing member 427 is shown as connected by an outlet tube 419 to an inlet to the foam generator 421. The foam generator 421 comprises a rigid foaming tube having one or more foam inducing screens therein preferably fabricated of plastic, wire or cloth material or comprising, for example, a porous ceramic material. Each screen provides small apertures through which air, ozone and liquid may be simultaneously passed to aid foam production as by the production of turbulent flow through the small pores or apertures of the screen. Foam 423 produced in the foam generator 421 exits the discharge outlet 422.

In a preferred manner of operation, the foam dispensing apparatus 410 is incorporated as part of a dispensing apparatus including a mechanism for rotating the rotor axle 436 when dispensing is desired. Preferably, the rotor member 434 may be rotated as by the electric motor 462 for a desired period of time to dispense a desired amount of foam. For example, in an automated electronic dispenser, dispensing may be activated as by a user engaging an activation button or by a touchless sensor sensing the presence of a user's hand under the discharge outlet. A control mechanism then operates the electric motor 462 for a period of time rotating the rotor axle 436 and the rotor member 434 drawing air and fluid into the mixing pump 412 and forcing mixed air and fluid from the mixing pump to pass through the foam generator 421 and, hence, discharge foam from the foam generator 421 out of the discharge outlet 422 onto a user's hands. Alternately the rotor member 434 may be rotated as by a manually operated lever which preferably also operates an electrical generator to generate electrical energy.

The relative size of the vane chambers 455, the speed of rotation of the rotor member 434 and the length of time that the rotor member 434 is rotated can be used to dispense desired quantities of fluid and air as foam.

Having regard to the number of rotations of the rotor which is desired to dispense a single dose of foam and the speed with which ozone can be generated from the air inside the pump by irradiation with radiation from the emitters, levels of radiation can be selected as appropriate to create foam with desired levels of ozone. For example, insofar as the volume of the compartment 427 is relatively small and the number of rotations of the rotor member 434 may be required for each dose, then the concentration of ozone within the compartments may be selected to be relatively high say, for example, up to 5% prior to dispensing any dosage of foam. On the other hand, insofar as the irradiation can quickly produce ozone, an initial concentration of ozone can be created which is closer to the desired level of ozone in the foam to be dispensed and additional ozone can be created white the rotor member is being rotated.

Other forms of rotary pumps may be utilized as, for example, in which the inlets for liquid and air are provided in different rotary members at axially spaced locations. The irradiation by the emitters with ultraviolet light preferably may produce ozone in the air in any of the rotary sectors through which the compartments are rotated whether or not those sectors are sectors in which the volume of a compartment is reduced.

Figure 33:
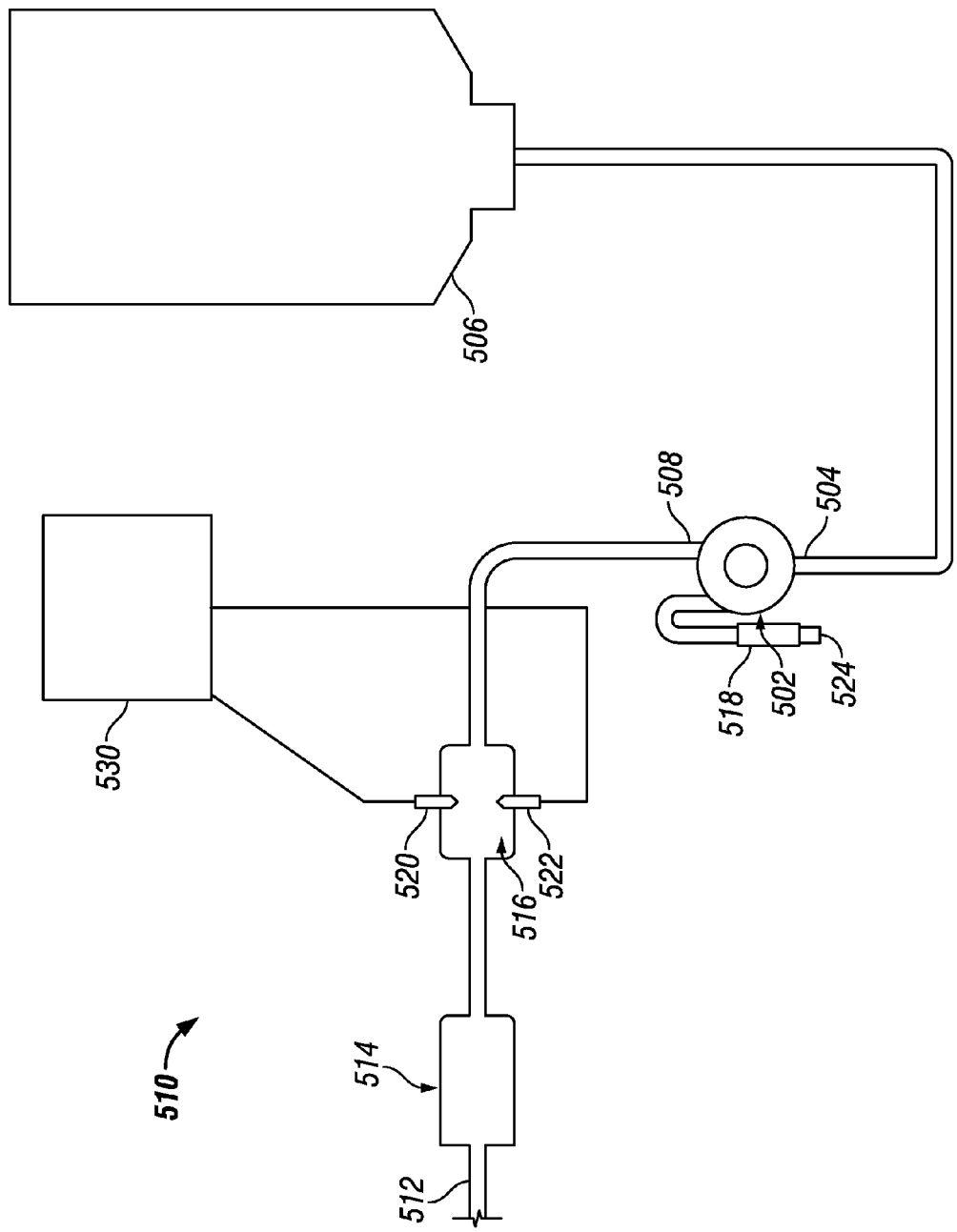
FIG. 33 shows a thirteenth embodiment of a dispenser using a corona discharge unit in combination with a rotary foam pump.

Reference is made to FIG. 33 which shows a thirteenth embodiment of a dispenser 510 in accordance with the present invention. The dispenser 500 includes a rotary foam pump 502 which has a liquid inlet 504 in fluid communication with fluid from a soap reservoir 506. The pump has an air inlet 508 in communication with atmospheric air, however, with the atmospheric air to be drawn into the rotary foam pump to pass from an air inlet 512 through a desiccant air filter 514 which serves to remove moisture from the air and then through a corona discharge chamber 516 and hence to the pump air inlet 500. The corona discharge chamber 516 may be of a known type in which an electric discharge between two electrodes 520 and 522 passes through the air forming ozone from oxygen in the air. Oxygenated air thus is provided to the air input to the rotary foam pump 502. The rotary foam pump 502 draws in the ozonated air together with liquid from the reservoir 506, mixes it within a foam generator 518 and dispenses the foam out outlet 524.

Insofar as the corona discharge chamber 516 is upstream from an air inlet to a pump, the nature of the pump is not limited to being a rotary foam pump and may comprise any manner of pump including piston pumps and the like.

A control board 530 is illustrated for control of the corona discharge chamber 516, however, it is appreciated that the control board could control also the operation of the rotary foam pump as well as otherwise control the operation of the dispenser.

Reference is made to FIGS. 34 to 38 which show a fourteenth embodiment of a dispenser 1010 in accordance with the present invention. The dispenser 1010 has many features which are identical to those shown in the ninth embodiment of FIG. 26 and similar reference numerals are used in FIGS. 34 and 35 to illustrate similar elements in the embodiment of FIG. 26.

Figure 34:
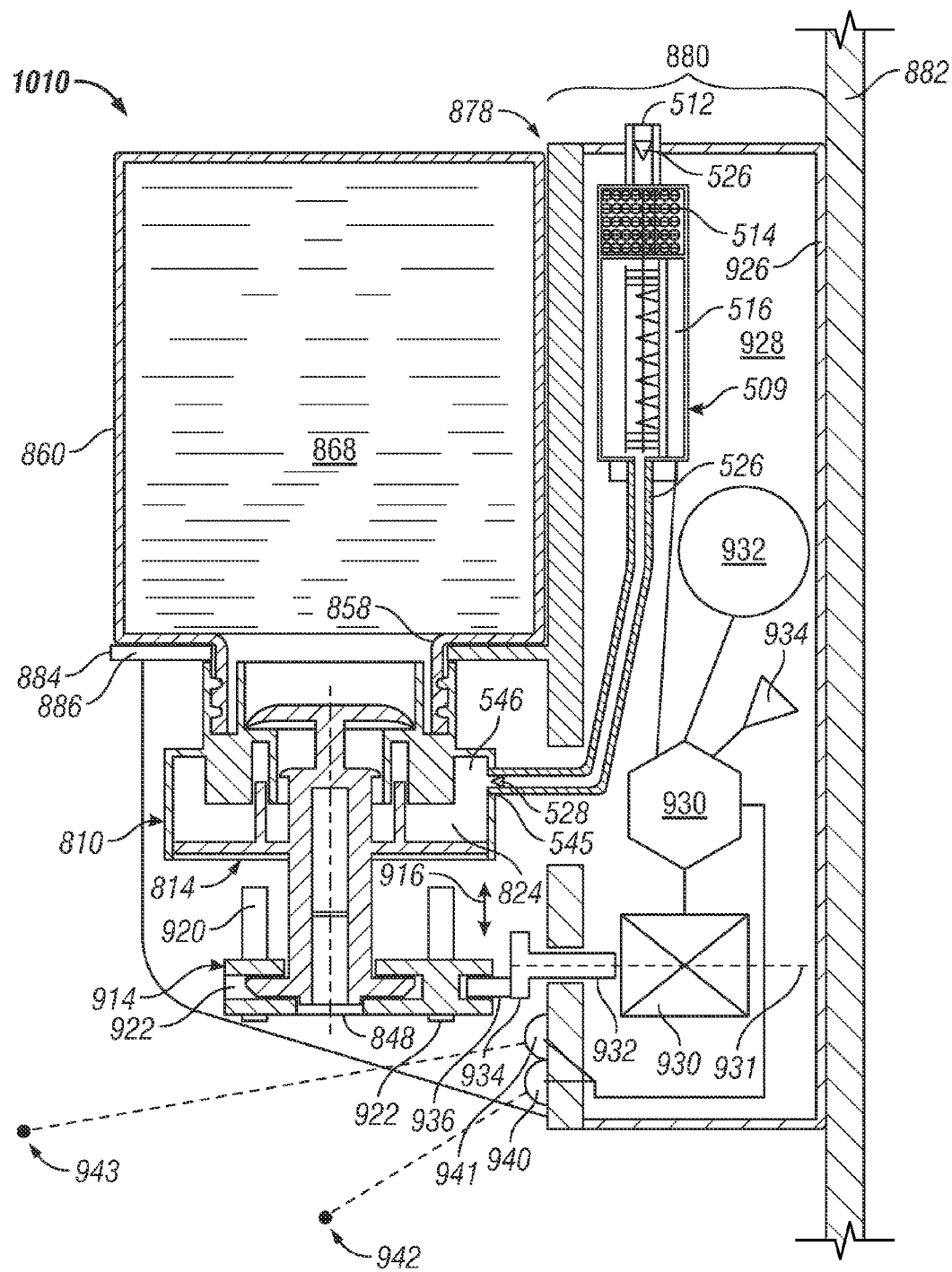
FIG. 34 is a schematic cross-sectional view of a fourteenth embodiment of a dispenser for dispensing ozone foam using a corona discharge unit in combination with a piston pump and showing the piston pump in a withdrawn position.

The fourteenth embodiment of FIG. 34 differs notably from the ninth embodiment of FIG. 26 in the manner in which ozone is generated. In the embodiment of FIG. 26, ozone is generated internally within the pump assembly 810 by emitting ultraviolet radiation from the emitters 899. In contrast in the embodiment of FIG. 34, ozone is generated within an ozone generator 509. In FIGS. 34 to 38, the ozone generator has elements similar to the dispenser shown in the thirteenth embodiment of FIG. 33 and similar reference numerals are used to refer to similar elements.

As seen in FIG. 34, atmospheric air is adapted to enter an air inlet 512 and to pass through a drying air filter 514 and into a corona discharge chamber 516 in which ozone is created and hence delivered via an ozone delivery tube 526 into the cylindrical outer chamber 824 of the pump assembly 810. In FIG. 34, a one-way inlet valve 526 is provided to permit atmospheric air to enter into the ozone generator 509 but to prevent gases inside the generator from passing outwardly. A one-way outlet valve 528 is shown in the ozone delivery tube 526 from the ozone generator to permit one-way flow of ozone from the ozone generator 509 into the pump assembly 810 but to prevent flow of fluid such as liquid, foam and/or gas from the pump assembly 810 back into the ozone generator 509. The ozone generator 509 is schematically shown as connected to and controlled by the control mechanism 930.

Figure 36:
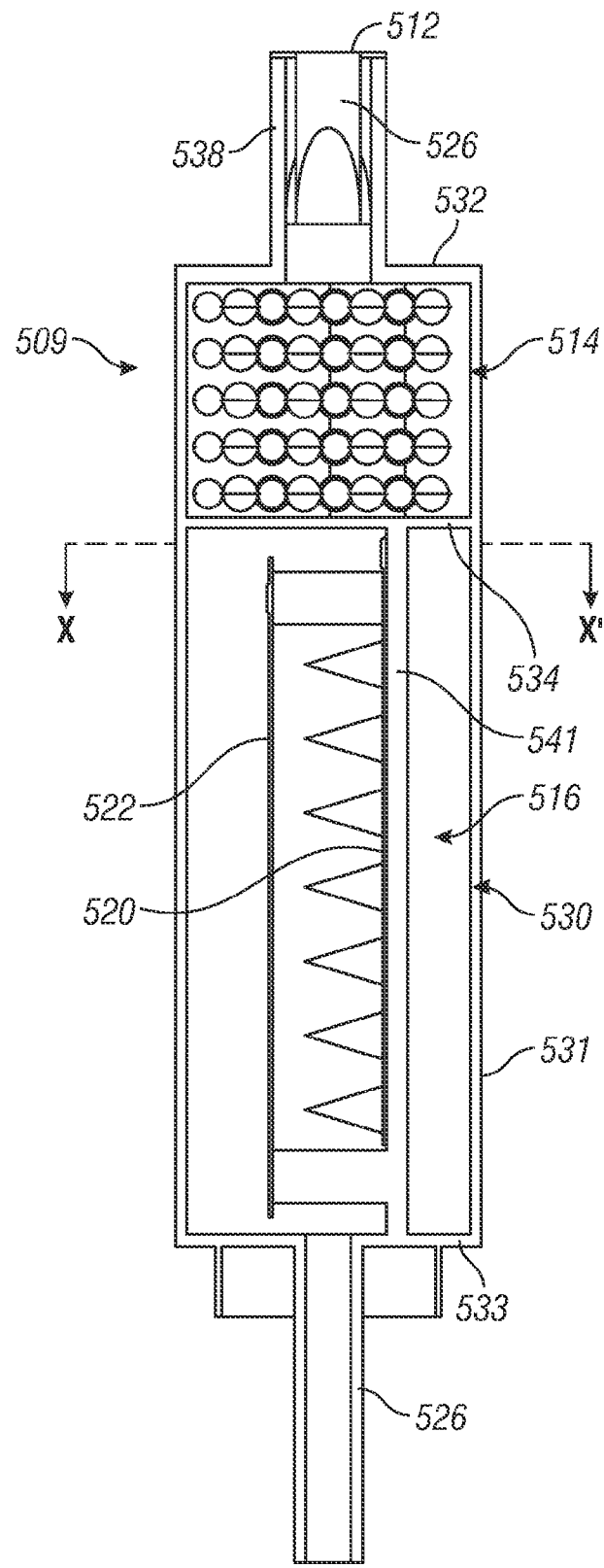
FIG. 36 is an enlarged pictorial view of the corona discharge unit shown in FIG. 34.
Figure 37:
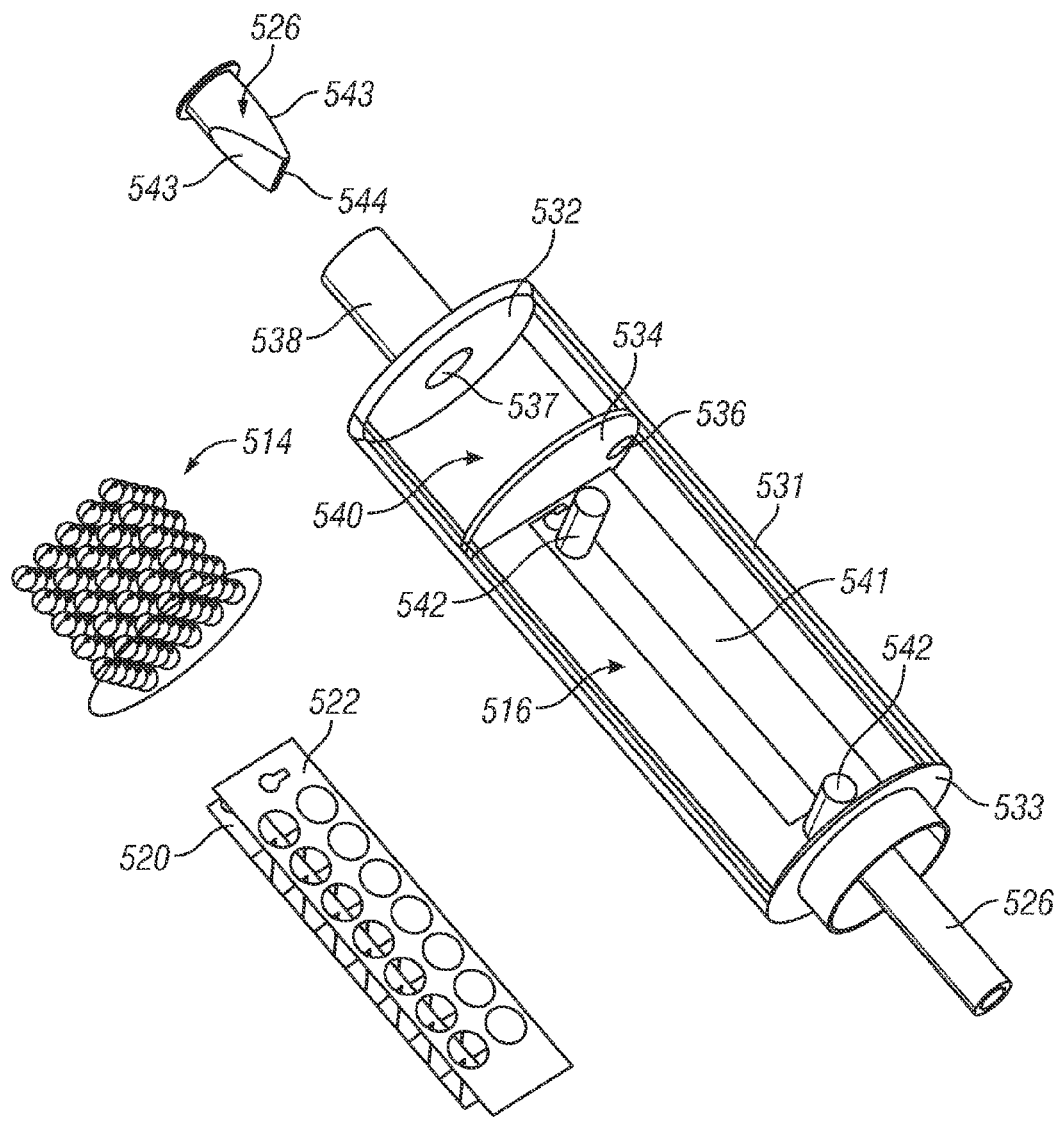
FIG. 37 is an exploded view of the corona discharge unit shown in FIG. 36.
Figure 38:
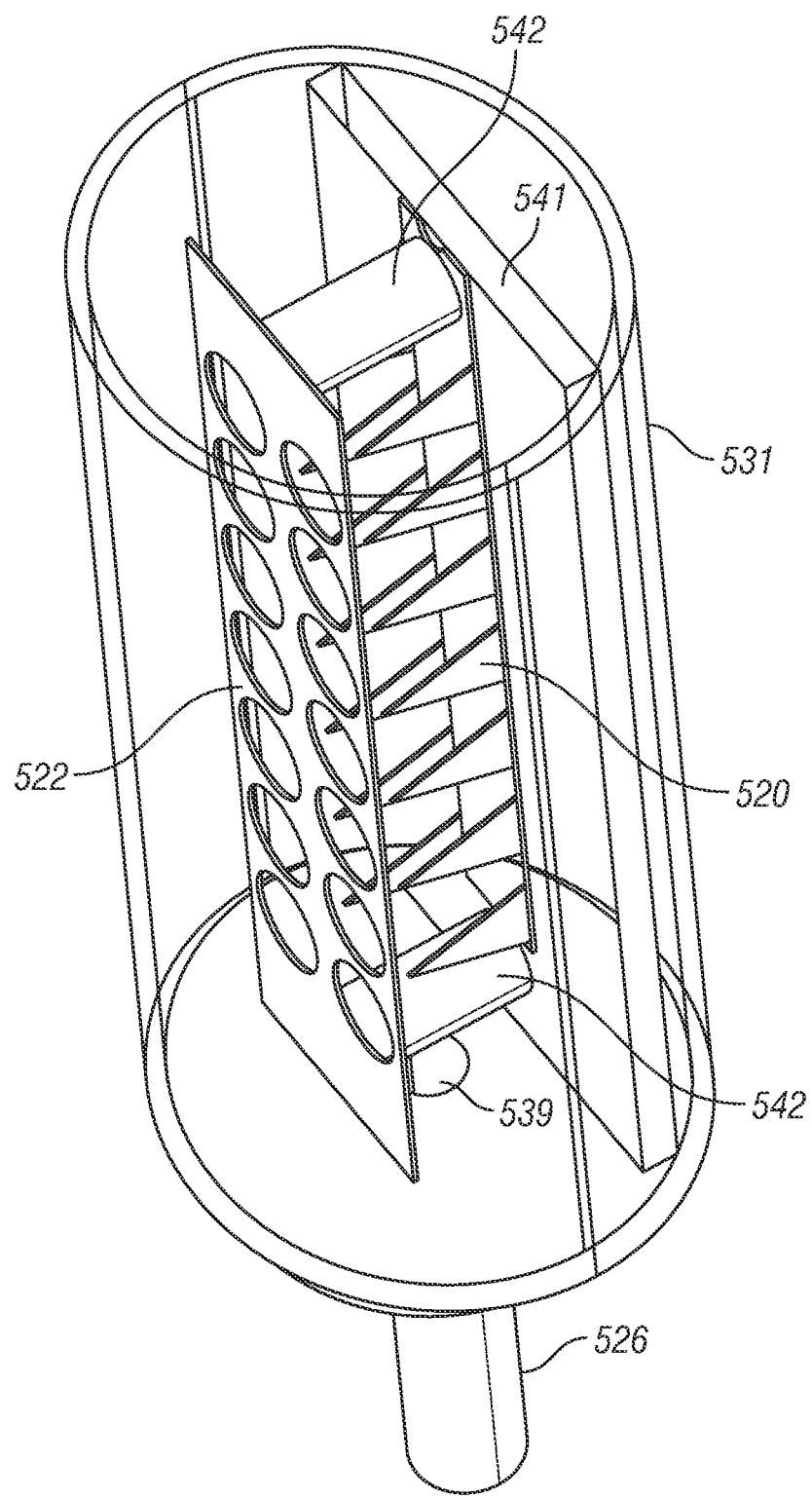
FIG. 38 is a side pictorial view of the corona discharge unit of FIG. 36 as seen below section line X-X' in FIG. 36.

Reference is made to FIGS. 36 to 38 showing additional details of the ozone generator 509. The generator 509 includes a housing 530 which includes a generally cylindrical outer wall 531, an inner end wall 532 and an outer end wall 533. An intermediate dividing wall 534 is provided in between the inner end wall 532 and the outer end wall 533. An inlet opening 536 is provided axially through the dividing wall 534. The inner end wall 532 has an opening 537 therethrough which connects with an atmospheric air inlet tube 538. The outer end wall 533 has an outlet opening 539 therethrough which connects with the ozone delivery tube 526. A passageway for air flow is thus provided through the ozone generator 509 through the inlet tube 538, through the inner end wall 532 via the inlet opening 537, through the dividing wall 534 via the opening 536 and through the outer end wall 533 via the opening 539 to ozone delivery tube 526. An air drying chamber 540 is formed within the housing 530 between the inner end wall 532 and the dividing wall 534 within which the drying air filter 514 is provided. The drying air filter 514 is shown as a matrix of media and which serves the purpose of removing moisture from air which passes through the drying chamber 540. The corona discharge chamber 516 is defined between the dividing wall 534 and the outer end wall 533 within the housing. A flat electrically non-conductive support plate 541 extends axially between the dividing wall 534 and the outer end wall 533. The first electrode 520 is mounted flush with the support plate 541 and the second electrode 522 is mounted spaced from electrode 520 and electrically insulated thereof by reason of two insulating posts 542. While not shown in the drawings, each of the electrodes 520 and 522 is connected to an electrical source such that there is electrical discharge between the electrodes 520 and 522 through air in the corona discharge chamber 516 to form ozone from oxygen in the air.

FIG. 37 shows the one-way inlet valve 526 as comprising a duck-bill type plastic valve which can be formed by injection molding and includes, as seen in FIG. 37 at its lower end, a pair of opposed flat sides 543 which are biased together at a slit line opening 544. The bias of the two sides 543 together can be overcome by creating a relative vacuum within the ozone generator 509 by operation of the pump assembly 812. Preferably, the one-way outlet valve 528 may also comprise a similar duck-bill valve to that illustrated in FIG. 37 as the one-way inlet valve 526.

Figure 35:
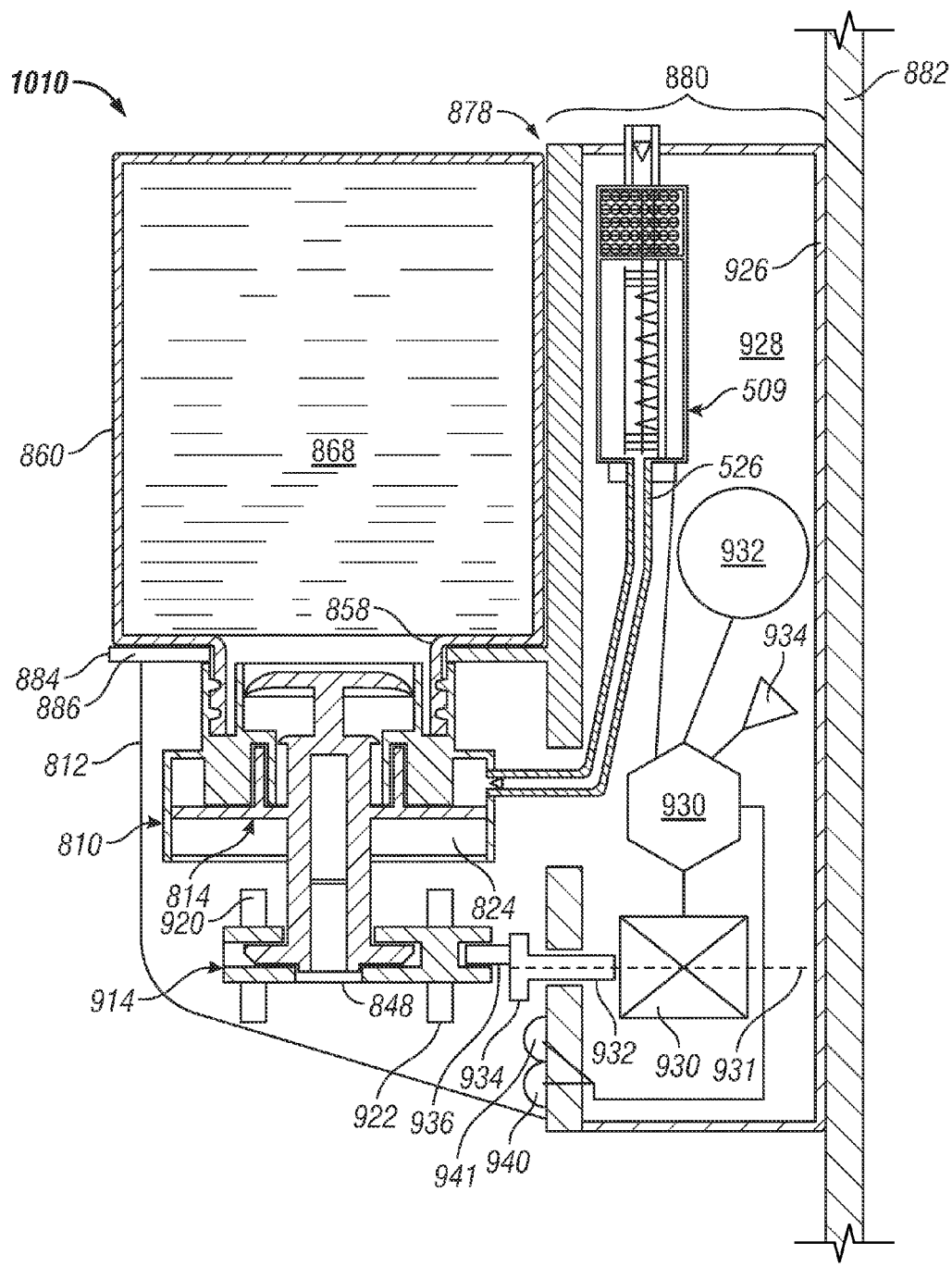
FIG. 35 is a view the same as FIG. 34 but showing the piston pump in a retracted position.

The pump assembly 810 in the embodiment of FIGS. 34 and 35 is identical to that shown in FIG. 26 with the single exception that the outer chamber 824 extends axially inwardly and upwardly as shown so as to provide a location for the outlet end 545 of the ozone delivery tube 526 to enter into the outer chamber 824 at all relative positions of the piston 814 in a normal stroke of operation. In this regard, the outlet end 545 of the ozone discharge tube 526 can be seen to open into an annular portion 546 of the cylindrical outer chamber 824.

In the dispenser of FIGS. 34 and 35, as is the case with the embodiment of FIG. 26, by rotation of the motor 930, the piston 814 is moved in a cycle of operation between a withdrawn position shown in FIG. 34 and a retracted position shown in FIG. 35.

Preferably, in operation of the dispenser 1010 of FIGS. 34 and 35, during rest periods at times when the dispenser is not in use, the control mechanism 930 will maintain the piston 814 in the retracted position as seen in FIG. 35. On the dispenser 1010 sensing the presence of a user's hand under the discharge outlet 848, the control mechanism 930 will then move the piston 814 to the extended position and, in so doing, draw ozone from the ozone generator 509, subsequently moving the piston 814 to the retracted position so as to dispense foam containing ozone onto the user's hand.

In the preferred embodiment, the passageway for the ozonated air, notably provided by the ozone discharge tube 526, leads downwardly to the bottom of the ozone generator 509 to the outer chamber 824 and is believed to be advantageous such that ozone, which is heavier than air, will have a tendency to concentrate in the lowest-most portion of the passageway, and to flow towards the outer chamber 824.

The ozone generator 509 preferably has an ozone generating capacity sufficient to generate adequate ozone for use of the dispenser under varying conditions.

The control mechanism 930 controls the generation of ozone by the ozone generator 509. As shown only in FIG. 39, n ozone sensor 160 may be provided to sense the level of ozone in the ozone generator 509 and communicate this information to the control mechanism. However, toward reducing the cost of the dispenser, the control mechanism preferably controls the operation of the ozone generator 509 without the use of an ozone sensor.

In the embodiment of FIG. 34, the control mechanism 930 controls the operation of the pump assembly and the ozone generator 509 without an ozone sensor. Methods of operation of the ozone generator 509 to provide adequate ozone include operation to provide "on demand" generation of ozone, operation to provide a pre-existing "reserve supply" of ozone, and combinations thereof.

In a preferred embodiment for an "on demand" method for generating ozone, the ozone generator may have sufficient capacity for generating ozone with time that the ozone generator 509 can generate sufficient ozone for a single activation of the pump during the time that the pump moves in a cycle of operation and move preferably with a piston pump during a charge stroke that ozonated air is drawn into the pump chamber as in the withdrawal stroke in the embodiment of FIG. 34 in which the piston is moved from its retracted position to its extended position. With many piston pump dispensers of the type illustrated in this invention, the time of a complete cycle in dispensing is, for example, about one second with the time of a withdrawal stroke being about half a second and the time of a retraction stroke being about half a second. Preferably, the ozone generator 509 of FIGS. 34 and 35 may have a capacity to generate ozone such that, for example, in a half second, adequate ozone is generated at least equal to the amount of ozone that has been drawn from the ozone generator in a single stroke of operation.

One method of operation which can assist "on demand" creation of adequate ozone with an ozone generator having a small capacity as possible is such that after the hand of a user being sensed under the discharge outlet that there is an increased time period for the ozone generator 509 to generate ozone before the end of the charge stroke drawing ozonated air into the outer chamber of the pump.

This increased time could be arranged for by providing a time delay after sensing the user's hand and initiating movement of the piston from the retracted position. However, a time delay in which no operation of the dispenser is sensed by a user is often disturbing to a user. Rather than have a time delay in operation, the pump in FIG. 34 may be controlled such that the time for the charging withdrawal stroke is greater than the time for the discharging retraction stroke. For example, rather than have the time of the withdrawal stroke be equal to the time of the retraction stroke, which is a typical arrangement, the withdrawal stoke could be longer in time as, for example, with a ration of time of withdrawal stroke to time of retraction stroke being in the range of 5:4 to 3:1, more preferably about 2:1. The overall time of a cycle of operation could be increased as well, however, it is preferred if a stroke does not exceed about 1 second or 1.5 second. As one example, the length of a cycle is maintained as about 1 second with the withdrawal stroke increased as to about ⅔ of a second and the discharge stroke reduced to about ⅓ of a second.

The control of the relative time duration of the withdrawal stroke and the retraction strokes can be accomplished various ways. As examples, the speed of rotation of the motor can be varied in each cycle and the nature of the mechanical linkage coupling the actuator slide plate 914 to the motor may be selected to provide different strokes with constant speed of rotation of the motor.

Preferably, the dispenser may be designed with the ozone generator 509 to have low electrical consumption to conserve power particularly so that the dispenser may be battery powered or powered by electricity created by a manually operated generator. Preferably, the ozone generator 509 may have a relative small volumetric size so as to not unduly increase the size of the dispenser or reduce the size of a fluid containing reservoir for the dispenser. These preferred constraints on electrical consumption and size lead towards adopting a generator with merely enough capacity to generate an amount of ozone with time which can merely meet typical demands on the dispenser.

Another method of operation which provides for increased time to generate ozone before the end of a charging stroke is to commence generation of ozone before a user's hand is sensed under the piston 810.

Referring to FIG. 34, the dispenser is shown as including in addition to the sensor 940, a second sensor 941 for preferred, albeit optional, use in a manner now described. In accordance with the various embodiments of the invention, the sensor 940 is preferably adapted to sense the presence of a user's hand disposed below the piston 810. FIG. 34 schematically illustrates the sensor 940 as adapted to determine whether or not a person's hand may be disposed as, for example, at a location 942 marked on FIG. 34 substantially directly below the piston 810. The secondary sensor 941 may preferably be adapted to sense the location of a person's hand or the user at a location spaced from the dispenser as, for example, one foot or two feet or three feet spaced forwardly from the dispenser and schematically illustrated as a location 943. The secondary sensor 941 can be used towards sensing the approach of an expected user to the dispenser and thus provide a signal indicating the user of the dispenser at a time period before a time when the primary sensor 940 senses the position of a person's hand underneath the piston 810. This advance warning that a user will use the dispenser may be used as an input to the control mechanism 930 so as to have the control mechanism 930 direct the ozone generator 509 to commence generating ozone at a time earlier than would result if a request for generating ozone was not initiated until the user's hand is sensed underneath the piston by the primary sensor 940. This advance notice that a user is to use the dispenser and earlier initiation of generation of ozone with the ozone generator can be of assistance towards ensuring that there will be adequate ozone in the ozone generator to be drawn by the piston pump in an initial withdrawal stroke from the position of FIG. 35 to the position of FIG. 34. For example, this may be advantageous if, for example, the capacity of the ozone generator 509 to generate ozone may be limited. Rather than provide two different sensors 940 and 941, a single sensing mechanism may be used which has a capability of sensing the presence of a user at different locations. Pairs of sensors of the type disclosed in U.S. patent publication US 2009/0045221 to Ophardt, published on Feb. 19, 2009, may be used.

As contrasted with the "on demand" methods of control of the ozone generation, another method is to maintain a supply of ozonated air in the ozone generator 509 ready to be used, and to replenish this supply by generating more ozone when ozonated air is withdrawn. In such an arrangement, the ozone generator need not have a capacity to generate adequate ozone in the same time as a charging withdrawal stroke and, for example, replenishment could be adequate if the ozone generator created adequate ozone for replenishment in the time of a cycle, for example, one second of generation of ozone for a one second cycle of pump operation. However, since there may on average be expected to be a greater time period between activations of the dispenser by different users than merely time of one cycle of operation, the ozone generator could have a capacity to generate adequate ozone for a single cycle in a time greater than the time of the single cycle, for example, in the time of two, three or four cycles.

The ozone generator 509 could also be controlled in a manner that there is constantly adequate ozone within the corona discharge chamber 516 for at least one cycle of operation of the pump and, more preferably, two, three or more cycles of operation of the pump.

Ozone has a tendency to revert back to oxygen over time. Thus, within the ozone generator, ozone that may be generated within the corona discharge chamber 516 will, after time, revert back to being oxygen. Under typical temperature and relatively low humidity conditions, the half life of ozone may be approximated as thirty minutes. The half life is the time that it takes for half of the ozone to revert to oxygen.

Preferably, the control mechanism 930 controls operation of the ozone generator 509 by estimating the ozone in the generator at any time having regard to one or more of: monitoring of the number of activations of the pump, estimating the amount of ozone generated in the ozone generator 509 over time, estimating the amounts of ozone withdrawn by the activations of the pump, monitoring time and estimating the amount of ozone in the ozone generator which has reverted to oxygen over time. The control mechanism 930 can direct the ozone generator 509 to generate ozone from time to time as may be required so as to maintain the ozone concentration within the ozone discharge chamber 516 within pre-established limits to assist in ensuring that there is adequate ozone in the corona discharge chamber 516 for at least one and possibly a number of activations of the pump.

As one example, an ozone generator was selected to produce adequate ozone for a simple cycle of operation of the piston pump during that cycle of operation. An ozone generator with an internal volume of 35 ml has been tested in a dispenser as illustrated in FIG. 35 which generates adequate ozone in one second for a typical single dose of foaming liquid of 1.0 ml dispensed in a volume ratio of liquid to ozonated air of 1:15 and in which the ozonated air has a concentration of about 0.05% by volume ozone. This tested ozone generator was used to supply ozone to a piston pump with initiation of generation of ozone by the generator to coincide with the initiation of the withdrawal stroke and the ozone generator to generate ozone for ½ second during the withdrawal stroke. The discussion of the control of generation of ozone has been principally directed to a discussion in the conduct of a piston pump as illustrated in FIG. 34 in which ozone is charged into the pump chamber in a withdrawal stroke. Of course, other piston pumps could be selected in which ozone is charged into the pump chamber as the piston is retracted. In either case, on demand ozone generation is preferred during a charge stroke when ozone is drawn into the pump.

In accordance with the present invention, a dispenser is provided for dispensing with a pump a liquid and ozonated air as a foam with the dispenser including a removable replaceable cartridge as a carrier for liquid to be dispensed and an air drying media to be consumed in drying air from which the ozonated air is produced. Preferably, the replaceable cartridge may also include a pump mechanism. Preferably, the cartridge may be coupled and uncoupled to a housing for the dispenser by movement which simultaneously couples the pump mechanism to a pump activator, the air dryer media across an inlet passageway to an ozone generator and an ozone discharge outlet to an ozonated air inlet to the pump mechanism.

Figure 39:
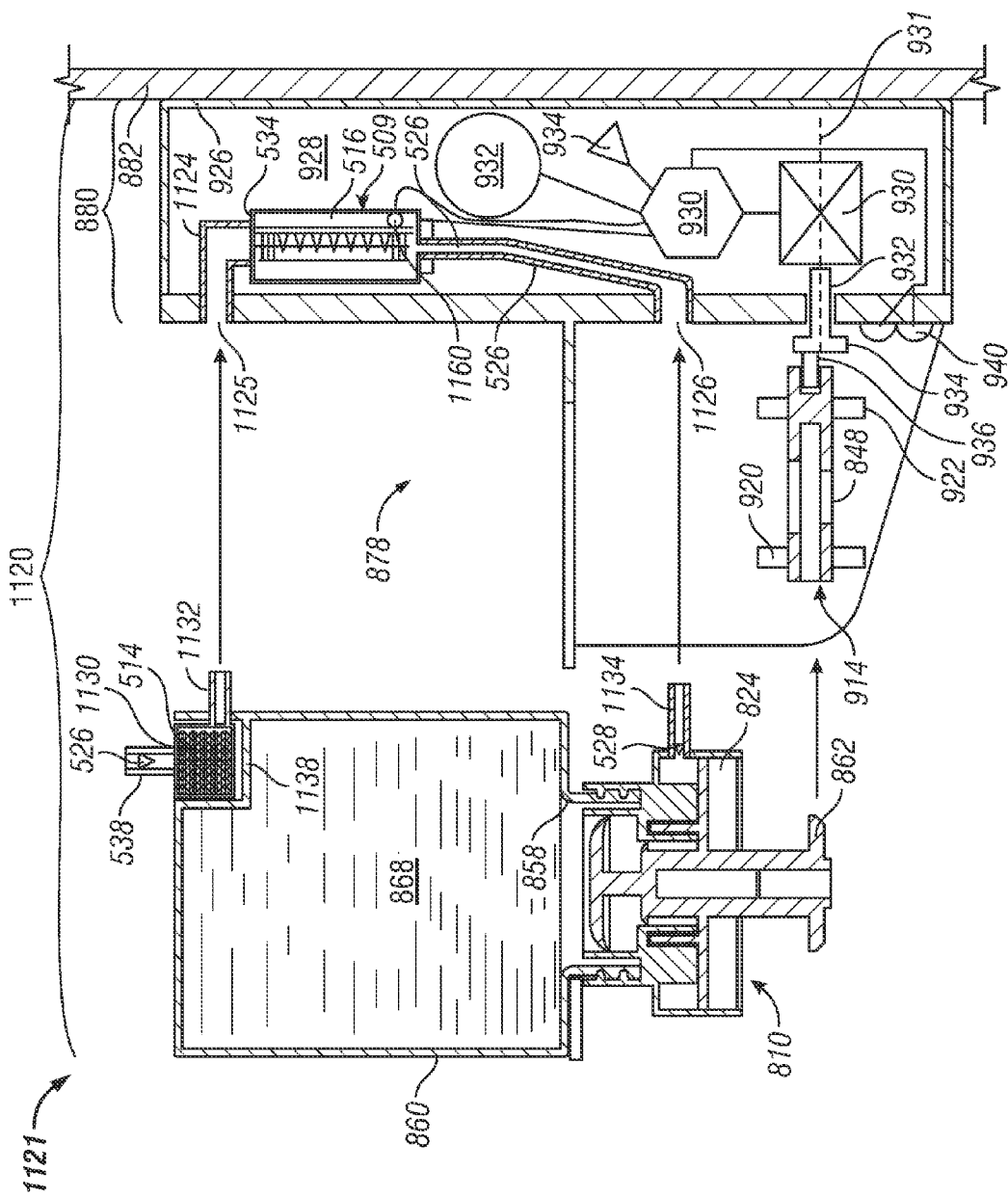
FIG. 39 is a cross-sectional side view showing a fifteenth embodiment of a dispenser using a corona discharge unit in a partially exploded configuration.

Reference is made to FIG. 39 which illustrates a fifteenth embodiment of a dispenser 1120 in accordance with the present invention which is substantially identical to that shown in the embodiment of FIG. 34 but for the modification of the ozone generator 509 to provide the air drawing filter 514 as severable from the remainder of the ozone generator as part of a removable cartridge 1121 carrying firstly, the pump assembly 810, secondly, the fluid reservoir 860 and, thirdly, the air drying filter 514. Referring to FIG. 39, the corona discharge chamber 516 is provided within its own housing which has an inner plate 534 carrying an inlet tube 1124 having an inlet 1125 directed horizontally forwardly relative to the wall 882 on which the back plate assembly 880 of the dispenser is mounted. The ozone discharge tube 526 from the corona discharge chamber 516 is also shown to have an outlet 1126 which is directed horizontally forwardly.

The reservoir 860 is illustrated as being modified at its upper rear no as to provide a recess 1128 bounded on three sides and within which an air dryer housing 1130 carrying the air drying filter 514 may be removably secured. The air drying filter 516 is shown as being sandwiched between the air dryer housing 1130 and the reservoir 860. The air dryer housing 1130 carries the inlet tube 538 and the inlet one-way valve 526. An outlet tube 1132 from the air dryer housing 1130 is shown as being cylindrical and extending horizontally rearwardly.

The pump 810 is shown as carrying on its rear a rearwardly extending cylindrical inlet tube 1134 carrying the one-way valve 528.

The cartridge 1121 is thus adapted to be slid horizontally rearwardly relative the back plate assembly 880 of the dispenser and with such horizontal movement simultaneously, the outlet tube 1132 for the air drying filter 514 becomes seatably engaged within the inlet 1125 to the inlet tube 1124 to the corona discharge chamber 516, the inlet tube 1134 on the pump assembly 810 becomes sealably engaged in the outlet 1126 of the ozone discharge tube 526 of the corona discharge chamber 516 and the actuator 862 on the piston 514 become coupled with the actuator slide plate 914. Thus, in a simple manner, the cartridge 1121 can, by relative horizontal movement, be readily coupled to and uncoupled from the dispenser housing 878.

Advantageously, the cartridge 1121 can provide an adequate volume of fluid 868 to be dispensed and, as well, an adequate supply of air drying media to reasonably dry air for a period of time that the cartridge 1121 may be expected to be coupled to a dispenser.

In accordance with the present invention, a foam liquid product is provided dispensed from the outlet of the dispenser in which air within the bubbles in the foam includes ozone within a concentration effective for various purposes including notably cleaning, disinfecting and, preferably, killing pathogens. In accordance with the present invention, it is preferred that the liquid which is to foam and form the bubbles to contain the ozonated air may be a cleaning fluid, however, this is not necessary. The liquid which is to foam and form the hubbies to contain the ozonated air may merely serve the purpose of a carrier for the ozonated air. Preferably, the bubbles of the foam may remain unbroken for a period of time that the ozone may be delivered to where cleaning or disinfecting is desired as, for example, on all and various different surfaces of a person's hand or to surfaces which are to be cleaned. Preferably, the foam containing ozone will have bubbles with a tendency to remain unbroken for a period of time preferably of at least one second, or two seconds or three seconds or five seconds or ten seconds or more to assist in providing adequate time for the foam after generation to be applied to surfaces to which it is to clean or disinfect.

The relative ratios of gas to liquid which may comprise the bubbles of the foam may be varied depending upon the nature of the liquid and the desired purposes of the foam.

Many typical foaming liquids with cleaning properties are known and which can be foamed with the volume of liquid injected relative to the volume of air injected being in the range of about 1 to 10 to 1 to 15. Such relative ratios are also suitable for use with ozonated air. Advantageously, the relative volumes of liquid to air containing ozone may be greater as, for example, in the range of about 1 to 15 to 1 to 50 or 1 to 60 as may be desired. Such an ozonated air containing foam with a low relative amount of liquid can be advantageously used as a vehicle to provide cleaning or disinfecting effective levels of ozone on surfaces to be cleaned. In accordance with the present invention, there is provided a particularly useful foam product having liquid to gas ratios in the range of 1 to 10 to 1 to 60 and, preferably, with half fife times for the foam, defined as the time in which half of the foam bubbles become broken, being in the range of three seconds to thirty seconds or longer. Such foams can serve as an advantageous vehicle for delivering ozone into any environment which is desired to be cleaned including a person's hands, articles, walls, a toilet bowl and, as well, wounds, sores, burns or other openings in a human or animal body.

Ozone is soluble in water. During the mixing of the ozonated air and liquid to form the foam, the ozone within the ozonated air will have a tendency to become dissolved in the liquid, particularly if it is water based or to react with the liquid or components of the liquid since ozone is a strong oxidizing agent. Ozonated water is useful as a cleaner and sanitizer.

The resultant foam product can provide for advantageous cleaning by reason of both the delivery of ozonated air in the foam bubbles and by reasons of the delivery of ozonated liquid preferably ozonated water. The liquid used to make the foam preferably is selected to minimize reaction with ozone which reduces the ozone concentration in the ozonated air or the liquid. The particular foaming agents used in the foaming liquid preferably are agents which do not react with ozone.

The foam provides an excellent high liquid to air surface area for transfer of ozone from the ozonated air into the liquid of the foam.

With knowledge of the extent to which ozone will be dissolved into the liquid, the concentration of ozone in the ozonated air may be selected to provide for a resultant foam with advantageous ozone dissolved in the liquid of the foam and ozone remaining in the air of the foam bubbles for cleaning and disinfecting purposes as desired.

While the invention has been described with reference to preferred embodiments, many modifications and variations will now occur to persons skilled in the art. For a definition of the invention, reference is made to the following claims.

We claim:

1. A method of operating a hand cleaner dispenser to dispense ozone containing fluid onto a user's hand comprising:
providing a pump having an air compartment,
operating the pump in a cycle of operation including the steps of drawing atmospheric air into the air compartment and discharging air from the air compartment,
generating ozone within the air compartment from air in the air compartment by conversion within the air compartment of oxygen in the air within the air compartment into ozone to form ozonated air in the air compartment,
mixing the ozonated air with a flowable fluid to form an ozonated fluid-air mixture, and passing the ozonated fluid-air mixture out a discharge outlet onto a user's hand,
wherein the pump comprises a housing and an impeller movable within the housing, the air compartment and the liquid compartment are formed within the housing between the housing and impeller,
the air compartment is defined at least in part by a wall of the housing in which it transmits ultraviolet radiation,
the method includes passing ultraviolet radiation through the wall into the air chamber to irradiate air in the compartment with radiation adequate to convert the oxygen in the air into ozone.

2. A method as claimed in claim 1 wherein, generating ozone within the air compartment comprises irradiating air in the compartment with radiation adequate to convert the oxygen in the air into ozone.

3. A method as claimed in claim wherein the step of generating ozone creates an initial Ozone concentration in the air in the compartment of at least 0.1% by volume immediately after creating the ozone.

4. A method as claimed in claim 1 wherein the step of generating ozone creates an initial ozone concentration in the air in the compartment in the range of 0.05% to 5% by volume.

5. A method as claimed in claim 1 wherein the fluid comprises a liquid which is capable of foaming,
the method including passing the ozonated air and the flowable fluid simultaneously through a foam generator to generate foam for discharge out the discharge outlet.

6. A method as claimed in claim 1 wherein the pump having a liquid chamber compartment in communication with a reservoir containing the flowable fluid, the cycle, of operation of the pump including the steps of drawing liquid, into the liquid compartment, and discharging liquid from the liquid compartment, including discharging the liquid from the liquid compartment before mixing the liquid with the ozonated air.

7. A method as claimed in claim 6 wherein the pump is a manually operated pump coupled to an electrical generator for generating, electrical energy such that on a user manually operating the pump the generator generates electrical energy,
the method including manually operating the pump to generate electricity with the generator and using the electricity generated to generate ozone within the air compartment.

8. A method as claimed in claim 1 wherein the impeller is movable relative the pump housing in the cycle of operation in which the air compartment having a variable volume which changes from a minimum volume to a maximum volume.

9. A method as claimed in claim 1 wherein the pump is a rotary displacement pump.

10. A method as claimed in claim 1 wherein the pump is a piston pump, the housing comprises a piston chamber-forming member, the impeller comprising a piston-forming element reciprocally coaxially slidable within the piston chamber-forming member in which the air compartment and the liquid compartment are formed between the piston-forming element and the piston chamber-forming member,
the air chamber is defined in part by a wall of the piston chamber-forming member which is transmits ultraviolet radiation, the method including passing ultraviolet radiation through the wall into the air chamber to irradiate air in the compartment with radiation adequate to convert the oxygen in the air into ozone.

11. A method as claimed in claim 1 including discharging the liquid from the liquid compartment into the air compartment.

12. A method as claimed in claim 11 including discharging ozonated air and liquid from the air compartment through a foam generator to generate the ozonated fluid-air mixture as a foam for discharge out the discharge outlet.

13. A method as claimed in claim 10 wherein the piston-forming element is reciprocally movable relative the piston chamber-forming member in the cycle of operation between a retracted position and an extended position, the air compartment having a variable volume which changes from a minimum volume to a maximum volume, the volume of the air compartment being at the maximum volume when the piston-forming element is in a first position of the retracted position and the extended position, the volume of the air compartment being at the minimum volume when the piston-forming element is in a second position of the retracted position and the extended position different than the first position, carrying out the step of generating ozone in each cycle including generating ozone after the piston-forming element has reached the first position.

14. A method as claimed in claim 1 wherein the method includes controlling the generation of ozone in the air chamber such that if a predetermined period of time passes after last generation of ozone without discharge of air from the air compartment generating additional ozone within the air compartment from air in the air compartment by conversion within the compartment of oxygen in the air within the compartment into ozone.

15. A method of operating a hand cleaner dispenser to dispense ozone containing fluid onto a user's hand comprising:

providing a pump having an air compartment, operating the pump in a cycle of operation including the steps of drawing atmospheric air into the air compartment and discharging air from the air compartment, generating ozone within the air compartment from air in the air compartment by conversion within the air compartment of oxygen in the air within the air compartment into ozone to form ozonated air in the air compartment, mixing the ozonated air with a flowable fluid to form an ozonated fluid-air mixture, and passing the ozonated fluid-air mixture out a discharge outlet onto a user's hand, wherein the step of generating ozone creates an initial ozone concentration in the air in the compartment immediately after creating the ozone which initial ozone concentration is selected to meet one of a plurality of pre-determined minimum ozone concentrations, providing to the dispenser information regarding risk of infection in the environment in which the dispenser is located, and selecting the one of the plurality of pre-determined minimum ozone concentrations as a function of the information received regarding the risk of infection to provide an increased initial ozone concentration with an increase in the risk of infection.

16. A method as claimed in claim 1 carried out utilizing a hand cleaner dispenser comprising:

a fluid containing reservoir, a pump mechanism including a housing and an impeller movable within the housing, an air compartment and a liquid compartment formed within the housing between the housing and impeller, the impeller movable relative the housing in as cycle of operation (a) to successively draw atmospheric air into the air compartment and discharge air from the air compartment and (b) to successively draw liquid from the reservoir into the liquid compartment and discharge liquid from the liquid compartment, the air compartment defined at least in part by a will of the housing which transmits ultraviolet radiation, an emitter of ultraviolet radiation when activated directs ultraviolet radiation through the wall into the air compartment to irradiate air in the air compartment with ultraviolet radiation adequate to convert oxygen in the air in the air compartment into ozone forming ozonated air, a mixing chamber for simultaneous passage of ozonated air which has been discharged from the air compartment and fluid which has been discharged from the liquid compartment.

* * * * *